United States Patent [19]
Bojsen et al.

[11] Patent Number: 5,994,629
[45] Date of Patent: *Nov. 30, 1999

[54] POSITIVE SELECTION

[75] Inventors: Kirsten Bojsen, Alleroed; Iain Donaldson, Tinglev; Anna Haldrup, Soborg; Morten Joersboe, Nykoebing Falster; Jette D. Kreiberg, Roskilde; John Nielsen, Copenhagen K; Finn T. Okkels, Roskilde; Steen G. Petersen, Rodovre, all of Denmark; Robert J. Whenham, Exeter, United Kingdom

[73] Assignee: Novartis AG, Basel, Switzerland

[*] Notice: This patent is subject to a terminal disclaimer.

[21] Appl. No.: 08/527,474

[22] Filed: Sep. 13, 1995

Related U.S. Application Data

[62] Continuation-in-part of application No. 08/505,302, Oct. 3, 1995, Pat. No. 5,767,378, and application No. 08/378,996, Jan. 27, 1995, abandoned, which is a continuation of application No. 08/196,152, filed as application No. PCT/DK92/00252, Aug. 27, 1992, abandoned.

Foreign Application Priority Data

Aug. 28, 1991 [DK] Denmark .................................. 1522/91
Mar. 2, 1993 [GB] United Kingdom .................... 9304200

[51] Int. Cl.[6] .................. C12N 5/00; C12N 15/00
[52] U.S. Cl. ................ 800/298; 800/278; 800/320.1; 435/419; 435/468

[58] Field of Search .................................. 800/205, 250, 800/DIG. 56; 435/172.3, 412, 419, 430; 935/55, 79

[56] References Cited

FOREIGN PATENT DOCUMENTS

| | | |
|---|---|---|
| 1732188 | 12/1988 | Australia . |
| 0303780 | 5/1988 | European Pat. Off. . |
| 92 919 292 | 1/1998 | European Pat. Off. . |

*Primary Examiner*—Bruce R. Campell
*Attorney, Agent, or Firm*—Thomas Hoxie

[57] ABSTRACT

A method of selecting genetically transformed cells from a population of cells comprising introducing a desired nucleotide sequence and a co-introduced nucleotide sequence into the genome of a cell whereby the desired nucleotide sequence or the co-introduced nucletoide sequence induces a positive effect by giving the transformed cells a competitive advantage when the population of cells are supplied with an inactive compound thereby allowing the transformed cells to be identified and selected from the non-transformed cells by means defined as positive selection; as well as cells transformed according to the method and plants derived therefrom. The invention further relates to novel glucuronide compounds including cytokinin glucuronide compounds for use in the method.

30 Claims, 8 Drawing Sheets

POSITIVE SELECTION

This application is a continuation in part of application Ser. No. 08/378,996, filed Jan. 27, 1995, now abandoned, which is a continuation of application Ser. No. 08/196,152, filed Feb. 23, 1994, now abandoned, which is the National Stage of International Application PCT/DK92/00252, filed Aug. 27, 1992, and application Ser. No. 08/505,302, filed Oct. 3, 1995, U.S. Pat. No. 5,767,378, the specifications of which are hereby incorporated by reference in their entirety.

BACKGROUND OF THE INVENTION

The present invention relates to a method for selecting genetically transformed cells into which a desired nucleotide sequence has been incorporated by providing the transformed cells with a selective advantage without damaging the non-transformed cells, as well as to novel compounds for use in the method, and transformed cells.

It is well known that when new genetic material is to be introduced into a population of cells by transformation, only a certain number of the cells are successfully transformed. It is then necessary to identify the genetically transformed cells so that these cells can be separated from the non-transformed cells of the population. Identification and separation of the transformed cells has traditionally been accomplished using "negative selection", whereby the transformed cells are able to survive and grow, while the non-transformed cells are subjected to growth inhibition or perhaps even killed by a substance which the transformed cells, by virtue of their transformation, are able to tolerate.

For example, when a population of plant cells is transformed, selection of the transformed cells typically takes place using a selection gene which codes for antibiotic or herbicide resistance. The selection gene—which in itself generally has no useful function in the transformed plant (and may in fact be undesirable in the plant) is coupled to or co-introduced with the desired gene to be incorporated into the plant, so that both genes are incorporated into the population of cells, or rather into certain of the cells in the population, since it is difficult, if not impossible, in practice to transform all of the cells. The cells are then cultivated on or in a medium containing the antibiotic or herbicide to which the genetically transformed cells are resistant by virtue of the selection gene, thereby allowing the transformed cells to be identified, since the non-transformed cells—which do not contain the antibiotic or herbicide resistance gene in question—are subjected to growth inhibition or are killed.

These negative selection methods have, however, certain disadvantages. First of all, the non-transformed cells may die because of the presence of antibiotics or herbicides in the growth medium. As a result, when the population of cells is a coherent tissue there is a risk that not only the non-transformed cells but also the transformed cells may die, due to the fact that the death of the non-transformed cells may cut off the supply of nutrients to the transformed cells or because the damaged or dying non-transformed cells may excrete toxic compounds.

Another disadvantage of negative selection is that the presence of an unnecessary gene, for example antibiotic resistance, may be undesirable. There is concern among environmental groups and governmental authorities about whether it is safe to incorporate genes coding for antibiotic resistance into plants and microorganisms. This concern is of particular significance for food plants and for microorganisms which are not designed to be used in a closed environment (e.g. microorganisms for use in agriculture), as well as for microorganisms which are designed for use in a closed environment, but which may accidentally be released therefrom. While these concerns may prove to be unfounded, such concerns may nevertheless lead to government restriction on the use of antibiotic resistance genes in for example plants and it is therefore desirable to develop new methods for selecting genetically transformed cells which are not dependent on such genes.

A further disadvantage of negative selection is that plant tissues or cells treated with toxic substances become more susceptible to bacterial infection. This is a problem when Agrobacterium is used as a transformation vector, because the treated tissues or cells sometimes become overgrown with the bacteria even though antibiotics are used to prevent bacterial growth.

In addition, selection of cells or tissues using negative selection requires precise timing of expression of the introduced genes in relation to the selection process. If the transgenic cells are treated with a toxic compound before the detoxifying gene is expressed or before enough gene products are produced to ameliorate the action of the toxic compound, both the transgenic and the non-transgenic cells will be killed. If selection is performed too late, the selection of transgenic cells or tissues may be hindered by, for example, shoot or callus formation from non-transgenic cells or tissues which forms a barrier to the penetration of the compound used to select the transformed cells.

The above disadvantages are substantially overcome by the method according to the present invention, termed "positive selection" which for the first time makes it possible to identify and select genetically transformed cells without damaging or killing the non-transformed cells in the population and without co-introduction of antibiotic or herbicide resistance genes. In addition to the fact that the need for antibiotic or herbicide resistance genes is eliminated, the positive selection method according to the present invention is often far more efficient than traditional negative selection, and a combination of positive and negative selection gives a selection frequency of transgenic shoots as good as if not higher than that obtained using negative selection alone. Furthermore, the use of positive selection provides the advantage that a single gene may be used as both a reporter gene and a selection gene, resulting in simplification of vector constructions, more stable constructions and a 100% correlation between the expression of reporter and selection genes.

Positive selection may also eliminate the above-mentioned problems with regard to timing, since selective compounds may be produced as a consequence of the action of gene products, resulting from expression of the introduced gene, on particular substrates. Thus, the selective compound may accumulate as a consequence of expression of the selection gene, the selection effect appearing when a sufficient amount of the selective compound has been produced.

SUMMARY OF THE INVENTION

One aspect of the present invention relates to a method of selecting genetically transformed cells from a population of cells comprising
  a) introducing into the genome of a plant cell a desired nucleotide sequence and a co-introduced nucleotide sequence;
  b) obtaining transformed cells;
  c) supplying to the population of cells a compound wherein said transformed cells have a competitive advantage over non-transformed cells due to a positive effect induced by the expression or transcription of the desired nucleotide sequence or the co-introduced nucleotide sequence in the presence of the compound; and d) selecting said transformed cells from the population of cells.

In one embodiment, the desired nucleotide sequence or the co-introduced nucleotide sequence comprises a region which: (a) encodes a protein which is involved in the metabolism of the compound or (b) regulates the activity of a gene encoding the protein or both.

In a second embodiment the population of cells is supplied with at least one inactive compound which is directly or indirectly active in the transformed cells containing the desired nucleotide sequence and is inactive or less active in the nontransformed cells wherein the transformed cells are provided with a competitive advantage.

In another embodiment the competitive advantage is one wherein the expression of the desired nucleotide sequence or the co-introduced nucleotide sequence leads to an increase in the activity of an enzyme found endogenously in the population of cells such that the activity of the enzyme in the transformed cells is greater than the activity of the enzyme in non-transformed cells.

In a further embodiment the competitive advantage is one wherein the expression or transcription of the co-introduced nucleotide sequence or desired nucleotide sequence results in a blockage of the metabolism of the compound supplied to the population of cells or results in a blockage of the synthesis of a compound in the transformed cells.

In still a further embodiment the compound supplied to the population of cells is selected from the group consisting of mannose, xylose, galactose, a derivative or variant thereof and a cytokinin glucuronide.

A further embodiment includes plants derived from the transformed cells selected according to the above recited method. Preferred plants include, potato, sugar beet and maize.

In still another embodiment the invention includes both positive selection and negative selection including the use of a gene coding for antibiotic or herbicide resistance.

In a second aspect the invention relates to genetically transformed cells comprising an exogenous desired nucleotide sequence and a co-introduced nucleotide sequence wherein the co-introduced nucleotide sequence induces a positive effect in the transformed cells and gives said cells a competitive advantage when a population of cells including the transformed cells and nontransformed cells is supplied with a compound and wherein the desired nucleotide sequence codes for a gene other than a toxin, antibiotic or herbicide resistance gene.

In a third aspect the invention includes a method of selecting genetically transformed maize cells from a population of cells comprising a) introducing into the genome of a maize cell a desired nucleotide sequence and a co-introduced nucleotide sequence;

b) obtaining transformed cells;

c) supplying to the population of cells a compound wherein said transformed cells have a competitive advantage over non-transformed cells due to expression or transcription of the desired nucleotide sequence or the co-introduced nucleotide sequence in the presence of the compound; and d) selecting said transformed cells from the population of cells wherein said co-introduced nucleotide sequence comprises a phosphomanno-isomerase or a mannophosphatase and the compound is mannose, a mannose derivative or a mannose precursor.

In a preferred embodiment, the desired nucleotide sequence encodes β-glucuronidase.

In a fourth aspect the invention relates to novel compounds which are suitable for use in the above described method. This aspect relates to a compound of general formula I

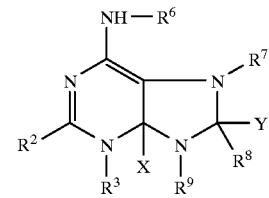

wherein $R^2$ is H, $CH_3$, S—$CH_3$, $SO_2$—$CH_3$, $SCH_2$-phenyl, SH, OH, Cl or a group —S—$R^{10}$, —NH—$R^{10}$ or —O—$R^{10}$ where $R^{10}$ is a β-D-glucopyranuronosyl group or a salt thereof or an ester or amide derivative thereof at the carboxylic acid function, $R^6$ is benzyl which may be substituted on the phenyl ring with OH, $C_{1-6}$alkoxy, halogen, $C_{1-4}$alkyl, $NH_2$ or $CF_3$, or with —O—$R^{10}$, —S—$R^{10}$, or —NH—$R^{10}$, where $R^{10}$ is as defined above; $C_{1-8}$alkyl or $C_{2-8}$alkenyl which may be substituted with from 1 to 3 hydroxy, glucosyloxy or $C_{1-6}$alkoxy groups, with phenyl, and/or with —O—$R^{10}$, —S—$R^{10}$ or —NH—$R^{10}$, where $R^{10}$ is as defined above; esterified $C_{1-6}$alkyl or $C_{2-6}$alkenyl; furfuryl; or cyclohexylureido, phenylureido or tolylureido;

either i)

$R^7$ and Y are half-bonds which together form a bond, ii) one of $R^3$ and $R^9$ is H or a group $R^{10}$ as defined above and the other is a half-bond which together with a half-bond X forms a bond, or $R^9$ is ribosyl, 5'-phosphoribosyl, glucosyl or —$CH_2CH(NH_2)$COOH and $R^3$ is a half-bond which together with the half-bond X forms a bond, and iii) $R^8$ is H, $CH_3$, S—$CH_3$, $SO_2$—$CH_3$, $SCH_2$-phenyl, SH, OH, Cl or a group —S—$R^{10}$ or —NH—$R^{10}$, —O—$R^{10}$, where $R^{10}$ is as defined above, iv) $R^7$ is ribosyl, 5'-phosphoriboxyl or glucosyl, $R^8$ is H, $R^9$ and Y are half-bonds which together form a bond, and $R^3$ is a half-bond which together with the half-bond X forms a bond;

with the proviso that one of $R^2$, $R^3$, $R^6$, $R^8$ and $R^9$ is or comprises β-D-glucopyranuronosyl group, or a salt thereof or an ester or amide derivative thereof at the carboxylic acid function.

A further aspect of the invention relates to additional compounds which may be used in the above method. Thus, the present invention also relates to a compound of the general formula II

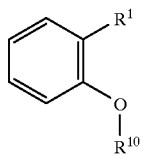

wherein

R¹ is a cis- —CH=CH—COOH, a salt thereof or an ester derivative thereof at the carboxylic acid function, or the amide derivative of cis- and/or trans- —CH=CH—COOH, and R¹⁰ is as defined above.

DETAILED DESCRIPTION OF THE INVENTION

Figure 1:
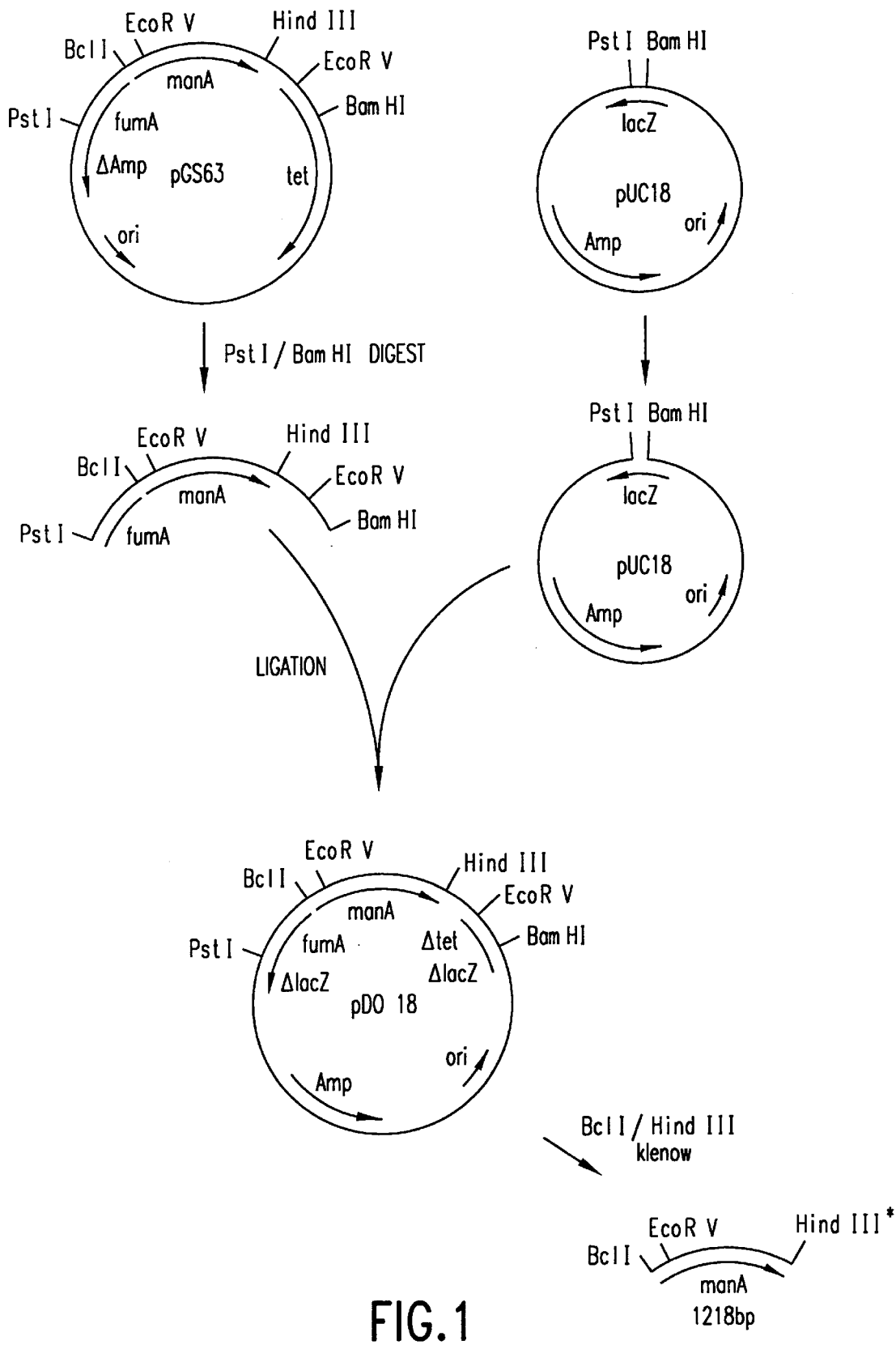
FIG. 1 shows the preparation of a Bcl 1/HindIIII restriction fragment comprising the coding region of the *E. coli*, phosphomannose isomerase.

The term "cells" within the context of the present invention is intended to refer to any type of cells from which individual genetically transformed cells may be identified and isolated using the method of the invention, and includes cells of plants, animals and microorganisms such as bacteria, fungi, yeast, etc. Furthermore, the term cell is includes protoplasts. Particularly preferred cells are plant cells. More particularly the transformed plant cells and plants, seeds or progeny derived therefrom include: fruits such as tomato, mango, peach, apple, pear, strawberry, banana and melon; field crops such as canola, sunflower, tobacco and sugar beet; small grain cereals such as wheat, barley, rice, corn, and cotton; and vegetables crops such as potato, carrot, lettuce, cabbage and onion. Most preferably are sugar beet and corn.

The term "population of cells" refers to any group of cells which has be subjected to genetic transformation. The population may be a tissue, an organ or a portion thereof, a population of individual cells in or on a substrate, for example, a culture of microorganism cells, or a whole organism, for example, an entire plant.

The term "selecting" refers to the process of identifying and/or isolating genetically transformed cells from the non-transformed cells in a population of cells using the method disclosed herein.

The "desired nucleotide sequence" may be any nucleotide sequence which is to be incorporated into the cells to produce genetically transformed cells. Introduction of the nucleotide sequence into plants, microorganisms and animals is widely practiced, and there are no limitations upon the nucleotide sequences whose presence may be detected by use of the positive selection method described herein. By use of this method the presence of the desired nucleotide sequence in the genetically transformed cells may be determined without the above-mentioned disadvantages associated with traditional negative selection systems.

The fact that a desired nucleotide sequence is co-introduced with another nucleotide sequence (referred to as the co-introduced sequence) refers to the fact that the sequences are coupled to each other or otherwise introduced together in such a manner that the presence of the co-introduced nucleotide sequence in a cell indicates that the desired nucleotide sequence has been introduced into the cell. The two nucleotide sequences are typically, although not necessarily, part of the same genetic construct and are introduced by the same vector. A genetic construct containing the two nucleotides sequences will typically, but not necessarily, contain regulatory sequences enabling expression of each nucleotide sequence for example, promoter and transcription terminators.

The desired nucleotide sequence and the co-introduced nucleotide sequence may be introduced independently. The same bacteria may be used for incorporation of both genes and incorporating a relatively large number of copies of the desired nucleotide sequence into the cells, whereby the probability is relatively high that cells which are shown to express the co-introduced nucleotide sequence also will contain and express the desired nucleotide sequence. Independent introduction of two or more genes resulting in co-expression of the genes in the same cell is generally expected to have low probability, and the improved selection frequencies obtained by the positive selection method described herein are therefore expected to be especially advantageous in such systems.

The term "compound" as used herein may be any compound or nutrient in inactive or precursor form (which in the absence of, for example, expression of the co-introduced nucleotide sequence exists in a form which is substantially biologically inactive with respect to the cells in question, but which when the co-introduced nucleotide sequence is expressed or transcribed is hydrolyzed or otherwise activated or metabolized so as to provide the genetically transformed cells containing the desired nucleotide sequence with a selective advantage, and thereby allowing the cells to be selected). The inactive compound may be: an inactive plant growth regulator (for example, an inactivated cytokinin, auxin or gibberellin), a vitamin (for example, inactivated thiamine), a carbohydrate (for example, mannose when the co-introduced nucleotide sequence encodes mannose-6-phosphate isomerase, or xylose, when the sequence encodes xylose isomerase, or galactose or galactose containing compound when the co-introduced nucleotide sequence encodes UDP-galactose-4-epimerase), a nitrogen containing compound (for example, an opine when the co-introduced nucleotide sequence encodes an opine metabolism or transport enzyme), a starch, a protein or another nutrient in inactive form or a compound which has an essential function during differentiation and dedifferentiation of cells and tissues. Treatment of cells and tissues with compounds inducing dependence on supplementary addition of essential compounds may also be used together with the corresponding inactive compounds. This approach may for example be used when sterols or saponins are added. The inactive compound may further be a mineral which is chelated and thereby made available for genetically transformed cells.

Preferred inactive compounds include mannose or xylose and derivatives or precursors thereof or a substrate of the protein with the proviso that the compound is not mannose when the protein is mannose-6-phosphate isomerase. By "derivative" of mannose or xylose is meant any compound capable of being utilized by, binding to, being a substrate for, or a product of any protein involved, either directly or indirectly, in the metabolism of mannose or xylose. In the case of mannose, it will be appreciated that such derivatives include carbohydrates, such as glucose or galactose which may be subject to the actions of epimerases thereby yielding mannose or derivatives thereof. "Derivative" also includes mannose or xylose residues having one or more hydroxyl groups to which residues are covalently or ionically attached. Such attached residues include esters, ethers, amino groups, amido groups, phosphate groups, sulfate groups, carboxyl groups, carboxy-alkyl groups, and combinations thereof. Mannose or xylose derivatives may also include mannose or xylose precursors, if the derivatizations are capable of being removed in such a way as to yield mannose or xylose. A particular mannose derivative is for example mannose 6 phosphate, and a particular xylose derivative is for example a xylose phosphate.

The inactive compound used in the invention need not be one which is activated directly by a polypeptide encoded by the co-introduced nucleotide sequence. It may be activated indirectly, for example whereby the co-introduced sequence has an indirect effect upon the inactive compound in genetically transformed cells but not in non-transformed cells. thus the co-introduced nucleotide sequence may be one which upon expression in the transformed cells for example indirectly increases the activity of an enzyme which is endogenous to the population of cells, thereby leading to a greater enzyme activity and activation of the compound in question in the genetically transformed cells.

The term "competitive advantage" as used herein includes the terms selective, metabolic and physiological advantage and means that the transformed cells inter alia are able to grow more quickly than disadvantaged (non-transformed) cells, or are advantageously able to utilize substrates (such as nutrient precursors, etc.) which disadvantaged cells are not able to utilize, or are able to detoxify substrates which are toxic or otherwise growth inhibitory to disadvantaged cells or a combination thereof. However, the non-transformed cells do not suffer any severe disadvantage in the sense of being damaged or killed or as is the case with negative selection using antibiotics or herbicides, and therefore the term positive selection is used for the disclosed method of selecting transformed cells because the co-introduced sequence either directly or indirectly causing the production or increase of a positive effect of an added compound on the transformed cells.

Therefore the positive selection as used in the context of the present invention refers to the use of a co-introduced nucleotide sequence which serves as a selection gene which produces or increases a positive effect of an added compound on the transformed cells.

A protein which is "involved in the metabolism of a compound" is typically, but not exclusively, an enzyme which may be responsible directly or indirectly for the production or utilization of the compound or its derivatives or precursors. The protein may also be involved in the metabolism of a compound if it binds to it, transfers it from one site to another within the cell or tissue or organism or otherwise sequesters it thereby altering its local availability.

A region of nucleotide sequence which "regulates the activity of a gene encoding a protein" may alter the level of expression of an endogenous gene by being a promoter, or having a promoter activity therefor, and by being introduced in or near its vicinity. By "near" is meant up to 10,000 kb. Alternatively, indirect regulation may arise by altering the binding of RNA polymerase to the promoter of a structural gene encoding a protein, or complementary binding of the nucleotide sequence to at least a part of the structural gene, thus typically reducing the quantity of the protein in the cell.

Use of the present positive selection method in vivo is of particular relevance, for example, in connection with transformation performed on whole plants or on plant parts, in which the plants or parts comprise both transformed and non-transformed cells, since selection of the transformed cells is achieved without directly damaging the neighboring non-transformed cells. The transformed cells thus have a selective "advantage" compared to the non-transformed cells (e.g. the ability to form shoots), but the non-transformed cells do not suffer any severe disadvantage in the sense of being damaged or killed, as in the case with negative selection using antibiotics or herbicides.

The "selective advantage" possessed by the transformed cells may typically be a difference or advantage allowing the transformed cells to be identified by simple visual means, i.e. without the use of a separate assay to determine the presence of a marker gene.

A population of cells may be cultivated on or in a medium containing at least one compound which may be inactive and which is directly or indirectly activated in the transformed cells, the compound being inactive in non-transformed cells or less active in non-transformed cells than in transformed cells, such that the transformed cells are provided with a selective advantage allowing them to be selected from the cell population.

The population of cells may also be cultivated on or in a medium containing a compound which is made available for the transformed cells by expression or transcription of the nucleotide sequence, the compound not being available for the non-transformed cells or being less available for non-transformed cells, such that the transformed cells are provided with a selective advantage.

The cells may also be transformed with a co-introduced nucleotide sequence which may encode a permease or other transport factor which allows the compound to cross the cell membrane and enter the transformed cells or to cross another (organelle) membrane, so that "activation" of an inactive compound involves selective uptake of the compound by transformed cells, and uptake by non-transformed cells is not possible or takes place to a lesser extent. Instead of facilitating uptake of a compound into the cell, the co-introduced nucleotide sequence may alternatively direct its product to a compartment in which the inactive compound is located, for example, outside the plasma membrane or into the vacuole or the endoplasmic reticulum.

A compound used for selection purposes may in addition have both a positive and a negative effect. For example, mannose in sufficiently high concentrations is toxic to most plants, but in cells containing mannose metabolizing enzymes, the negative effect is eliminated and the cells further obtain the benefit of being able to use mannose as a carbohydrate source. In this case a single compound and a single gene together provide a combined positive and negative selection system, although such a system may also be established using two or more genes which together are responsible for inhibition of the negative effects of a compound and manifestation of the positive effects of the compound in the transformed cells.

The cells may be transformed with any nucleotide sequence which it is desired to incorporate therein to. Such a nucleotide sequence may encode genes providing for viral, fungal, bacterial or nematode resistance.

The protein encoded by the desired nucleotide sequence or co-introduced nucleotide sequence is preferably an enzyme involved in mannose or xylose metabolism. Such enzymes include xyloisomerases and phosphomannoisomerases such as mannose 6 phosphate isomerase and mannose 1 phosphate isomerase; phosphomanno mutase; mannose epimerases such as those which convert carbohydrates to mannose or mannose to carbohydrates such as glucose or galactose; phosphatases such as mannose 6 phosphatase and mannose 1 phosphatase, and permeases which are involved in the transport of mannose, or a derivative, or a precursor thereof into the cell.

The agent which reduces the toxicity of the compound to the cells is typically a glucose derivative such as a methyl-3-0-glucose or phloridzin.

Examples of compounds which can exert a physiological effect upon entering the cell, but which are not easily taken up into the cell or a cell compartment, are strongly hydrophilic or hydrophobic compounds, in particular charged compounds, large molecules such as polymers, in particular proteins, peptides, oligo- and polysaccharides, including plant hormones, phosphorylated metabolites such as phosphorylated carbohydrates, phosphorylated vitamins, phosphorylated nucleosides, including cytokinins, and compounds which are conjugated to carboxylic acid-containing carbohydrates or amino acids, including plant hormone conjugates.

Also, it is contemplated that the basic method of the present invention may be modified so that, instead of activating an inactive compound or nutrient in the transformed cells, selection may be performed by blocking the metabolism synthesis of a compound in these cells. For example, the metabolism of a cytokinin added to the substrate may be blocked in the transformed cells by an anti-sense mechanism. The present inventors have thus found that when glycosylation of zeatin is inhibited, the optimal shoot inducing concentration is lowered by a factor of 5–100. By inhibiting the zeatin metabolism, it is thus possible to obtain shoot formation from tobacco leaf discs at zeatin concentrations that are not able to induce shoot formation in non-transformed leaf discs having the normal zeatin metabolism. It has also been found that the effects of indole acetic acid (IAA) can be increased when the metabolism of this compound is inhibited, it was found that the effect of IAA on callus growth was increased by a factor of 5–100. Similarly, the inhibition of carbohydrate and polysaccharide metabolism may affect the utilization of an added carbohydrate and provide additional possibilities for positive selection in this manner.

When a polypeptide encoded by the co-introduced nucleotide sequence or the desired nucleotide sequence directly activates an inactive compound or nutrient in the transformed cells, the non-transformed cells may in certain cases contain or produce a certain amount of the polypeptide in question. For example, when the activating polypeptide is an enzyme, the non-transformed cells may contain a certain native enzyme activity, the native enzyme being of the same type as the introduced activating enzyme. In such cases the "inactive compound or nutrient" need not necessarily be completely inactive in the non-transformed cells, since it may be sufficient that the compound or nutrient is merely substantially less active in non-transformed cells than in transformed cells. In other words, a qualitative difference between the transformed cells and the non-transformed cells with regard to activation of the initially inactive compound or nutrient may in certain cases be sufficient for selection purposes. In such cases inhibitors or substrates which compete with the native enzymes may be added. Especially suitable are inhibitors activated by the native enzyme, resulting in self-catalyzed production of the active inhibitor to a level at which the native enzyme is substantially totally inhibited.

One enzyme which has been found to be suitable for the selection of geneticaly transformed plant cells is β-glucuronidase (GUS), the selection being carried out is one which is cleaved by β-glucuronidase, the basic method may be modified by various means to produced a better result. One of these means is the use of certain sterol glucuronide compounds, e.g. cholesteryl-β-D-glucuronide or β-sitosteryl-β-D-glucuronide, together with a sterol synthesis inhibiting compound such as tridemorph (4-tridecyl-2,6-dimethyl morpholine). Examples 5 and 6 below describe the use of such compounds. It is believed that by using a sterol synthesis inhibitor together with sterol glucuronides which counteract the effect of the sterol synthesis inhibitor upon hydrolysis by β-glucuronidase, so-called "cross feeding" (i.e. diffusion of the activated compound from the cell in which it is activated to another cell) during the selection process may be prevented, since the sterol compounds do not diffuse from cell to cell when the hydrophilic glucuronide moiety is cleaved off. Thus, a more localized effect is obtained. Corresponding results may be obtained with a large number of other glucuronides which contain a hydrophobic aglycone.

It has been found, contrary to early reports that higher plants in fact possess native GUS activity. For this reason, the mere introduction of a GUS gene into a plant may not necessarily be sufficient to obtain the desired selection of the genetically transformed cells, and it may be necessary or desirable to reduce any native β-glucuronidase activity in the population of cells. Since an introduced β-glucuronidase may have different properties than a native β-glucuronidase, a reduction of any native β-glucuronidase activity may be accomplished in different ways, e.g. by addition to the culture medium of a β-glucuronidase inhibiting compound having more of an inhibiting effect on the native β-glucuronidase than on the β-glucuronidase encoded by the nucleotide or subsequence thereof. One such type of compound is ammonium salt.

Native β-glucuronidase activity in the population of cells may also be substantially reduced by addition to the culture medium of a compound which upon hydrolysis results in a product which inhibits the activity of the native β-glucuronidase, and which preferably inhibits the activity of the native β-glucuronidase more than the activity of the introduced β-glucuronidase is inhibited. This may be performed in an autoregulated or localized manner, e.g. localized to specific compartments where the introduced GUS gene is located or is not located. An example of a hydrolysis product which inhibits native β-glucuronidase is a glucuronic acid, e.g. resulting from the hydrolysis of glyccyrrhizic acid or steryl glucuronides.

Native β-glucuronidase activity in the population of cells may further be reduced by addition to the culture medium of a β-glucuronidase inhibitor, in particular a β-glucuronidase which in cells without an introduced β-glucuronidase gene inhibits β-glucuronidase activity more than in cells with an introduced β-glucuronidase gene. This can e.g. be a poor β-glucuronidase substrate (a glucuronide) having a higher affinity for the native β-glucuronidase than for the introduced β-glucuronidase.

β-Glucuronidase encoded by the introduced β-glucuronidase gene used for the purposes of the present invention is active over a relatively broad pH range, while the native β-glucuronidase found in a variety of different plant species is only active within a relatively narrow range of pH values, typically about pH 4–5 (see Example 3 below). Native β-glucuronidase activity may therefore in this case be reduced by addition to the culture medium of a glucuronide which is able to be hydrolyzed by the native β-glucuronidase and which upon hydrolysis results in an increase in pH, e.g. o-coumaryl glucuronide.

Since it has been found that β-glucuronidase native to plants generally is active at a pH of about 4–5, the native β-glucuronidase activity may also be reduced by addition to the culture medium of a pH regulating compound which provides the culture medium with a pH of between about 5.5 and 8.5 preferably between about 6.0 and 8.0, e.g. between about 6.5 and 7.5, or a pH regulating compound which raises the pH in the cells or in compartments of the cells to a pH within these ranges. At these pH values β-glucuronidase encoded by the introduced GUS gene is active but native β-glucuronidase is substantially inactive. An example of a pH regulating compound which may be used is an ammonium salt or ammonium releasing compound, e.g. ammonium nitrate.

Finally, native β-glucuronidase activity may be reduced or substantially eliminated by a physical treatment such as a heat treatment, e.g. using a temperature in the range of 50–65° C. in the form of a short pulse treatment of about 1–2 days before transfer to the selection substrate and/or using a temperature in the range of 30–45° C. during selection (see Example 10).

Genetic transformation of plant cells is often performed using Agrobacterium strains, in particular strains of *Agrobacterium tumifaciens*. It has been found that certain dearmed Agrobacterium strains induce shoot formation due to the production of shoot-inducing substances during co-cultivation, and such strains should normally be avoided when GUS hydrolysis of cytokinin glucuronides is to be employed for the purposes of selection of genetically transformed cells. Thus, genetic transformation of the cells using a cytokinin glucuronide as the inactive compound is preferably performed using an Agrobacterium strain which does not produce cytokinins or other shoot (growth) inducing compounds, or which produces only an insubstantial amount of such compounds, thereby eliminating or substantially reducing induction of shoot growth due to the presence of living bacteria on or in the cells.

The cells may be transformed by bacterium, such as an Agrobacterium species, which is sensitive to the compound so that selection of the transformed cells by the compound has the advantage of reducing the risk of post-transformation infection of the transformed cells by the bacteria. It will be appreciated that the cells may be transformed by any suitable known means including electroporation, micro-injection, use of the micro-projectile gun, and transformation with Ri and Ti plasmids. The transformed cells may, in suitable cases, be regenerated into whole plants in which the recombinant DNA is stably incorporated into the genome.

In certain cases, e.g. when an improved selection frequency is desired, it may be advantageous for the desired nucleotide sequence to be co-introduced with at least two different selection genes. The additional selection gene may be an additional gene coding for an enzyme (or other protein or polypeptide) suitable for positive selection according to the present invention, or it may be a gene coding for an enzyme (or other protein or polypeptide) suitable for traditional negative selection, e.g. coding for resistance to a toxin, antibiotic or herbicide. Thus genetically transformed cells may be selected using a combination of positive selection and negative selection, the desired nucleotide sequence in the genetically transformed cells further being co-introduced with a subsequence coding for resistance to at least one toxin, antibiotic or herbicide, the medium comprising at least one toxic, antibiotic or herbicide to which the transformed cells are resistant.

As mentioned above, one aspect of the present invention relates to genetically transformed cells which have been selected according to the above method, in particular plant cells, as well as plants, progeny or seeds derived from such genetically transformed plant cells. In particular, it is often an advantage that these cells are genetically transformed plant cells whose genome does not contain as a selection marker an introduced (i.e. non-native) nucleotide sequence coding for toxin, antibiotic or herbicide resistance.

Synthesis of compounds of the general formula I according to the invention

Various methods of greater or lesser generality are available for the synthesis of cytokinin glucuronides embraced by the general formula I, and two of what are believed to be best of these methods are described in the following:

A) Oxidation of the corresponding cytokinin D-glucoside

In this approach the —$CH_2OH$ group attached to the pyranose ring of the β-D-glucoside corresponding to the glucuronide in question is oxidized to a carboxyl function under appropriate conditions. Probably the best method of achieving this oxidation reaction in a straightforward and highly selective manner is catalytic oxidation by oxygen, suitably using platinum black or platinum-on-carbon as the catalyst and employing a weakly basic (pH 8–10) aqueous or aqueous alcoholic (such as aqueuos ethanolic) reaction medium; the reaction may suitably be performed at a temperature in the interval 50–100° C. for a period of time of from 2 to 24 hours. Oxidation (generally non-catalytic) by conventional oxidizing agents other than oxygen may also be applicable, but it is anticipated that the resulting oxidation reactions will, in general, give lower yields and be of poorer specificity (i.e. lead to mixtures of oxidation products—particularly unless measures are taken to protect other oxidizable functionalities of the glucoside starting material by the introduction of appropriate protecting groups (vide infra).

An example of the catalytic oxidation approach is provided by Method 1 of Example 1C in the present applicaiton, in which $N^6$-benzyledenine-9-β-D-glucopyranoside (BA9G) is oxidized to $N^6$-benzyladenine-9-β-D-glucopyranosic acid (which is subsequently isolated as the sodium salt) by oxidation with oxygen in the presence of platinum black.

This method appears to be of rather general applicability for the synthesis of cytokinin 9-glucuronides from corresponding 9-glucosides. It has also proved satisfactory for the synthesis of, for example, zeatin-O-glucuronide (Example 1G herein) from the corresponding zeatin-o-glucoside; zeatin-o-glucuronide is an example of a compound of formula I according to the invention in which the glucuronide moiety is a substitutent on an $R^6$ moiety, as defined herein, of the $C_{2-8}$alkenyl type, and the method in question is believed to be of rather broad generality for other cytokinin glucuronides according to the invention in which an o-glucuronide moiety resides as a substituent on an $R^6$ group which is one of the following types as defined in connection with the general formula I; a benzyl group; a $C_{1-8}$alkyl or substituted $C_{1-8}$alkyl; or a $C_{2-8}$alkenyl or substituted $C_{2-8}$alkenyl.

This approach does not, however, appear to be generally applicable, for example to the synthesis of cytokinin 3-glucuronides.

As already indicated, it is clear that when applying an approach involving oxidation of a cytokinin glucoside, any other oxidizable (under the oxidation conditions in question) functional groups which may be present in the starting cytokinin glucoside and which are to remain unchanged in the final glucuronide of formula I must be protected by the prior establishment of suitable protecting groups. Examples of potentially oxidizable groups which may be present in compounds within the definition of formula I are with reference to their positioning as specificed in connection with the general formula I (vide supra)]: an —SH group which may be present as an $R^2$ and/or $R^8$ group, hydroxy or glucosyloxy groups which may be present as substituents on $R^6$ groups of the substituted $C_{1-8}$alkyl type or substituted $C_{2-8}$alkenyl type; and ribosyl, 5'-phosphoriboxyl or glucosyl groups which may be present as $R^9$ or $R^7$ groups. If,for example, it is necessary to protect aliphatic (alcoholic) hydroxy groups, such as hydroxy groups on secondary carbon atoms in ribosyl, 5'-phosphoriboxyl or glucosyl groups, suitable protecting groups will often be, e.g., acetyl groups which may be introduced by methods which will be well known to a person skilled in the art and which may be removed, after the oxidation process, by alkaline hydrolysis.

However, when using the mild catalytic oxidaiton approach described above, hydrdoxy groups on primary aliphatic carbon atoms are, in general, susceptible to oxidation, while hydroxy groups on secondary (and tertiary) carbon atoms generally are not; thus in oxidizing the —CH$_2$OH moiety in the 5-position of the glucopyranose ring of a cytokinin β-D-glucoside in this manner, the hydroxy groups at the 2-, 3- and 4-positions of the glucopyranose ring generally will not require protection. An —SH group which is to be present as a group $R^2$ and $R^8$ will, however, generally require protection during this catalytic oxidation, and such an —SH group may suitably be protected as the benzyl derivative (vide infra in connection with method B described below).

Numerous appropriate cytokinin glucosides for use as starting materials in this method are commercially available; for example, a wide variety of these are obtainable from Apex Organics Ltd., Leicester, England, and some cytokinin 9-glucosides are obtainable from Sigma Chemical Company, P.O. Box 14508, St. Louis, Mo. 63178, U.S.A. Cytokinin glucosides may also be prepared by established methods reported in the literature. For example, the synthesis of avariety of appropriate cytokinin 9-glucosides having $R^6$ groups embraced within the present definition thereof may be achieved by straightforward extension of the method reported by Cowley et al. [*Aust. J. Chem.* 31 (1978) 1095] for the syntehsis of 9-β-D-glucopyranosides of zeatin and $N^6$-benzyladenine.

B) Syntheses of the Koenigs-Knorr type

This approach, which is based on the original method of W. Koenigs and E. Knorr (*Chem. Ber.* 34 (1901) 957), involves the reaction of methyl(2,3,4-tri-o-acetyl-α-D-glucopyranoxyl bromide)uronate (abbreviated MBTG; a suitable method for the preparation thereof is described by Bollenback et al., *J. Amer. Chem. Soc.* 77 (1955) 3310) with an alcoholic or phenolic hydroxy group, a mercapto (—SH) group or a ring nitrogen atom in an aromatic or unsaturated heterocyclic moiety.

This approach probably provides the most generally applicable method for the synthesis of cytokinin glucuronides according to the invention (or of glucuronides of precursors which may subsequently readily be converted to the desired cytokinin glucuronides), starting from appropriate cytokinins (or cytokinin precursors (vide infra)]l, and it is believed to be of very broad applicability in the preparation of compounds embraced within the general formula I.

The general procedure is as follows: The appropriate cytokinin or cytokinin precursor (vide infra), dissolved in a solvent such as N,N-dimethylformamide (DMF), quinoline, propylene carbonate, methanol or diethyl ether, is allowed to react with a 1.25–2 molar equivalents of MBTG at a temperature in the range of 25–100° C. for a period of from 3 to 96 hours, preferably in the presence of an added halide (bromide) scavenger such as silver oxide or silver carbonate (when employing for example DMF as a solvent, the solvent itself often functions adequately as halide scavenger, in which case the addition of a further scavenger is not essential). This reaction yields the methyl ester of the intermediate peracetylated glucuronide, which is generally isolated and purfied; this may suitable be accomplished, for example, (i) by evaporation of the solvent, followed by extraction of the residue with a solvent such as chloroform, removal of the latter solvent from the extract, and purification of the resulting crude intermediate by recrystallization and/or conventional column chromatographic techniques; or, for example, (ii) by separation of the intermediate from the reaction mixture by conventional column chromatography carried out directly on the reaction mixture, followed by removal of the elution solvent from the eluted fraction(s) of interest and recrystallization of the crude product.

In cases where the desired end-product of formula I is to have the glucuronide moiety in the amide (glucuronamide) form, conversion of the peracetylated methyl ester form of the glucuronide moiety to the amide form is suitably carried out at this stage, and this may generally be accomplished by treating the peractylated methyl ester (preferably purified, e.g. in the manner outlined above) with a solution of anhydrous ammonia in anhydrous methanol at low temperature, e.g. a temperature between 0° C. and −10° C., or, as an alternative possibility, with a concentrated (suitably saturated) aqueous solution of ammonia at approximately ambient temperature, for a period of 0.5–4 hours. The glucuronamide may then be isolated by evaporation of the ammonia solution, e.g. under vacuum, and recrystallization from an appropriate solvent or solvent mixture, such as 90% aqueous ethanol. An example of this conversion is provided by Example 1B herein, in which $N^6$-benzyladenine-3-glucuronamide (BA3GNamide) is prepared from the corresponding methyl ester.

Furthermore, in the case of procedures starting with certain types of cytokinin precursors, a chemical transformation which is necessary in order to convert the cytokinin precursor moiety to the appropriate cytokinin moiety may often be performed on the methyl ester before proceeding to liberate the free glucuronide. As an example, the synthesis of cytolinin 9-glucuronides (whose synthesis by a catalytic oxidative approach has already been described above) may normally be accomplished satisfactorily starting from a substituted or unsubstituted purine having a chlorine atom in the 6-position; the latter 6-chloro compound may, in general, be converted to the methyl ester of the corresponding peractylated 9-glucuronide by means of the above-described general procedure using MBTG, and the 6-chloro group may then be suitably converted to the desired —NH—$R^6$ moiety by allowing the product from the latter reaction to react with the corresponding amine ($R^6$—$NH_2$), which generally may suitably be generated in situ from the amine hydrochloride ($R^6$—$NH_2$.HCl) and an excess (suitably a 2–4 fold molar excess) of an appropriate base, e.g. a tertiary aliphatic amine such as triethylamine in a suitable polar solvent, such as a $C_{1-4}$aliphatic alcohol, at a temperature in the range of 65–120° C. This is illustrated by Method 2 of Example 1C herein, in which the synthesis of $N^6$-benzyladenine-9-glucuronide (BA9GN) (as its sodium salt) by this method is described.

The acetyl groups on the glucuronide moiety are then removed by base hydrolysis using a base such as aqueous sodium hydroxide, aqueous methanolic or ethanolic sodium hydroxide, or methanolic ammonia at a temperature in the range 0–25° C. for a period of from 0.5 to 6 hours. Using a base such as one of the above-mentioned aqueous or alcoholic sodium hydroxide solutions, this procedure gives, after neutralization of the excess of base, the salt form of the corresponding cytokinin glucuronide, whereas the use of a reagent such as methanolic ammonia and subsequent removal of excess ammonia by evaporation leads to the amide form of the glucuronide. The latter is suitably purified by conventional means, such as chromatography, particularly reverse-phasae chromatography, and/or recrystallization from a suitable solvent, such as an aqueous organic solvent, e.g. 80–90% aqueous ethanol.

Clearly, if the starting cytokinin or cytokinin precursor contains one or more functionalities which are capable of reaction with MBTG under the reaction conditions in question, and which are to be present unchanged in the final glucuronide of formula I, then such functionalities must be protected by the prior establishement of suitable protecting groups; examples of such reactive functionalities which may be present in starting cytokinins leading to compounds within the definition of formula I are (with reference to their positioning as specified in connection with the general formula I (vida supra)): —OH or —SH present as an $R^2$ group; —OH or —SH present as an $R^8$ group; —OH or —$NH_2$ present as a substitutent on the phenyl ring of an $R^6$ group of the substituted benzyl type; —OH or glucosyloxy groups present as substituent(s) on an $R^6$ group of the substituted $C_{1-8}$alkyl type or substituted $C_{2-8}$alkenyl type, ribosyl, 5'-phosphoriboxyl or glucosyl groups which may be present as $R^9$ and $R^7$ groups; and —$NH_2$ in a —$CH_2CH(NH_2)COOH$ group present as an $R^9$ group.

With respect to protecting groups suitable for protection of the above-mentioned examples of reactive functionalities which may be present in starting cytokinins, an —OH group may generally suitably be protected by the introduction of an acetyl group (vide supra in connection with the oxidative method of preparation of compounds of formula I) so as to form the corresponding acetoxy (—$OOCCH_3$) group. An —SH group may generally very suitably be protected as the benzylthioether (—$SCH_2C_6H_5$) derivative by the introduction of a benzyl group (e.g. by reaction with benzyl chloride in a manner similar to that described in further detail below in connection with cytokinin precursors which contain, at least formally, oxo (=o) or thioxo (=S) groups at the 2-position, and an oxo group at the 6-position (vide infra).) An —$NH_2$ group may generally suitably be protected by conversion to a phthalimido group as follows: the cytokinin or cytokinin precursor is heated with an excess of phthalic anhydride in a relatively inert solvent, such as chloroform or 1,2-dimethoxyethane, at a temperature in the region 70–100° C. for a period of hours, often suitably about 4 hours. The —$NH_2$ group may, after performance of the Koenigs-Knorr type reaciton, subsequently be regenerated by treatment with an aqueous alcoholic (such as an aqueous ethanolic) solution of hydrazine.

A group of cytokinin precursors which are particularly well suited for use in the synthesis of cytokinin glucuronides according to the invention having the glucuronide moiety (corresponding to $R^{10}$ in the general formula I) attached as —O—$R^{10}$ or —S—$R^{10}$ at the 2-position of the purine ring system are cytokinin precursors which contain, at least formally, oxo (=O) or thioxo (+S) groups at the 2-position, and an oxo group at the 6-position; it should be mentioned here that compounds of the types in question having 2-oxo and 2-thioxo groups will, at least in solution, generally be in tautomeric equilibrium with the corresponding 2-hydroxy and 2-mercapto compounds (the 6-oxo group then being present as a 6-hydroxy group), and the latter tautomeric forms will, in general, be present in a significant proportion.

The latter-mentioned hydroxy or mercapto group at the 2-position is converted, in the final phase of the overall synthesis procedure, by means of the Koenigs-Knorr type procedure to the corresponding —O—$R^{10}$ or —S—$R^{10}$ group, respectivley; however, before performing the Koenigs-Knorr type reaction sequence the 6-hydroxy group is suitably converted, via its intermediate conversion to a 6-halo (preferably 6-chloro) group, to the —NH—$R^6$ moiety shown in formula I, and this generally requires that the hydroxy or mercapto group at the 2-position is protected by a suitable protecting group during this conversion sequence. For both these groups, the protecting group of choice is a benzyl group, which may normally be introduced straightforwardly by a reaciton involving the gradual addition of a slight excess of benzyl chloride to a stirred solution or suspension of the cytokinin precursor in question in aqueous based (pH typically about 12–13), such as aqueous sodium or potassium hydroxide, at approximately ambient temperature.

After continued stirring for a period of, typically, 1–2 hours, the reaction mixture is neutralized by addition of, e.g., glacial acetic acid, and the insoluble, benzyl-protected product is isolated by filtration.

The 6-hydroxy group of the resulting 2-benzyloxy- or 2-benzylthio-6-purinol derivative is then converted to a 6-chloro group, suitably using an excess of a chlorinating reagent such as phosphorous oxychloride (phosphoryl chloride) in the presence of an organic base, such as N,N-diethylaniline; the latter reaction will normally suitably be performed under reflux conditions for a period of from about 10 minutes to about 3 hours.

The 6-chloro group may then be suitably converted to the desired —NH—$R^6$ moiety by allowing the product from the latter reaction to react with the corresponding amine, $R^6$—$NH_2$, which generally may suitably be generated in situ from the amine hydrochloride ($R^6$—$NH_2$.HCl) and an excess (suitably a 2–4 fold molar excess) of an appropriate base, e.g. a tertiary aliphatic amine such as triethylamine, in a suitable polar solvent, such as a $C_{1-4}$ aliphatic alcohol (e.g. 1-butanol), at a temperature in the range 65–120° C.

After isolation of the product, the protecting group is removed to regenerate the free 2-hydroxy or 2-mercapto group; in the case of a benzyl protecting group, this may suitably be accomplished, for example, by treatment of the product with an excess of sodium in liquid ammonia.

In the case of products having a 2-mercapto group at this stage, it is believed to be generally advantageous to convert the 2-mercapto group to a salt form (—S⁻), e.g. the potassium salt form, before proceeding to introduce the glucuronide moiety by means of the Koenig-Knorr type procedure described above. An example of a suitable procedure for this purpose is described in step 4 of working Example 1E herein, and the conditions described there are believed to be of rather general applicability. It may, however, in some cases be possible to perform the Koenigs-Knorr type reaciton with MBTG (see below) directly without prior conversion of the 2-mercapto group to the salt form.

Finally, the glucuronide moiety is introduced by reaction with MBTG as described above in connection with the Koenigs-Knorr type procedure.

An example illustrating the sequence of synthesis steps described above is given in Example 1E for the synthesis of the sodium salt of $N^6$-(2'-isopentenyl)adenine-2-thioglucuronide (IP2SGN) starting from 2-thioxanthine, and much of the further information provided therein with regard to choice of recrystallization and extraction solvents, choice of concentrations and amounts of reacgents, etc., is believed to be of more general applicability in performing the sequence of reactions outlined above starting from a cytokinin precursor having a "2-thioxo" group (i.e. a 2-mercapto group) and a "6-oxo" group (i.e. a 6-hydroxy group).

Similarly, a group of cytokinin precursors which are particularly well suited for use in the synthesis of cytokinin glucuronides according to the invention having the glucuronide moiety (corresponding to $R^{10}$ in the general formula I) attached as —O—$R^{10}$ or 8-position of the purine ring system are cytokinin precursors which contain, at least formally (for reasons similar to those outline above in connection with cytokinin precursors having a formal 2-oxo or 2-thioxo group and a formal 6-oxo group), an oxo (═O) or thioxo (═S) group at the 8-position, and which further have a hydroxy group at the 6-position. These may, in general, be converted to the desired end-product of formula I using a sequence of reactions (protection, introduction of a 6-chloro group, introduction of the —N—$R^6$ moiety, deprotection, and finally reaction with MBTG) analogous to that outlined above for cytokinin glucuronides having the glucuronide moiety attached as —O—$R^{10}$ or —S—$R^{10}$ at the 2-position of the purine ring system. An example of this is provided by Example 1F herein for the synthesis of $N^6$-(2'-isopentenyl)adenine-8-thioglucuronide (as the sodim salt thereof).

Compounds of the formula I in which the glucuronide moiety is in the carboxylic acid form may, in general, be prepared from the corresponding salt form, e.g. sodium salt form (prepared in a manner already outlined above) by acidifying a stirred solution or solution/suspension of the salt form in an appropriate solvent (e.g. an aqueous alcohol, such as aqueous ethanol), preferably at a temperature below 25° C., with a mineral acid such as hydrochloric acid to a pH of about 2.5. After stirring for a few minutes, the solvent is then removed under vacuum. The crude residue may advantageously be subjected to a chromatographic treatment to remove inorganic salts (see, e.g., Example 1I herein for details of a typical procedure and a suitable chromatographic substrate for this purpose), after which the product may be recrystallized from an appropriate solvent, typically a polar solvent such as methanol or ethanol.

Compounds of the formula I in which the glucuronide moiety is in the methyl ester or ethyl ester form may generally very suitably be prepared, in high yield, by reaction of the corresponding carboxylic acid form of the cytokinin glucuronide (prepared, for example, as described above) with diazomethane or diazoethane, respectively, using reaction conditions which are normal for this type of reaction and which will be well known to a person skilled in the art.

Numerous cytokinins and cytokinin precursors appropriate for use as starting materials in connection with method B), above, are commercially available, while others may be synthesized by established methods reported in the literature. For example, the synthesis of a variety of appropriate $N^6$-substituted adenines having $R^6$ groups embraced within the present definition thereof may be achieved by literature methods referred to by Iwamure et al. (*Phytochemistry* 19 (1980) 1309), and numerous 2-, 3- and 2,8-substituted $N^6$-(2'-isopentenyl)adenines having $R^2$ and/or $R^8$ groups embraced within the present definition thereof may be prepared as described by Dammann et al. (*Phytochemistry* 13 (1974) 329).

Currently preferred compounds of the formula I are the following:

a compound of formula I wherein $R^2$ is H, $R^3$ is a β-D-glucopyranuronosyl group or a salt thereof at the carboxylic acid function, $R^9$ and X are half-bonds which together form a bond, $R^6$ is benzyl, $R^7$ and Y are half-bonds which together form a bond, and $R^8$ is H;

a compound of formula I wherein $R^2$ is H, $R^3$ is the amide derivative of β-D-glucopyranuronosyl at the carboxylic acid function thereof, $R^9$ and X are half-bonds which together form a bond, $R^6$ is benzyl, $R^7$ and Y are half-bonds which together form a bond, and $R^8$ is H;

a compound of formula I wherein $R^2$ is H, $R^3$ and X are half-bonds which together form a bond, $R^9$ is a β-D-glucopyranuronosyl group or a salt thereof at the carboxylic acid function, $R^6$ is benzyl, $R^7$ and Y are half-bonds which together form a bond, and $R^8$ is H;

a compound of formula I wherein $R^2$ is H, $R^3$ is a β-D-glucopyranuronosyl group or a salt thereof at the carboxylic acid function, $R^9$ and X are half-bonds which together form a bond, $R^6$ is 2-isopentenyl, $R^7$ and Y are half-bonds which together form a bond, and $R^8$ is H;

a compound of formula I wherein $R^2$ is an —S-β-D-glucopyranuronosyl group or a salt thereof at the carboxylic acid function, $R^9$ is H, $R^3$ and X are half-bonds which together form a bond, $R^6$ is 2-isopentenyl, $R^7$ and Y are half-bonds which together form a bond and $R^8$ is H;

a compound of formula I wherein $R^2$ is H, $R^9$ is H, $R^3$ and X are half-bonds which together form a bond, $R^6$ is 2-isopentenyl, $R^7$ and Y are half-bonds which together form a bond, and $R^8$ is an —S-β-D-glucopyranuronosyl group or a salt thereof at the carboxylic acid function; and a compound of formula I wherein $R^2$ is H, $R^3$ and X are half-bonds which together form a bond, $R^9$ is H, $R^6$ is a group of the formula

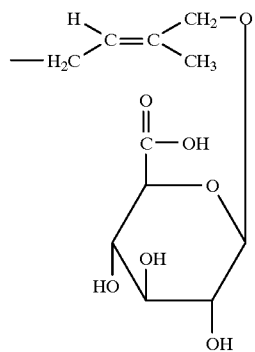

or a salt thereof, $R^7$ and Y are half-bonds which together form a bond, and $R^8$ is H.

Synthesis of compounds of the general formula II according to the invention

Compounds of formula II according to the invention may be prepared straightforwardly using the easily prepared methyl ester of o-coumaric acid (i.e. 3-(2-hydroxyphenyl)-2-propenoic acid) as starting material. The latter ester may be prepared by heating the free acid (obtained, for example, from Aldrich Chemical Company, Gillingham, Dorset, England, under catalogue number H2,280-9) under reflux in methanol in the presence of sulfuric acid. It should be noted here that a mixture of the cis- and trans-forms (with respect to the ethylenic double bond) of the moiety is obtained. It is believed that the trans-form, irrespective of the method of preparation, is generally predominant initially. However, this does not matter, since it has been found that both the cis (coumarinyl) and trans (coumaryl) glucuronides are ultimately converted to coumarin after GUS hydrolysis, due to the fact that coumaric acid is slowly converted (non-enzymatically; presumably via catalysis by light) to coumarin over a period of a few days.

Efficient procedures for the synthesis of the compounds of formula II in which (a) $R^1$ and $R^{10}$ are in the carboxylic acid form and (b) $R^1$ and $R^{10}$ are in the amide form are described in detail in Examples 1H and 1I, respectively, herein. The compound(s) of formula II in which both $R^1$ and $R^{10}$ are in the sodium salt form may suitably be obtained by base hydrolysis of the methyl ester of the peracetylated glucuronide (prepared from methyl o-coumarate) and isolated as in the first part of the synthesis procedure described in Example 1I) using methanolic soidum hydroxide in the manner described in Example 1I; instead of adjusting the pH of the hydrolysate to 2.5 with hydrochloric acid as described in Example 1I, the mixture is merely neutralized (to pH 7) with hydrochloric acid. The sodium salt form is suitably isolated from the mixture by chromatography on, e.g., Amberlite XAD-2 non-ionic resin, the column being washed with water to remove inorganic salts and then eluted with, typically, methanol. The crude glucuronide sodium salt form obtained by removal of the methanol may then suitably be recrystallized from, for example, absolute methanol. The potassium salt form will clearly also be preparable by closely analogous procedure using, e.g., methanolic potassium hydroxide in the hydrolysis procedure.

Compounds of formula II in which both $R^1$ and $R^{10}$ are both in the methyl ester form or both in the ethyl ester form may suitably be prepared by reaction between diazomethane or diazoethane, respectively, and the compound(s) of formula II in which both $R^1$ and $R^{10}$ are in the carboxylic acid form. The reaction conditions herefor will suitably be as described above for the analogous preparation of methyl or ethyl ester forms of cytokinin glucuronides.

Currently preferred compounds of the general formula 11 are the following:

a compound of formula II wherein $R^1$ is cis- and/or trans-2-amidoethenyl (cis- and/or trans-CH=CHCONH$_2$), and $R^{10}$ is the amide derivative of β-D-glucopyranuronosyl at the carboxylic acid function thereof (2-hydroxycinnamyl-β-D-glucopyranuronosyl pyranuroamide);

a compound of formula II wherein $R^1$ is cis-2-carboxy ethenyl (cis-CH=CHCOOH), and $R^{10}$ is a β-D-glucopyranuronosyl group (2-hydroxycinnamyl-β-D-glucopyranuronosyl acid).

The Examples below illustrate the general principles of the present invention in plants, in particular using β-glucuronidase as a selection gene and using novel glucuronide substrates which are able to hydrolyzed by this gene. On the basis of this work, it is contemplated that genes such as the β-glucuronidase gene may be used for a number of related purposes. Thus, the β-glucuronidase gene may be employed in a method for obtaining a localized or tissue specific plant growth regulating effect in a plant part or plant tissue which expresses an introduced β-glucuronidase gene at a higher level than other parts or tissues in the same plant, the method comprising subjecting the plant to a compound which is capable of being hydroyzed by the introduced β-glucuronidase gene, so that the compound is hydrolyzed in the part or tissue containing the introduced β-glucuronidase gene, thereby releasing a growth regulating compound in the tissue and leading to a growth regulating effect only in this part or tissue or leading to a growth regulating effect in this part or tissue which is greater than the effect obtained in other parts or tissues in the plant. It is also contemplated that it may be advantageous to employ plant growth regulators such as cytokinins in the form of glucuronides or glucuronide derivatives rather than as free cytokinins, e.g. in order to take advantage of the fact that they would presumably be transported and distributed differently in plants as compared to e.g. the corresponding free or ribosylated cytokinins.

Similarly, the Examples below suggest certain other uses for β-glucuronidase. One of these is in an in vitro method for screening and identifying cytokinin glucuronide compounds (or glucuronide compounds of other plant growth regulators) which are capable of being hydrolyzed in vivo by an introduced β-glucuronidase gene. β-Glucuronidase may also be used in a system for screening for compounds which are suitable for use as selection agents in the positive selection method disclosed herein (see Example 2). In Examples 3 and 12 systems are described which may be used for screening for compounds which selectively inhibit a native β-glucuronidase enzyme in plant cells without substantially affecting the activity of an enzyme encoded by an introduced β-glucuronidase gene.

The present invention will be still further apparent from a consideration of the following nonlimiting examples.

EXAMPLE 1

SYNTHESIS OF GLUCURONIDE COMPOUNDS

The synthesis of a number of novel glucuronide compounds is described below. In addition to the abbreviations given for each of the individual synthesized compounds, the following abbreviations are used:

BA $N^6$-benzyladenine

AcOH acetic acid

DMF N,N-dimethylformamide

IP $N^6$-(2-isopentenyl)adenine

MBTG methyl(2,3,4-tri-O-acetyl-α-D-glucopyranosyl bromide)uronate

EXAMPLE 1A

3-β-D-glucopyranuronosyl-6-benzylaminopurine, sodium salt

Synonyms: $N^6$-benzyladenine-$N^3$-β-D-glucopyranuronic acid, sodium salt, $N^6$-benzyladenine-3-glucuronide, sodium salt, Abreviation: BA3GN sodium salt

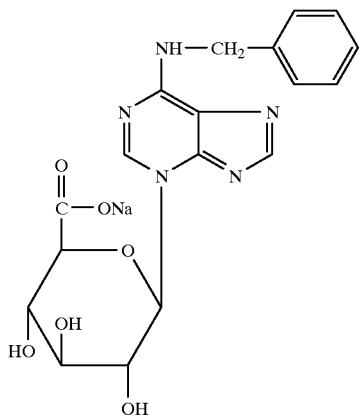

Condensation of $N^6$-benzyladenine (BA) and methyl(2,3,4-tri-o-acetyl-α-D-glucopyranosyl bromide)uronate (MBTG)

BA (12.6 mmole) and MBTG (15.1 mmole) (Bollenback et al., 1955, *J. Amer. Chem. Soc.*, Vol. 77, pp. 3310–3315) are suspended in anhydrous N,N-dimethylformamide (DMF) (50 ml) and heated at 100° for approximately 10 hours. Most of the DMF is removed under vacuum and the crude product is dissolved in chloroform (300 ml) and partitioned with water (3×300 ml). After drying over anhydrous magnesium sulphate the chloroform extract is evaporated under vacuum and a dark syrup is recrystallized from ethanol. The crude product (a mixture of BA, BA9GN and BA3GN as their per-acetylated methyl esters) is purified over 100 g silica packed in chloroform eluted with a gradient of 0–4% ethanol in chloroform. Crude peracetyl BA3GN methyl ester is recrystallized from ethanol. Yield 280 mg of a colorless, amorphous solid.

Peracetyl BA3GN methyl ester is hydrolysed by treatment with 5% sodium hydroxide in 50% aqueous ethanol at room temperature. Five minutes after the solid dissolves the reaction mixture is carefully neutralized with hydrochloric acid while cooling on ice. After drying under vacuum, crude BA3GN sodium salt is purified by reverse-phase chromatography (over 100 g octadecylsilica) eluting with water (1 l) followed by 20% aqeuous methanol followed by recrystallization from ethanol. Pure BA3GN sodium salt (150 mg) is obtained as a colorless, microcrystalline solid which is dried to constant weight over calcium chloride under vacuum.

Analysis
UV

| Ethanol | A max | 297 nm |
| Ethanol/acetic acid | A max | 291 nm |
| Ethanol/ammonia | A max | 297 nm |

These values are identical to the literature values for BA-3-β-glucopyranoside and $N^3$, $N^6$-disubstituted adenine.

(N. J. Leonard, K. L. Carraway and J. P. Helgeson, *J. Heterocyclic Chem.* 1965, 2, 291–297).

HPLC

HPLC is performed using a 10×0.46 cm column of octadecyl silica, eluting isocratically with 60% methanol containing 10% acetic acid at 1 ml/min. UV monitor at 290 nm.

The BA3GN sodium salt has a purity of 95+% and a content of free BA estimated as <0.05%.

Hydrolysis by β-glucuronidase (GUS)

BA3GN sodium salt (500 μg) in 500 μl of 50 mM sodium phosphate buffer, pH 7.0 is incubated with β-glucuronidase (GUS, Sigma Type G7896), 2500 Sigma "Fishman" units for 18 hours at 37° C. HPLC (conditions as above) shows virtually complete removal of the BA3GN peak with the production of a peak which co-chromatographed in 1:1 mixture with authentic BA. This confirms the identity of the product as a conjugate of BA and β-D-glucuronic acid.

The following analysis is obtained for another portion of BA3GN sodium salt prepared as described above:

UV

| Ethanol | A max | 297 nm |

HPLC

15×0.46 cm octadecyl silica, eluted with a gradient of 20–60% methanol/10% acetic acid over 30 min. at 1 ml/min. HPLC purity 99.5%. Free BA content <0.05%.

TLC

Silica developed with 1-butanol/acetic acid/water (12/3/5). TLC purity 99.5%. Free BA content <0.05%.

Hydrolysis by β-glucuronidase (GUS)

BA3GN sodium salt (500 μg) in 500 μl of 50 mM sodium phosphate buffer, pH 7.0 is incubated with β-glucuronidase (GUS), Sigma Type G7896), 2500 Sigma "Fishman" units for 12 hours at 37° C. HPLC and TLC shows virtually complete (>99%) removal of the BA3GN to yield a compound which co-chromatographed in a 1:1 mixture with authentic BA.

EXAMPLE 1B

3-β-D-glucupyranuronamido-6-benzylaminopurine

Synonyms: $N^6$-benzyladenine-$N^3$-β-D-glucopyranuronamide $N^6$-benzyladenine-3-glucuronamide Abbreviation: BA3GNamide

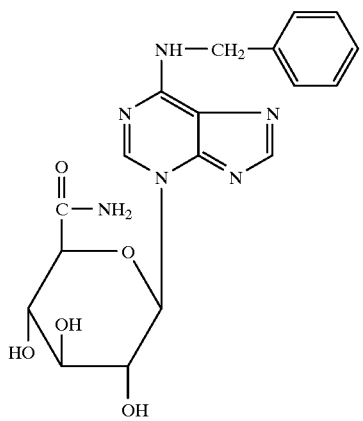

Synthesis

Recrystallized peracetyl BA3GN methyl ester (1.5 g) prepared as in Exampl 1A, is suspended in anhydrous methanol (200 ml) and cooled to 0° C. Further anhydrous methanol (400 ml), saturated with anhydrous ammonia at −10° C., is added and the mixture stirred on ice. Further ice-cold anhydrous methanol is added until the solid dissolved completely. The reaction mixture is stirred on ice for a further 3 h. Excess ammonia and methanol are removed under vacuum and the product is triturated thoroughly with hot ethanol to yield a colorless solid (1.3 g).

BA3GNamide, as with other adenine-3-glycosides, is only sparingly soluble in water or alcohol but dissolves at 2.4 mg/ml in 50% aqueous methanol containing 25% acetic acid.

Analysis

TLC (silica-chloroform/methanol/glacial acetic acid, 50/50/5).

Single UV spot (Rf 0.36) with no detectable impurities at 50 μg loading. Purity 98+%. No detectable (<1%) peracetyl BA3GN methyl ester (Rf 0.89) or BA3GN (Rf 0.02).

TLC (silica chloroform/methanol, 9/1)

Used to test for BA content. BA3GNamide at 192 μg loading showed no detectable 6-benzyl-adenine. BA content therefore <0.2%.

EXAMPLE 1C

9-β-D-glucopyranuronosyl-6-benzylaminopurine, sodium salt

Synonyms: $N^6$-benzyladenine-$N^9$-β-D-glucopyranuronic acid, sodium salt $N^6$-benzyladenine-9-glucuronide, sodium salt Abbreviation: BA9GN sodium salt

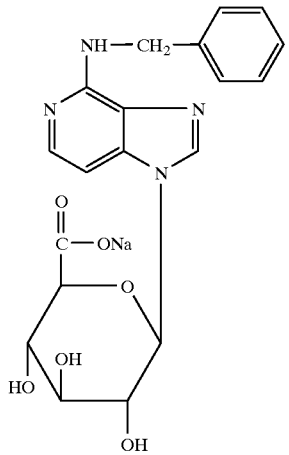

Synthesis
Method 1
Catalytic oxidation of $N^6$-benzyladenine-9-β-D-glucopyranoside (BA9G)

BA9G (50 mg) is suspended in 50 mM sodium bicarbonate (25 ml) with platinum black (200 mg). The mixture is heated at 80° C. on a water bath while oxygen is passed through vigorously. A further 100 mg of platinum catalyst is added after 4 hours. Approximately 95+% of BA9G is converted to the corresponding 9-β-D-glucopyranuronic acid and some BA after 20 hours of treatment. The mixture is neutralized and the product BA9GN sodium salt is purified by reverse-phase chromatography (over 20 g octadecylsilica) eluting with 200 ml water followed by 20% MeOH.

Pure BA9GN sodium salt, free of glucoside and BA, is dried to a colorless solid over calcium chloride under vacuum.

Method 2
Condensation of 6-chloropurine and methyl(2,3,4-tri-o-acetyl-α-D-glucopyranosyl bromide)-uronate (MBTG)

6-Chloropurine (dried over phosphorus pentoxide, 1.13 g), MBTG (3.87 g) and freshly-dried potassium carbonate (1.5 g) are stirred in anhydrous propylene carbonate (30 ml) at room temperature for 24 hours. The dark mixture is filtered and purified by column chromatography over silica 100 g) eluting with a 0–80% gradient of ethyl acetate in chloroform. The main fraction (other than unreacted 6-chlorpurine) is dried and recrystallized from boiling ethanol to yield methyl 6-chloropurine-9-(2',3',4'-tri-O-acetyl-β-D-glucopyranuronate (312 mg) and benzylamine (171 μl) are heated together in 1-butanol (13.5 ml) at 100° C. for 1 hour. The solid dissolves readily to give a clear yellow solution. Most of the butanol is removed under vacuum to yield a whitish solid which is shaken with 5% sodium hydroxide in 50% aqueous ethanol (25 ml) for 1–2 hours at room temperature. After neutralization, the product is dried under vacuum to remove traces of butanol. Crude BA9GN sodium salt is then purified by reverse-phase chromatography as in Method 1.

The pure product is dried under vacuum over calcium chloride and phosphorous pentoxide to yield a colorless solid (210 mg) which co-chromatographed with BA9GN prepared by catalytic oxidation.

Analysis of BA9GN sodium salt prepared by condensation reaction, Method 2
UV

| 95% ethanol | A max | 270 nm | (17,400) |
| 95% ethanol/0.1 M HCL | A max | 270 nm | (16,200) |
| 95% ethanol/0.1 M NaOH | A max | 270 nm | (17,400) |

These results are consistent with the structure of an $N^6$, $N^9$-disubstituted adenine. The extinction coefficients are virtually the same as pure BA9G indicating freedom from non-UV absorbing contaminants. UV purity 95+%.

HPLC

10×0.46 cm octadecylsilica column, UV monitor at 270 nm. Isocratic (50% methanol/0.2M acetic acid, 2 ml/min.) and gradient HPLC (0–60% methanol/0.2M acetic acid, 2 ml/min.) show a sharp, symmetrical peak for BA9GN, which elutes just before the corresponding glucoside. BA9GN prepared by condensation reactioni co-chromatographs in a 1:1 mixture on HPLC (gradient and isocratic) with BA9GN prepared by catalytic oxidation. This confirms that BA9GN prepared by the condensation reaction is the β-D-glucopyranosyl isomer. BA9GN contains no detectable (<2%) α-anomer or other impurities, including BA. HPLC purity of BA9GN 98+%.

TLC (silica-chloroform/methanol, 9/1)

Used to measure BA contamination of BA9GN product. BA9GN does not move from origin in this sytem. Minimum detection limit of BA=200 ng. BA9GN at 200 μg loading shows no detectable BA or other contaminants. TLC purity 98+%. BA content <0.1%.

Acid hydrolysis

Mineral acid converts cytokinin glucosides to the corresponding free cytokinin base. Treatment of BA9GN sodium salt (1 mg/ml) with a 1M hydrochloric acid at 100° C. overnight produces a single spot on TLC which co-chromatographed with authentic BA. This test confirms that BA9GN is an acid-labile conjugate of BA.

Enzymatic hydrolysis

BA9GN sodium salt (500 µg) in 500 µl of 50 mM sodium phosphate buffer, pH 7.0 incubated with Sigma β-glucuronidase (GUS, Type G7896), 2500 "Fishman" units for 18 hours at 37° C. HPLC and TLC shows no detectable production of BA. Further incubation at room temperature for 3 days showed no hydrolysis. BA9GN is therefore not susceptible to β-glucuronidase hydrolysis.

EXAMPLE 1D

3-β-D-glucopyranuronosyl-6-(3-methyl-but-2-enylamino)purine, sodium salt

Synonyms: $N^6$-(2'-isopentenyl)adenine-$N^3$-β-D-glucopyranuronic acid, sodium salt $N^6$-(2'-isopentenyl)adenine-3-glucuronide acid, sodium salt Abbreviation: IP3GN sodium salt

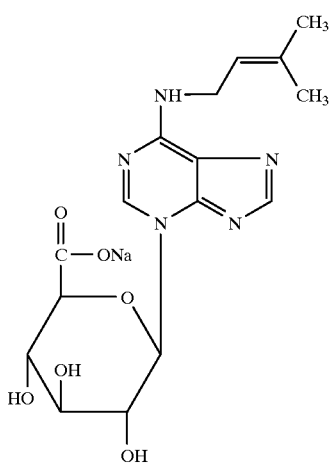

Synthesis $N^6$-(2-Isopentenyl)adenine (9.48 g) and MBTG (22.1 g) are heated in anhydrous DMF (170 ml) at 100° C. for 12 hours. Most of the DMF is removed under vacuum on a boiling water-bath and the cooled syrup taken up in chloroform (500 ml). The chloroform solution is extracted with water (3×500 ml) and the organic extract dried over anhydrous sodium sulphate. Most of the chloroform is removed under vacuum and the syrup chromatographically-purified over silica developed with a gradient of 1 to 3.75% methanol in chloroform. Crude peracetyl IP3GN methyl ester is recrystallized from methanol with charcoal decolorization to yield pure, colorless peracetyl IP3GN methyl ester (3.2 g) which is dried under vacuum over calcium chloride. A portion of peracetyl IP3GN methyl ester (1.2 g) is hydrolyzed by dissolving in approximately 1 l of 75% aqueous methanol containing 5% sodium hydroxide and stirring the mixture for 10 min at room temperature. The mixture is cooled on ice, carefully neutralized with hydrochloric acid and reduced to a syrup under vacuum. The crude product is purified by successive chromatography over XAD-2 resin and octadecyl-silica to yield IP3GN sodium salt as a colorless, microcrystalline solid which is dried over calcium chloride (810 mg).

Analysis

TLC (silica-1-butanol/glacial AcOH/water, 12/3/5)

IP3GN sodium salt gives a single, sharp spot (Rf=0.32) at 100 µg loading with no detectable $N^6$-(2-isopentenyl)adenine (IP) (Rf=0.66) or other contaminants. Purity 99.5+%.

Hydrolysis by β-glucuronidase (GUS)

IP3GN sodium salt (500 µg) in 500 µl of 50 mM sodium phosphate buffer, pH 7.0 is incubated with β-glucuronidase (GUS, Sigma Type G7896), 2500 Sigma "Fishman" units for 12 hours at 37° C. TLC shows removal of the UV spot corresponding to IP3GN with the production of a new UV spot which co-chromatographed with authentic IP.

EXAMPLE 1E 6-(3-methyl-but-2-enylamino)purine-2-yl-1-thio-β-D-glucopyranuronic acid, sodium salt Synonyms: $N^6$-(2'-isopentenyl)adenine-2-thioglycopyranuronic acid, sodium salt $N^6$-(2'-isopentenyl)adenine-2-thioglucuronide acid, sodium salt Abbreviation: IP2S sodium salt

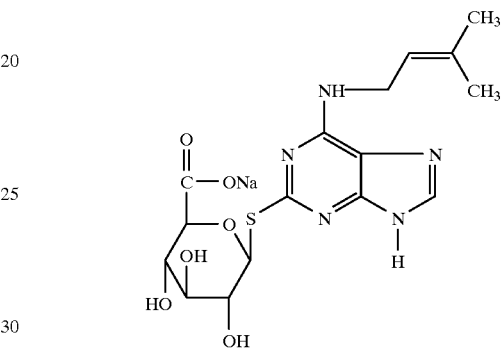

Synthesis 1. 2-Benzylthio-6-purinol

Benzyl chloride (1.4 ml) is added dropwise with vigorous stirring to a solution of 2 g of 2-thioxanthine in 12 ml of 1M sodium hydroxide, diluted to 140 ml with water. After addition is complete a cream-colored precipitate forms. The reaction mixture is stirred for an additional hour at room temperature and filtered. The solid is washed thoroughly with water and dried overnight under vacuum over calcium chloride and to constant weight over phosphoros pentoxide. The crude product (2 g) is used directly in the next step without recrystallization.

2. 2-Benzylthio-6-chloropurine

2-Benzylthio-6-purinol (2 g) is covered with a mixture of phosphorous oxychlofide (20 ml) and diethylaniline (2 ml). The mixture is refluxed with stirring for 1 hour, cooled and poured onto ice (100 g). A yellow precipitate formed which is filtered, washed thoroughly with water and dried under vacuum. The crude product is recrystallized from methanol to yield a light-cream solid (1.2 g) which is dried to constant weight over phosphorous pentoxide.

3. 2-Benzylthio-$N^6$-(2-isopentenyl)adenine

A mixture of 2-benzylthio-6-chloropurine (1.2 g) and isopentenylamine hydrochloride (1.04 g) in 1-butanol (25 ml) containing triethylamine (2.2 ml) is heated in a sealed tube at 110° C. for 2 hours. The butanol is removed under vacuum and the mixture shaken with ice-water (100 ml). The product is filtered recrystallized from ethanol with charcoal decolorization and dried under vacuum with phosphorous pentoxide. Yield 0.64 g. Yield 1.3 g of 2-benzyl-thio-$N^6$-(2-iso-pentyenyl)adenine as a colorless solid. The crude product is used directly in the next step.

4. 2-Thio-$N^6$-(2-isopentenyl)adenine

2-Benzylthio-$N^6$-(2-isopentenyl)adenine (0.64 g) is dissolved in liquid ammonia (62.5 ml) to yield a clear yellow solution. Sodium (approximately 200 mg) is added in small portions until a blue coloration persisted for 10 min. A small amount of solid ammonium chloride is added cautiously to remove excess sodium and the ammonia is allowed to evaporate to a small volume. Diethyl ether (65.5 ml) is added and the ether extract extracted with water (62.5 ml). The aqueous extract is adjusted to between pH 4 and 5 with acetic acid when a creamy solid precipitated. After cooling, the product is filtered off and dried over phosphorouos pentoxide under vacuum. Yield 340 mg.

Crude 2-thio-$N^6$-(2-isopentenyl)adenine is converted to the potassium salt by suspension in water and addition of an equimolar amount of potassium hydroxide together with sufficient alcohol to effect solution. The solution is dried under vacuum and over phosphorous pentoxide.

5. $N^6$-(2-isopentenyl)adenine 2-thioglucopyranuronide

2-Thio-$N^6$-(2-isopentenyl)adenine, potassium salt (2.89 mmole) is dissolved in anhydrous methanol and MBTG (5 mmole) added. The mixture is stirred for 24 hours at room temperature, during which time a creamy white solid is deposited. The reaction mixture is dried under vacuum and hydrolysed at room temperature by treatment with 5% aqueous sodium hydroxide (50 ml) to yield the free glucopyranuronide as the sodium salt. The mixture is neutralized by the careful addition of concentrated hydrochloric acid with external cooling to yield a colorless precipitate of crude IP2SGN sodium salt.

The crude product is purified by reverse-phase chromatography recrystallized from ethanol and dried under vacuum over calcium chloride to yield a colorless, amorphous solid (150 mg) The product is sparingly soluble in 50% aqueous alcohol.

Analysis
UV

| water, pH 1 | A max | 284, 241, 206 nm |
| water, pH 7 | | 278, 230 (shoulder) |
| water, pH 14 | | 283, 227 |

IP2SGN sodium salt shows the characteristic UV spectrum of 2-thio-substituted cytokinins and the spectrum is closely similar to that of authentic 2-methylthio $N^6$-(2-isopentenyl)adenine. UV analysis confirmed the product as a 2-$N^6$-disubstituted adenine.

HPLC

HPLC uses a 15×0.46 cm octadecylsilica column eluted with a gradient of 0–60% methanol containing 0.2M acetic acid over 30 min. At 1 ml/min. UV monitor at 270 nm.

IP2SGN sodium salt has a purity of 98+% and contains no detectable free 2-thio-$N^6$-(2-iso-pentenyl)adenine (<0.1%). Hydrolysis by β-glucuronidasae (GUS)

IP2SGN sodium salt (500 μg) in 500 μl of 50 mM sodium phosphate buffer, pH 7.0 is incubated with β-glucuronidase (GUS, Sigma Type G7896), 2500 Sigma "Fishman" units for 48 hours at 37° C. HPLC (conditions as above) shows partial removal (65%) of IP2SGN to produce a peak which co-chromatographed in a 1:1 mixture with 2-thio-$N^6$-(2-isopentenyl)adenine. This test confirms that identity of IP2SGN sodium salt as a conjugate of 2-thio-$N^6$(2-iospentenyl)-adenine and β-D-glucuronic acid, partially susceptible to GUS hydrolysis.

EXAMPLE 1F 6-(3-methyl-but-2-enylamino)purine-8-yl-1-thio-β-D-glucopyranuronic acid, sodium salt Synonyms: $N^6$-(2'-isopentenyl)adenine-8-thioglucopyranuronic acid, sodium salt $N^6$-(2'-isopentenyl)adenine-8-thioglucuronide acid, sodium salt Abbreviation: IP8SGN sodium salt

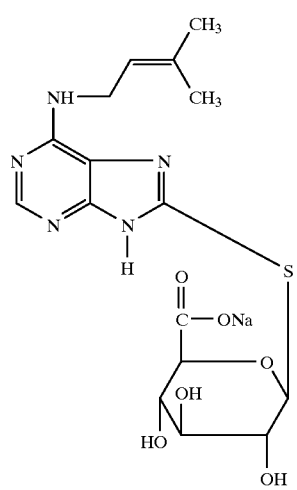

Reaction 1
6-Hydroxy-8-thiopurine
4,5-Diamino-6-hydroxypyrimidine sulphate (25 g) and thiourea (100 g) are ground together and heated on an oil bath to 200° C. for 30 min. The cooled, solidified product is dissolved in hot 1M NaOH (500 ml), boiled with charcoal and filtered. The hot filtrate is acidified with cHCl and the hot solution is filtered to yield a red solid which is reprecipitated from hot basic solution, washed well with water and dried under vacuum at 80° C. Yield 5.28 g.

Analysis
UV

| A max, pH 1 | 236, 292 nm | (lit. 234, 290 nm) |
| pH 11 | 234, 292 nm | (lit. 234, 290 nm) |

Reaction 2
6-Hydroxy-8-benzylthiopurine
5.28 g 6-hydroxy-8-thiopurine is suspended in 78.6 ml of 1M NaOH and diluted to 400 ml with water. 3.7 ml of benzyl chloride is added and the reaction mixture stirred vigorously for 3 hours at room temperature, adjusted to pH 5 with glacial acetic acid and filtered. The product is washed thoroughly with water and dried overnight under vacuum at 80° C. to give 7.33 g of a salmon-pink solid which is used without further purification.

Reaction 3
6-Chloro-8-benzylthiopurine
6-Hydroxy-8-benzylthiopurine (7.33 g) is added to a mixture of phosphorous oxychloride (70 ml) and N,N-diethylaniline (7.5 ml), and the mixture refluxed for 2 hours to give a dark-red product. The mixture is concentrated under vacuum and the resulting syrup poured slowly with stirring onto ice (400 g). The mixture is allowed to stand for 15 min., then made strongly alkaline with cold concentrated KOH. The mixture is triturated thoroughly to dissolve most of the syrup and acidified to pH 1 by the slow addition of cold concentrated HCl, with excess ice still present.

After standing for 1 hour at room temperature, the product is filtered off, washed thoroughly with water and dried under vacuum at 80° C. for 2 hours to give 7.8 g of product.

Reaction 4
8-Benzylthio-$N^6$-(2'-isopentenyl)adenine
A mixture of 6-chloro-8-benzylthiopurine (3.9 g) and isopentenylamine hydrochloride (3.42 g) in 1 butanol (100 ml) containing triethylamine (7.5 ml) is refluxed for 2 hours. Most of the 1-butanol is removed under vacuum and the reaction mixture cooled on ice and shaken with water (400 ml).

After refrigeration overnight, the mixture is filtered to yield a crude product which is purified by chromatography over 100 g silica gel eluted with a gradient of 0–2.5% MeOH in chloroform. The chromatographically pure product is recrystallized from methanol to yield 1.18 g of a colorless, amorphous solid.
Analysis
TLC (silica-2.5% methanol/chloroform)
Purity 98+%. No detectable impurities.
UV

|  |  |
|---|---|
| 95% Ethanol/HCl | 307 nm |
| 95% Ethanol | 291 nm |
| 95% Ethanol/ammonia | 298 nm |

Reaction 5
8-Thio-$N^6$-(2'-isopentenyl)adenine

8-Benzylthio-$N^6$-(2'-isopentenyl)adenine (1.18 g) is dissolved in liquid ammonia (125 ml) to yield a clear yellow solution. Sodium is added in small portions until a blue coloration persisted for 15 min. A small amount of solid ammonium chloride is added cautiously to remove excess sodium. The ammonia is evaporated to a small volume on a hot plate and ether (125 ml) added.

After most of the remaining ammonia has been evolved the ether extract is extracted with water (2×65 ml). The aqueous extract (at pH 12–13) is cooled on ice and adjusted to pH 5 with glacial acetic acid. A creamy white solid precipitated which is filtered, washed thoroughly with water and dried overnight over calcium chloride to yield a virtually white, very light powder. Yield 760 mg.
Note: 8-Thio-$N^6$-(2'-isopentenyl)adenine is readily oxidized in alkaline solution.
Analysis
HPLC (15 cm octadecylsilica, 0–80% methanol/0.2M glacial acetic acid, 30 min., 1 ml/min. UV monitor at 300 nm)
Sharp symmetrical peak with no detectable impurities. Purity 98+%.
UV

|  |  |
|---|---|
| 95% Ethanol/HCl | 245, 307 (sh), 315 nm |
| 95% Ethanol | 241, 305, 313 nm |

Reaction 6
IP8SGN sodium salt
8-Thio-$N^6$-(2'-isopentenyl)adenine (600 mg) is suspended in 50 mM potassium hydroxide, (102 ml) containing 1% 2-mercaptoethanol as an antioxidant. Sufficient ethanol is added to dissolve the solid. The solution is dried under vacuum, over calcium chloride followed by phosphorous pentoxide. The dry product is dissolved in anhydrous methanol (100 ml) containing 2-mercapto-ethanol (50 µl) and MBTG (2 g) was added. The mixture is stirred for 24 hours at room temperature and dried under vacuum over calcium chloride and phosphorous pentoxide. The protected ester is hydrolysed for 1 hour at room temperature in 50 ml 5% sodium hydroxide.

After neutralization with concentrated hydrochloric acid the crude product is purified by reverse-phase and by normal-phase chromatography to yield a colorless solid which is dried to constant weight over calcium chloride. Yield 190 mg.

Analysis of IP8SGN sodium salt
UV

|  |  |  |
|---|---|---|
| A max | Ethanol/pH 1 | 300 nm |
|  | Ethanol/neutral | 285 (pronounced shoulder), 291, 301 nm |
|  | Ethanol/pH 12 | 283 (shoulder), 290, 300 nm |

TLC (silica-chloroform/methanol, 1/1)
IP8SGN sodium salt at loadings of 34, 68, 102 and 134 µg shows a single, sharp spot with no detectable contaminants. Purity 99.5+%. Content of free cytokinin base, 8-thio-$N^6$-(2'isopentenyl)-adenine <0.1%.
HPLC (15 cm octadecylsilica, 0–80% methanol/0.2M glacial acetic acid, 30 min., 1 ml, 300 nm)
Single, broad peak, tR 18.2 min. No contaminants detectable. Purity 99.5+%.
GUS hydrolysis
IP8SGN sodium salt at 1 mg/ml is incubated with 2500 units GUS (Sigma) in 50 mM phosphate buffer, pH at 37° C. for 24 hours. TLC (1/1, methanol/chloroform) shows complete (>95%) conversion of IP8SGN sodium salt to a compound which co-chromatographs with 8-thio-(2'-isopentenyl)adenine. IP8SGN sodium salt is therefore susceptible to GUS hydrolysis.

EXAMPLE 1G

O-β-D-glucopyranuronosylzeatin, sodium salt
Synonyms: zeatin-O-β-D-glucopyranuronic acid, sodium salt zeatin-O-β-D-glucoronide, sodium salt
Abbreviation: ZOGN sodium salt

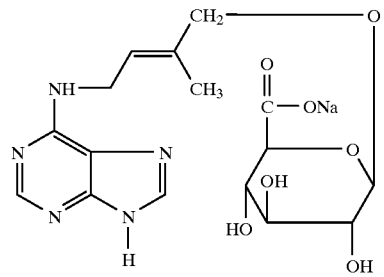

Synthesis
Trans-2-methyl-4-phthalimidobut-2-enyl-(2',3',4')-tri-O-acetyl-β-D-glucopyranuronic acid methyl ester
Trans-1-hydroxy-2-methyl-4-phthalimido-but-2-ene, (1.87 g), (Corse & Kuhnle, 1972, *Synthesis*, pp 618–619) and freshly-activated silver carbonate (9 g) are suspended in anhydrous ether (300 ml) containing molecular sieves (9 g). After stirring for 30 min. at room temperature MBTG (3.24 g) is added and the mixture stirred in the dark for 2 days at room temperature. A further quantity of MBTG (1.62 g) is aded and the mixture stirred for a further 2 days. The reaction mixture is filtered, dried under vacuum to a colorless syrup which is further dried under vacuum over calcium chloride to yield a colorless, powderable foam. The crude product is freed from sugar impurities by chromatography over silica (200 g), eluting with chloroform. Yield of pure product is 2.45 g (55.4%).
Trans-2-methyl-4-amino-but-2-enyl-β-D-glucopyranuronosyluronamide
Methyl trans-2-methyl-4-phthalidmidobut-2-enyl-(2',3', 4')-tri-O-acetyl-β-D-glucopyranuronate (2.45 g) is dissolved in anhydrous methanol (150 ml), cooled on ice, and ammonia passed through the ice-cold solution for 6 hours. After removal of the methanol under vacuum the crude product is purified by chromatography over cellulose (200 g) and developed with butanol-ethanol-acetic acid-water (8:2:1:3 v/v). The eluate is dried under vacuum to yield a brown syrup which is used in the condensation step without further purification.

Zeatin O-β-D-glucuronic acid, sodium salt

The syrup from the previous step is heated in a sealed tupe with 6-chloropurine (0.8 g) and tri-ethylamine (1.5 ml) in methanol (25 ml) at 90° C. for 4 hours to yield the amide. To convert the amide to the acid the methanol is removed under vacuum and 5% aqueous sodium hydroxide (25 ml) is added. After stirring at room temperature for 6 hours the mixture is carefully neutralised with 2M hydrochloric acid and purified by reverse-phase chromatography over octadecylsilica (100 g), eluting with water. Crude ZOGN sodium salt containing unreacted 6-chloropurine, is dried under vacuum and purified by chromatography over silica (50 g) eluting with a 0–100% gradient of methanol in chloroform. After removal of the solvent under vacuum product, as an amorphous solid, is dried under vacuum over calcium chloride. Yield 158 mg.

Analysis

| A max | aq. ethanol | 275 nm, 270 nm (shoulder) |
|---|---|---|
|  | aq. ethanol/HCl | 279 nm |
|  | aq. ethanol/ammonia | 276 nm, 270 nm (shoulder), 283 nm (shoulder) |

TLC (silica-1-butanol/glacial acetic acid/water, 12/3/5)

ZOGN sodium salt at 50 μg loading shows a single spot (Rf 0.16) with no detectable impurities. No zeatin (0.66 or 6-chloropurine (Rf 0.70) is detectable. Overall purity 98+%.
HPLC (15×0.46 cm octadecylsilica column, UV monitor at 270 nm)
Gradient elution (0–100% methanol over 30 min. at 1 ml/min.)

ZOGN sodium salt elutes as a fairly broad peak (tR 10.0 min.) with a small amount of inorganic impurity present with the solvent peak. Overall purity 97+%.
Isocratic elution (50% aqueous methanol, 1 ml/min.)

Isocratic elution is used to measure zeatin content. ZOGN sodium salt has a retention time (tR) of 1.1 min., compared to the authentic trans zeatin tR of 2.2 min. HPLC of up to 96 μg of ZOGN sodium salt showed no detectable zeatin. The zeatin content is therefore <0.1%. This is confirmed by silica gel TLC in chloroform/methanol 9/1. ZOGN sodium salt does not move from the origin in this system, but any contaminating zeatin is clearly separated at Rf 0.39. No zeatin is detected when 200 μg of ZOGN sodium salt is run. The detection limit for trans zeatin on TLC is 200 ng; therefore contamination with trans zeatin is confirmed as <0.1%

Enzymatic hydrolysis

A sample of ZOGN sodium salt is incubated with β-glucuronidasae (Sigma G9387) in 50 mM sodium phosphate buffer at pH 7.0 at 37° C. HPLC (50% isocratic methanol) shows virtually complete conversion to trans zeatin. The identity of trans zeatin in the enzyme hydrolysate is confirmed by co-chromatography at 1:1 mixture of the hydrolysate and authentic trans zeatin in 3 different chromatographic systems.

EXAMPLE 1H 2-hydroxycinnamyl-β-D-glucopyranuronamide
Synonyms: o-coumaryl-β-D-glucopyranuronamide
O-coumaryl glucuronamide Abbreviation: CouGNamide

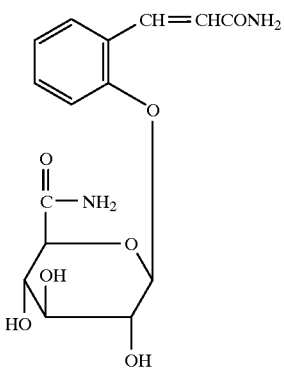

Synthesis

Methyl o-coumarate (15 g) and BTG (16.8 g) are ground together with quinoline (25 ml) to produce an homogenous paste. Silver (I) oxide (10.7 g) is added in portions, with thorough mixing, while the mixture is cooled on ice. After addition is complete the reaction mixture is kept at room temperature for 3 hours. The mixture is extracted with ether (1 l) and the ethere extract washed with water (1 l). The ether extract is dried over anhydrous sodium sulphate and dried to a red syrup under vacuum. The crude syrup is extracted with petroleum ether (300 ml) to remove traces of petroleum ether. The crude product is recrystallized from ethanol with charcoal decolorization to yield pure peracetylated methyl 2-hydroxycinnamyl-O-β-D-glucopyranuronate (3.5 g).

The peracetyl methyl ester (3.5 g) is dissolved in anhydrous methanol (250 ml) and hydrolysed by stirring at 0° C. for 3 hours with further anhydrous methanol (250 ml) which has been saturated with dry ammonia at −10° C. The ammonia and methanol are removed under vacuum and the crude product recrystallized from ethanol and dried under vacuum over calcium chloride to yield pure CouGNamide as a colorless, feathery solid (1.7 g).

Analysis

TLC (silica-chloroform/methanol, 1/1)

Single, sharp spot at Rf 0.63. No contaminants are detected at up to 50 μg loading, purity 98+%. Impurities, less than 0.5% of methyl o-coumarate; or coumarin.

TLC (silica-chloroform/methanol/glacial acetic acid, 50/50/5)

Single, sharp spot at Rf 0.68. Purity 98+%. No detectable (<0.5%) o-coumaric acid (Rf 0.80).

EXAMPLE 1I 2-hydroxycinnamyl-β-D-glucopyranuronic acid

Synonyms: o-coumaryl-β-D-glucopyranuronic acid
o-coumaryl glucuronide

Abbreviation: CouGN

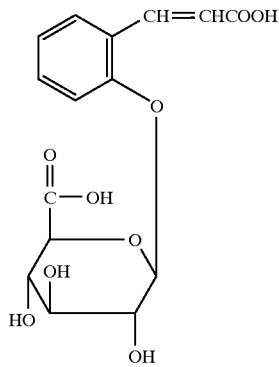

Synthesis

Methyl o-coumarate (17.8 g) and MBTG (20 g) are ground together with quinoline (20 ml) to a uniform paste. Silver (I) oxide (13 g) is added in portions, with thorough mixing, while the mixture was cooled on ice. After addition is complete the reaction mixture is allowed to stand at room temperature for 3 hours. The mixture is extracted with ether (1 l) and the ether extract washed with water (1 l). The ether extract is dried over anhydrous sodium sulphate and dried to a red syrup under vacuum. The crude syrup is extracted with petroleum ether (300 ml) to remove unreacted methyl o-coumarate then dried under vacuum to remove traces of petroleum ether. The crude product is recrystallized from ethanol with charcoal decolorization to yield pure peracetylated methyl CouGN (2.9 g).

The peracetyl methyl ester (2.9 g) is suspended in methanol (250 ml) and 2M sodium hydroxide (250 ml) added with stirring while the reaction mixture is cooled on ice. The mixture is stirred at room temperature for 1.5 hours and adjusted to pH 2.5 with hydrochloric acid. The methanol is removed under vacuum and the crude product purified by XAD-2 chromatography. The chromatographic resin is first washed with water to remove inorganic salts and the product eluted with methanol. After drying under vacuum the product is recrystallized from ethanol and dried under vacuum over calcium chloride to yield pure CouGN as a colorless, amorphous solid (1.5 g).

CouGN is soluble at 5 mg/ml in aqueous buffer, pH 7, and in 50% aqueous alcohol to give a clear, colorless solution.

Analysis

TLC (silica-chloroform/methanol/glacial acetic acid, 50/50/1)

Major spot Rf 0.12 with a minor impurity at Rf 0.24. Purity 90+%. No detectable (<1%) coumarin (Rf 0.90), methyl o-coumarate (Rf 0.91) or o-coumaric acid (Rf 0.80). The major product co-chromatographed with authentic CouGN prepared by the catalytic oxidation of 2-hydroxycinnamyl-O β-D-glucopyranoside.

Gus hydrolysis

CouGN (5 mg) is dissolved in 50 mM sodium phosphate buffer, pH 7.0 (1 ml) and incubated with GUS (1000 units Sigma Type G5897) for 12 hours at 37° C. TLC showed 93.4% conversion to a compound which co-chromatographed with o-coumaric acid. O-coumaric acid is slowly converted (non-enzymatically) to coumarin over a period of a few days.

EXAMPLE 2

CYTOKININ GLUCURONIDES ARE HYDROLYZED BY β-GLUCURONIDASE, RELEASING UNMODIFIED CYTOKININS

An assay is developed to identify those cytokinin glucuronides which can be hydrolyzed by β-glucuronidase from E. coli. (Various features of the β-glucuronidase enzyme and gene are e.g. described in the following: Blanco & Nemoz, Biochemie 69, pp 157–161, 1987; Jefferson et al., Proc. Natl. Acad. Sci. USA 83, pp 8447–8451, 1986; Levvy & Marsh, Advan. Carbohydrate Chem. 14, pp 381–428; U.S. Pat. No. 4,721,671).

The compound to be tested is incubated in 50 mM sodium phosphate buffer, pH 7.0, (generally 500 μg of the compound in 500 μl of the buffer) with β-glucuronidase (generally Sigma type G7896, 2500 Sigma "Fishman" units) for 12–24 hours at 37° C. The presence of hydrolysis products is then determined using HPLC and TLC.

The table below shows the results of the above-described assay on a number of cytokinin-β-D-glucuronidase and a cytokinin-β-D-glucuronamide.

TABLE 1

Cytokinin-β-D-glucuronides (and a cytokinin-β-D-glucuronamide) as substrates β-glucuronidase from E. coli.

| Hydrolysis | Compound |
| --- | --- |
| + | BA3GN sodium salt |
| − | BA3GNamide |
| − | BA9GN sodium salt |
| + | ZOGN sodium salt |
| + | IP3GN sodium salt |
| + | IP2SGN sodium salt |
| + | IP8SGN sodium salt |

Because the only substrates that have been used to assay the GUS enzyme from E. coli in transgenic organisms are O-glucuronides, and because it had been previously reported (Jefferson, "The GUS reporter gene system", Nature Vol. 342, pp 837–838, 1989) that the substrates of β-glucuronidase consist of D-glucuronic acid conjugated through a β-O-glycosidic linkage to an aglycone, it was surprising that certain N-glucuronides and S-glucuronides were also found to be good substrates for this enzyme. It is therefore also contemplated that such N- and S-glucuronide compounds may be used in assays for the β-glucuronidase enzyme from E. coli and plants, e.g. similar to the X-gluc assay referred to below.

In GB 2 197 653 A it is stated that by using the β-glucuronidase system and novel substrates, positive and negative selection using GUS activity may be possible. This hypothesis has, however, never been investigated, and enzymatic hydrolysis of such compounds has never been shown to be probable even on the basis of theoretical considerations regarding chemical characteristics of substrates for β-glucuronidase from E. coli. As shown here, not all glucuronides are substrates for the β-glucuronidase enzyme from E. coli, and it is not expected that most glucuronides are substrates for the GUS enzyme.

Responses in plant tissue expressing the β-glucuronidase gene from E. coli have been used as a method for evaluating whether certain glucuronides (including plant hormone precursors) can be hydrolyzed by the enzyme in vivo (Jefferson, "The GUS gene fusion system as a versatile tool for agricultural molecular biology", abstract from the International Congress on Genetic Manipulation in Plant Breeding held in Elsinore, Denmark, 11–16 September 1988). Unfortunately, this approach is not feasible due to the occurrence of strong endogenous β-glucuronidase activity in plant tissue (See e.g. Example 3 below, as well as Hodal et al., "Detection, expression and specific elimination of endogenous β-glucuronidase activity in transgenic and non-transgenic plants", to be printed in *Plant Science*). The occurrence of this endogenous β-glucuronidase activity also means that by use of the procedure described by Jeffersen, it is impossible to determine whether the effects produced by the glucuronide itself is active. To be a suitable compound for selection purposes, a compound must be activated by the GUS enzyme and also without any significant activity in glucuronide form.

The assay described above can be used to screen for cytokinin glucuronides that are able to hydrolyzed by a given β-glucuronidase enzyme, here exemplified by the β-glucuronidase enzyme from *E. coli*.

It was further determined using HPLC and TLC that unmodified active cytokinins are the product of the GUS hydrolysis (see the above examples relating to the prepartion and analysis of novel cytokinin glucuronide compounds). Thus, it was e.g. found that hydrolysis of BA3GN sodium salt by β-glucuronidase from *E. coli* resulted in virtually complete (>99%) removal of the BA3GN sodium salt to yield a compound which co-chromatographed in a 1:1 mix with authentic BA. Similarly, incubation of ZOGN sodium salt with β-glucuronidase from *E. coli* was shown by HPLC (50% isocratic methanol) to give a virtually complete conversion to trans zeatin; and incubation of IP8SGN sodium salt with β-glucuronidase for 24 hours was shown by TLC (1:1, MeOH/chloroform) to give nearly complete (>95%) conversion of IP8SGN to a compound which co-chromatographs with 8-thio-(2-isopentenyl)adenine.

Similarly, other types of glucuronides may be screened for their ability to be hydrolyzed by a given β-glucuronidase. For example, incubation of o-coumaryl-β-D-glucuronide (5 mg in 1 ml buffer) for 12 hours with β-glucuronidase (Sigma type G5897, 1000 units) was shown by TLC to give a 93.4% conversion to a compound which co-chromatographed with o-coumaric acid. Incubation of the other compounds listed in Table 1 with the exception of the two compounds which did not act as substrates for β-glucuronidase from *E. coli*) gave similar results, i.e. gave hydrolysis products corresponding to those which were to be expected after hydrolysis by β-glucuronidase (see the above examples relating to the preparation of various glucuronide compounds). On the other hand, BA9GN, which as shown above in Table 1 is not a substrate for β-glucuronidase from *E. coli*, and which showed no detectable (<1%) production of BA after incubation for 18 hours at 37° C. with β-glucuronidase, does not induce shoot formation in tobacco leaf discs (Table 2 below).

EXAMPLE 3

INDUCTION OF SHOOT FORMATION FROM PLANT TISSUE WITH AND WITHOUT AN INTRODUCED β-GLUCURONIDASE GENE BY CYTOKININ GLUCURONIDES

Experiments are performed to determine whether cytokinin glucuronides (as well as a cytokinin glucuronamide) are able to induce shoot formation in vivo in plant material with and without, respectively, an introduced β-glucuronidase gene.

Seeds from a GUS-negative and a GUS-positive tobacco plant (*Nicotiana tabacum* 'Wisconsin 38') are germinated on MSO substrate (Murashige & Scoog substrate without hormones, described in Murashige & Skoog, *Physiol. Plant.* 14:473–497,1962, obtainable from Sigma, U.S.A.). The GUS-positive plant material contained in introduced β-glucuronidase gene from *E. coli* (uidA) driven by the 35S promoter from cauliflower mosaic virus as described e.g. by Jefferson et al., *The EMBO Journal* Vol. 16, No. 13, pp 3901–3907,1987. The original transgenic GUS-positive plants are produced using the traditional kanamycin based negative selection system as described e.g. by Burow et al., *Plant Molecular Biology Reporter* Vol. 8(2), pp 124–139, 1990. GUS-positive seedlings are identified using the X-gluc assay as described below in this example.

After 4–5 weeks the upper parts of the plants or shoots are transferred to a new MOS substrate and this procedure is repeated as necessary. In this way the plant material (both GUS-positive and GUS-negative) is maintained as sterile shoot cultures (see Burow et al. *Plant Molecular Biology Reporter*, Vol. 8(2), pp 124–139, 1990). Discs are punched from the largest leaves (3–5 weeks old) and transferred to the substrates indicated below (Table 2). The basic substrate used is MSO, the various test compounds being added at several concentrations up to 250 μM. Small Petri dishes (Ø=5 cm) containing about 6 ml of substrate were used, 3 leaf discs being placed on each Petri dish. Each treatment was repeated at least 4 times.

It was found that several cytokinin glucuronides induce shoot formation in plant tissues containing the β-glucuronidase enzyme. The results are shown in the following table:

TABLE 2

Shoot formation induced by cytokin-β-D-glucuronides (and a cytokinin glucuronamide) on leaf discs of tobacco with (GUS+) or without (GUS−) introduced β-glucuronidase genes.

| GUS− | GUS+ | Compound |
|---|---|---|
| − | − | None (control treatment) |
| + | + | BA (control treatment) |
| + | + | Zeatin (control treatment) |
| − | − | Glucuronic acid (control treatment) |
| + | + | BA3GN sodium salt |
| + | + | BA3GNamide |
| − | − | BA9GN sodium salt |
| + | + | ZOGN sodium salt |
| + | + | IP3GN sodium salt |
| + | + | IP2SGN sodium salt |
| + | + | IP8SGN sodium salt |

"+" means shoot formation at concentrations below 250 μM
"−" means no shoot formation at concentrations below 250 μM
(250 μM corresponds to approximately 100 mg/ml)

It may be seen from the above table that all of the cytokinin glucuronides which induced shoot formation at a concentration of below 250 mM in leaf discs of tobacco containing an introduced β-glucuronidase gene also were able to induce shoot formation using a similar concentration in corresponding leaf discs which did not contain an introduced β-glucuronidase gene. On the other hand, the cytokinin glucuronide BA9GN, which was shown not to act as a substrate for β-glucuronidase from *E. coli* (see Example 2) did not result in shoot formation in leaf discs either with or without an introduced β-glucuronidase gene. However, the cycokinin glucuronamide BA3GNamide, which as shown in Example 2 did not act as a substrate for β-glucuronidase from *E. coli* was found to induce shoot formation in both GUS-positive and GUS-negative leaf discs, indicating that cytokinin glucuronamides are converted to the corresponding cytokinin glucuronic acids in plant tissue. It thus appears that precursors for cytokinin glucuronides can function in vivo in the same manner as the cytokinin glucuronides themselves.

These results indicate that higher plants, in this case tobacco, possess endogenous β-glucuronidase activity. This finding is in accordance with that which has recently been reported by Hu et al. (*Plant Cell Reports* 9, pp 1–5, 1990), who investigated the occurrence of GUS-like activity in 52 species of seed plants, and with the findings of Hodal et al. (to be printed in *Plant Science*). Hu et al. found that species expressing positive GUS-like activities are distributed in every key group of angiosperms as well as in some of the gymnosperms. (While Hu et al. did not detect GUS activity in tobacco, this result may be explained by the fact that their assay was performed in vitro at pH 7. As shown below, the enzyme responsible for the native GUS activity does not appear to be active at pH 7, but has been found to be active at pH 4–5).

These findings are in contrast to that which is disclosed in GB 2197653A, which states that higher plants, including tobacco, contain no detectable β-glucuronidase activity. GB 2197653A, which relates among other things to a method of monitoring expression of a gene of interest using the GUS gene, explains that the presence of GUS activity indicates the expression of the gene of interest and thereby implies that, since GUS activity is not found in higher plants, it is a relatively straightforward matter to monitor the expression of a gene of interest using the GUS gene. However, the above results show that this is not the case, and that the use of a GUS gene to monitor the presence of a gene of interest is not at all simple or straightforward, due to the fact that higher plants do in fact contain a significant intrinsic (background) β-glucuronidase activity.

In order to study the nature of the observed GUS activity in plant material with and without an introduced β-glucuronidase gene, the pH dependency of the GUS activity was determined using a standard histochemical GUS assay with "X-gluc" (5-bromo-4-chloro-3-indolyl-β-glucuronide).

The X-gluc assay may be carried out by first preparing an assay medium by dissolving 50 mg of X-gluc in a solution containing 25 ml 0.2M NaPO$_4$ buffer, typically pH 7.0, 24 ml distilled water, 0.25 ml 0.1M K$_3$(Fe(CN)$_6$), 0.25 ml 0.1K$_4$(Fe(CN)$_6$) and 0.5 ml 1.0M Na$_2$EDTA, followed by stirring until dissolved (about 30 min). Freshly cut or formaldehyde fixed sections (thickness less than 0.5 mm) or tissues at 37° C. are then incubated in the X-gluc medium for from a few minutes to 24 hours. After incubation the sections are rinsed in sodium phosphate buffer or water and examined by microscope. GUS activity is seen as a blue staining of the treated plant material at the site of the enzyme activity (Jefferson, *Plant Molecular Biology Reporter*, Vol. 5, No. 4, pp 387–405, 1987). For the purposes of the present invention assay times of 20 hours were typically used. After incubation the discs were treated with 96% ethanol to remove chlorphyll.

The results are shown in the following table:

TABLE 3 pH-dependency of GUS activity in Tobacco leaf discs with (+) and without (−) introduced GUS genes.

| pH | 3 | 4 | 5 | 6 | 7 | 8 |
|---|---|---|---|---|---|---|
| GUS(−) | 0 | + | + | 0 | 0 | 0 |
| GUS(+) | 0 | + | + | + | + | + |

0: no reaction in X-gluc assay
+: blue reaction in X-gluc assay

It may be seen that the enzyme responsible for the background of β-glucuronidase activity in the tobacco leafa discs without an introduced β-glucuronidase gene is only active within a narrow pH range which corresponds to the internal pH of the plants (about pH 5), while the β-glucuronidase expressed by the introduced gene is active over a wide pH range of from 4 to 8. This pH dependency may explain why previous attempts to detect GUS activity in plants have been largely unsuccessful, leading to the mixtaken conclusion (e.g. in GB 2197653A) that plants do not posses intrinsic GUS activity.

The fact that the β-glucuronidase activity shown above for the plant material without an introduced GUS gene in fact is the result of the hydrolysis of the cytokinin glucuronide substrate by β-glucuronidase, and not a result of a non-specific reaction which cleaves the substrate, e.g. a non-enzymatic acid hydrolysis of glucuronides (which are known to be cleaved at low pH values) was shown by testing the effect of inhibitors of various enzymes at pH 5 in non-genetically transformed plant material (i.e. plant material having only native GUS activity). Testing was performed using the X-gluc assay described above at pH 5.0 for 20 hours.

TABLE 4

Test of inhibitors at pH = 5.0 Non-transformed material

|  | Concentration (mM) | | | | |
|---|---|---|---|---|---|
|  | 0 | 0.1 | 1 | 10 | 50 |
| Saccharo 1,4-lactone | + | + | 0 | 0 | 0 |
| Gluconolactone | + | + | + | + | + |
| UDP-glucuronide | + | + | + | + | + |
| Glucuronic acid | + | + | + | 0 | 0 |
| Galactose | + | + | + | + | + |
| Methylumbellipheryl glucuronide | + | + | + | + | 0 |
| EDTA | + | + | + | + | + |

0 = no reaction, i.e. completely white leaf disc
+ = blue staining with X-gluc

The six inhibitors tested have the following effects:

Saccharo 1,4-lactone is an inhibitor which is specific for β-glucuronidase enzymes (in other words, it inhibits only β-glucuronidase and it inhibits all β-glucuronidases). It is generally accepted that GUS activity which can be inhibited by this compound results from the action of a β-glucuronidase enzyme.

Gluconolactone is an inhibitor of β-glucuronidaseas. It corresponds to saccharo 1,4-lactone, with the exception that it is specific for β-glucuronidases.

UDP-glucuronide is a substrate for UDP-glucuronide transferases.

Glucuronic acid is the product of every β-glucuronidase reaction and therefore a product inhibitor of β-glucuronidases and other glucuronic acid forming enzymes.

Galactose is an inhibitor of UDP-glucuronide-transferase dependent reactions.

Methylumbellipheryl glucuronide is a substrate for all β-glucuronidases thus far investigated and is thus a competitive inhibitor of GUS enzymes.

Since it was also found that EDTA (which inhibits UDP-glucuronide transferases) has no effect, it is unlikely that such transferases are involved in the observed GUS activity. The above table shows that those compounds which should inhibit a transferase enzyme have no effect even at very high concentrations. It may furthermore be seen that gluconolactone has no inhibiting effect, and it is therefore unlikely that the GUS activity is related to a β-glucuronidase activity.

It may further be seen that the GUS specific inhibitor saccharo 1,4-lactone is a strong inhibitor, that glucuronic acid (product inhibition of β-glucuronidase) is a medium strength inhibitor and that methylumbellipheryl glucuronide (a GUS substrate and therefore a competitive substrate to X-gluc if a β-glucuronidase enzyme is responsible for the hydrolysis of X-gluc) is a weak inhibitor. The GUS activity in tobacco therefore fulfills all the necessary criteria to be classified as resulting from a β-glucuronidase enzyme. It may therefore be concluded that the plants contain a β-glucuronidase.

A corresponding series of experiments was performed in order to ascertain whether the effect of the inhibitors was sufficiently fast to be able to inhibit the enzyme. In this series, the plant material was pre-incubated in the test compounds (inhibitors) for 24 hours before the X-gluc assay was performed with the same test compounds. The results obtained were identical to those obtained without pre-incubation, which indicates that the inhibitors penetrate into the plant tissue fast enough to inhibit the X-gluc assay before blue staining can occur.

Results similar to those described above were obtained in another investigation of the occurrence of GUS activity in plants. In this case, the pH dependency of the histological GUS reaction was tested in a number of plant species at pH values between 3 and 8 both without and with the GUS-specific inhibitor saccharo 1,4-lactone.

The assay used was the X-gluc assay described above. The assay was carried out at 37° C. for 20 hours. Leaves were dissected (with sterile razor blades) so that each leaf was tested at a number of different pH values.

As shown by the table below, this investigation confirmed that plants do indeed possess native GUS activity, that this activity is the result of an enzymatic reaction (no reaction in the presence of the GUS-specific inhibitor) and that the enzyme is primarily active at pH values of about 4–5.

TABLE 5

Histological GUS reaction at different pH values

| pH during assay | 3 | 4 | 5 | 6 | 7 | 8 | 3–8 |
|---|---|---|---|---|---|---|---|
| Saccharo 1,4-lactone (mM) | 0 | 0 | 0 | 0 | 0 | 0 | 10 |
| Plant Species | | | | | | | |
| Sugar beet, wild type | + | + | + | + | + | (+) | 0 |
| Sugar beet, transgenic (1) | + | + | + | + | + | + | (+) |
| Sugar beet, transgenic (2) | + | + | + | + | (+) | 0 | 0 |
| Wheat | 0 | + | + | + | 0 | 0 | |
| Wheat, albino | 0 | + | + | + | 0 | 0 | 0 |
| Oilseed rape | + | + | + | (+) | (+) | 0 | 0 |
| Tobacco | 0 | + | + | 0 | 0 | 0 | 0 |
| Tobacco, transgenic(1) | 0 | + | + | + | + | + | 0 |
| Tobacco, transgenic (2) | 0 | + | + | 0 | 0 | 0 | 0 |
| Sitka spruce (4) | 0 | + | + | 0 | 0 | 0 | 0 |
| Rhubarb (3) | n | n | + | + | + | + | 0 |
| Pea (3) | 0 | + | + | 0 | 0 | 0 | 0 |
| Oxalis (3) | n | n | n | n | (+) | n | 0 |
| Chenopodium quonia pollen | n | n | n | 0 | + | n | n |

(1) Leaf tissue expressing the GUS gene from *E. coli*
(2) Transgenic leaf tissue only containing a kanamycin resistance gene (NPT), without an introduced GUS gene
(3) Stem or petiole tissue
(4) Embryogenic callus tissue
+ Blue reaction
(+) Low frequency of GUS activity (faint blue reaction)
0 No reaction
n Not determined The fact that plants have a general intrinsic GUS activity makes it possible to use a gene encoding glucuronide permease as a positive selection gene without the use of any other selection gene by taking advantage of an increased uptake of a glucuronide compound by transformed cells. It has for example been found that glucuronides are not easily taken up into plant cells through plasma membranes. If a glucuronide permease gene is introduced into a cell, however, glucuronides will more readily be able to cross the plasma membrane and enter the cell. The glucuronides will then be available for cleavage by the intrinsic GUS enzyme in the transformed cells. In contrast, the glucuronide in question will not be available for non-transformed cells, whereby a positive selection effect will be achieved. Similarly, positive selection may also be performed using other permeases and other types of compounds which either are activated in the transformed cells by an intrinsic enzyme or which otherwise exert a biological effect in the transformed cells into which they are transported.

EXAMPLE 4

CYTOKININ GLUCURONIDES ARE STABLE AND INACTIVE

The effect of the cytokinin glucuronide BA3GN sodium salt, is blocked when the GUS activity in the plant tissue containing this cytokinin glucuronide is inhibited. In other words, the cytokinin glucuronide is inactive in itself. Furthermore, the cytokinin glucuronide has been shown to be stable in the growth medium as well as in plant tissue when β-glucuronidase is not present, as shown by the fact that the specific GUS inhibitor, saccharo 1,4-lactone (SL) strongly inhibits shoot formation induced by the cytokinin glucuronide BA3GN sodium salt, but only weakly inhibits shoot formation induced by the free cytokinin BA (using the basic method described above in (Example 3):

TABLE 6

Inhibition by (SL) of shoot formation incuded by BA (0.5 mg/l) and BA3GN sodium salt (15 mg/l)

| Treatment | Number and relative number of regenerated Shoots per leaf disc | | | |
|---|---|---|---|---|
| SL (mM) | BA | | BA3GN sodium salt | |
| 0 | 4.3 | 100% | 5.6 | 100% |
| 16 | 3.6 | 84% | 1.4 | 25% |

By comparing the results in the above table with those given above in Table 2, it may be seen that BA3GN sodium salt, which induces shoot formation in both GUS-positive and GUS-negative tobacco leaf discs, does not induce shoot formation in corresponding leaf discs in the presence of the β-glucuronidase specific inhibitor saccharo 1,4-lactone.

Saccharo 1,4-lactone (SL) is not a stable compound at the pH used in this example. An equilibrium exists between SL and saccharic acid (SA). This equilibrium is reached only slowly, and the conversion of SL to SA is followed by a drop in pH. The pH must therefore be adjusted several times during a one week period prior to use of SL until the pH has stabilized in the SL-containing.

The fact that cytokinin glucuronides are stable and inactive when not in the presence of β-glucuronidase is further shown by the fact that BA9GN, which cannot be hydrolyzed by β-glucuronidasae, cannot induce shoot formationi in plant material containing β-glucuronidase activity (see Examples 2 and 3).

It is important that the cytokinin glucuronide compounds are inactive and stable in substrates not containing a β-glucuronidase enzyme, since this stability is a prerequisite for the proper functioning of the positive selection system which uses them.

Not all glucuronic acid derivatives can be expected to be stable, however. For example, ester glucuronides will not be stable in plant tissue which contains non-specific esterases. This means that the cytokinin glucuronide compounds prepared and used according to the present invention (β-D-glucuronides coupled to the aglycon via glyucosidic O, S and N atoms) fulfill the prerequisite for stability. On the other hand, compounds having other types of glucuronide linkages, e.g. amide or ester β-D-glucuronides, are not expected to be selectively hydrolyzed by β-glucuronidases, due to the occurrence of non-specific esterases and amidases in plants.

Referring to Example 3 above, it has thus been shown that the tested cytokinin glucuronides, which as shown in this example do not in themselves possess cytokinin activity, are cleaved in vivo by the action of β-glucuronidase—either in the form of endogenous background β-glucuronidase or as a result of an introduced β-glucuronidase gene—whereby free cytokinin is released.

EXAMPLE 5

INDUCTION OF SHOOT FORMATION FROM PLANT TISSUE CONTAINING AN INTRODUCED β-GLUCURONIDASE GENE USING STEROL-GLUCURONIDES

Other glucuronides, including glucuronides of sterols, glycyrrhizic acid and hydroxyguinoline, have been shown to be hydrolyzed by β-glucuronidase and to result in shoot formation on modified substrates in which the hydrolysis products are essential for shoot formation.

Experiments were performed to determine the shoot inducing effect of two sterol-glucuronides, β-sitosteryl-β-D-glucuronidide (SG) and cholesteryl-β-D-glucuronide (CG), when sterol synthesis is inhibited in the tissues. The basic methods employed correspond essentially to those described for Example 3 above. However, in addition to one or both of the above-metioned sterol-glucuronides, the substrate contained 0.1 mM tridemorph and 5 mg/l BA3GN sodium salt. The number of shoots were registered after 30 days.

Tridemorph (4-tridecyl-2,6-dimethyl morpholine) is a fungicide which inhibits the synthesis of sterols and similar compounds. Tridemorph has an inhibiting effect on shoot regeneration (although not a fatal effect on the explants) when the plant tissue is not supplied with sterols. Thus, in the absence of free sterols, shoot formation should effectively be prevented.

CG was obtained from Sigma, U.S.A., and SG was synthesized according to the procedure described by Ando et al. In *J. Antibiotics* 73, p 408, 1970.

The results obtained are shown in the following table.

TABLE 7

Regenerated shoots per tobacco leaf disc on substrates supplied with tridemorph (0.1 mM) and BA3GN sodium salt (5 mM)

| Compound | Concentration mg/l | | | |
|---|---|---|---|---|
| Sitosteryl-β-D-glucuronide | 0 | 0 | 12.5 | 12.5 |
| Choesteryl-β-D-glucuronide | 0 | 50 | 0 | 50 |
| Shoots per leaf disc | 0.3 | 0.3 | 2.8 | 4.0 |

The above table shows that sitersteryl-β-D-glucuronide is able to counteract the shoot inhibiting effect of tridemorph and that the combination of sitosteryl-β-D-glucuronide and cholesteryl-β-D-glucuronide provides the greatest shoot formation. Thus, positive selection according to the invention using an introduced β-glucuronidase gene is possible using e.g. one or both of the above sterol-glucuronide compounds together with a shoot inhibiting compound such as tridemorph. These results indicate that also other sterols and sterol-like compounds can be used for positive selection from tissue containing an introduced βglucuronidase gene.

An advantage of using these very slightly soluble compounds for positive selection is that their effect will presumably be very local, since the compounds do not diffuse from cell to cell when the hydrophilic glucuronide moiety is cleaved off by a β-glucuronidase enzyme. In other words, these compounds can be used to prevent cross feeding during the selection procedure.

This experiment further indicates that the shoot inhibiting effect of tridemorph, and thus also other compounds which inhibit sterol synthesis, can be counteracted by adding sterols and sterol derivatives to the substrate, whereby a selection system based on providing transgenic cells with sterols and sterol-like compounds can be established with the above-mentioned advantages.

EXAMPLE 6

INDUCTION OF SHOOT FORMATION FROM PLANT TISSUE WITH AND WITHOUT AN INTRODUCED β-GLUCURONIDASE GENE USING SITOSTERYL-β-GLUCURONIDE

An experiment similar to that described in Example 5 was performed on both transformed and non-transformed tobacco leaf discs using sitosteryl-β-glucuronide and either a BA or BA3GN sodium salt.

The methods employed were essentially those described above in Example 5. In this experiment, tridemorph was added to the substrate at a concentration of 0.1 mM and sitosteryl-β-D-glucuronide was added at a concentration of 121 mg/l. The substrate contained in addition either 1.88 mg/l BA3GN sodium salt or 0.1 mg/l BA. The number of shoots was registered after 40 days.

The number of shoots obtained was as follows:

| | Regenerated shoots per leaf disc | | | |
|---|---|---|---|---|
| | BA | | BA3GN Sodium salt | |
| Compound | GUS+ | GUS− | GUS+ | GUS− |
| sitosteryl-β-D-glucuronide | 2.4 | 1.9 | 2.4 | 0.1 |

It may further be seen that, as was the case in Example 5 above, the presence of sitosteryl-β-D-glucuronide was able to counteract the shoot inhibiting effect of tridemorph. Furthermore, when sitosteryl-β-D-glucuronide and tridemorph were used together with BA3GN sodium salt, selective shoot formation was obtained in the GUS-positive leaf discs, while the GUS-negative leaf discs on the substrate containing BA3GN sodium salt had virtually no shoot formation.

These results also indicate that the use of a combination of different glucuronides (here BA3GN and SG instead of BA and SG) may improve the selective response from the transgenic tissues.

Since sterols and steroids are also important growth regulators in animal cells, corresponding selection procedures may also be used for the selection of animal cells which express β-glucuronidase.

EXAMPLE 7

DEARMED AGROBACTERIUM STRAINS PRODUCE CYTOKININS

It has been found that certain Agrobacterium strains induce shoot formation due to production of shoot-inducing substances during co-cultivation. Such strains should normally be avoided when GUS hydrolysis of cytokinin glucuronides is to be employed for the purposes of selection of genetically transformed cells, since these strains alone may induce shoot formation and thereby interfere-with the selection process.

As an example, the table below shows the results of an experiment with two different Agrobacterium strains, one of which induces shoot formation on tobacco leaf discs after co-cultivation.

The methods used correspond essentially to those described in Example 13, but after co-cultivation, the leaf discs were transferred to MSO substrate without hormones containing 300 mg/l cefotaxime and 300 mg/l carbenicillin.

The number of regenerated shoots was registerred 4 weeks after co-cultivation.

TABLE 8

Induction of shoot formation on tobacco leaf discs on a hormone-free substrate after co-cultivation with dearmed Agrobacterium

| Agrobacterium strain | Plasmid | Genes in T-DNA | Number of shoots per leaf disc |
|---|---|---|---|
| 1. C58X | T37 | GUS and NPT | 9.3 |
| 2. LB4404X | PAL4404 | GUS and NPT | 0 |
| 3. C58Y | T37 | None | 4.8 |
| 4. LBA4404Y | PAL4404 | None | 0 |
| 5. None | — | — | 0 |

It is seen that the shoot inducing properties of some of the Agrobacterium strains are not dependent on the genes contained in the T-DNA. This means that genes outside the T-DNA region are responsible for the shoot induction.

A gene outside the T-DNA region responsible for the cytokinin production has been named tzs (Morris, R.O. *Ann. Rev. Plant Physiol.* 37, pp 509–538, 1986). Strain C58 contains the tzs gene, a non-transferable gene which codes for the synthesis of zeatin during co-cultivation. Strain LBA4404 does not cotain the tzs gene. The fact that the shoot-inducing strains contain a plasmid containing the tzs gene indicates that this gene may be responsible for the shoot-inducing properties observed in these investigations and that strains of Agrobacterium containing the tzs gene should be avoided in cytokinin-based selection systems. Any other Agrobacterium strains that induce shoot formation should normally also be avoided.

EXAMPLE 8

POSITIVE SELECTION OF TRANSGENIC SHOOTS USING THE CYTOKININ GLUCURONIDE BA3GN SODIUM SALT

Genetically transformed shoots may be selected using cytokinin glucuronides.

A series of experiments was performed to test the effectiveness of the positive selection system using the cytokinin glucuronide BA3GN sodium salt in concentrations of 7.5 and 15 mg/l. The experiments were performed on wild type tobacco leaf discs using 2 different Agrobacteriums strains as well as various co-cultivation substrates. The transformation method used was that described below in Example 13, with the exception that Gamborg B5 substrate (Gaborg et al., *Exp. Cell Res.* 50:151–158, 1968; obtainable from Sigma, U.S.A.) was used instead of MSO. The results given below are averages based on two independent experiments, each of which was carried out on 27 leaf discs per treatment.

TABLE 9

Positive selection of genetically transformed shoots using the cytokinin glucuronide BA3GN sodium salt.

| Agrobacterium strain | Co-cultivation substrate | GUS+ shoots per leaf disc | % GUS+ shoots among total shoots |
|---|---|---|---|
| 7.5 mg/l BA3GN sodium salt | | | |
| BS10 | B5 | 0.1 | 6.6 |
| BS10 | B5 + ammon. | 0.22 | 0.7 |
| BS10 | B5 + ammon. + SL | 0.3 | 6.1 |
| BS10 | average | 0.1 | 4.4 |
| LDH1 | B5 | 0.2 | 7.8 |
| LDH1 | B5 + ammon. | 0.2 | 5.3 |
| LDH1 | B5 + ammon. + SL | 0.2 | 4.7 |
| LDH1 | average | 0.2 | 5.9 |
| Both | average | 0.2 | 5.1 |
| 15 mg/l BA3GN sodium salt | | | |
| BS10 | B5 | 0.3 | 6.0 |
| BS10 | B5 + ammon. | 0.4 | 8.7 |
| BS10 | B5 + ammon. + SL | 0.3 | 5.5 |
| BS10 | average | 0.3 | 6.7 |
| LDH1 | B5 | 0.4 | 9.0 |
| LDH1 | B5 + ammon. | 0.3 | 7.6 |
| LDH1 | BS + ammon. + SL | 0.3 | 7.7 |
| LDH1 | average | 0.3 | 8.1 |
| Both | average | 0.3 | 7.4 |

B5: Gamborg BS substrate, pH 5.4
Ammon: Co-cultivation substrate with 75 mM ammonium nitrate
SL: Co-cultivation substrate with 25 mM saccharic acid + 25 mM sacchara 1,4-lactone from a stabilized solution
GUS+: Shoots expressing GUS activity when assayed at pH 7 as described in Example 3

Strain BS10 introduces a Gus gene driven by a modified 35S promoter not active in Agrobacterium, as described by Janssen & Gardner in *Plant Molecular Biology*, 14, pp 61–72, 1989. Strain LDH1 introduces a GUS gene driven by the unmodified 35S promoter.

The results in Table 9 show that positive selection of transgenic shoots expressing an introduced β-glucuronidase gene is possible using BA3GN sodium salt. These results are very significant, and were unexpected, since it was found as described in Example 3 that cytokinin glucuronides were able to induce shoot formation in leaf discs not containing an introduced β-glucuronidase gene. The different treatments during co-cultivation do not appear to have any significant effect on selection.

The results shown above indicate also that the use of an Agrobacterium strain with an active β-glucuronidase gene (strain LDH1 expresses GUS activity in bacteria) does not affect the transformation system compared to a strain which does not have an active β-glucuronidase gene (strain BSIO does not express GUS activity in bacteria).

EXAMPLE 9

SELECTION OF GENETICALLY TRANSFORMED SHOOTS USING THE CYTOKININ GLUCURONIDE ZEATIN-o-β-GLUCURONIC ACID

Using essentially the same procedure as described in Example 13 transgenic tobacco shoots were prepared and selected using cytokinin glucuronide zeatin-o-β-glucuronic acid (ZOGN) as the positive selection agent.

Co-cultivation was carried out for 3 days, the inoculum density corresponding to an OD of 1.5 at 660 nm. The substrate used after co-cultivation was MSO containing 300 mg/l carbenicillin, 300 mg/l cefotaxime and 0.1 mg/l indole acetic acid (IAA). Subcultivation after 3 weeks was to the same substrate but without IAA. The pH in all substrates used in this example was 8.0. 18 leaf discs were used for each treatment.

Five weeks after co-cultivation the shoots were transferred to an MSO substrate containing 200 mg/l kanamycin sulfate, 32 mM saccharic acid, 300 mg/l cefotaxime and 300 mg/l carbenicillin, pH 8.0. Saccharic acid, an inhibitor of β-glucuronidase enzymes, was added to stop further conversion of zeatin glucuronide to zeatin. Together with the β-glucuronidase gene an NPT gene providing resistance to kanamycin was co-transferred. Non-transformed shoots (negative controls) survived, but the growth of these shoots was retarded on this substrate, while all of the transformed shoots (positive controls) containing an active NPT gene survived without any growth retardation.

The number of shoots was registered and the number of GUS-positive shoots among the total number of shoots was determined by the X-gluc assay (Example 3) 3 weeks after the last sub-cultivation (8 weeks after co-cultivation). The results are shown below:

TABLE 10

Positive selection of genetically transformed shoots using ZOGN sodium salt

| ZOGN mg/l | GUS-postive shoots per leaf disc | % GUS-positive shoots amona total shoots |
|---|---|---|
| 0.07 | 0.3 | 18.5 |
| 1.0 | 2.8 | 40.3 |
| 15.0 | 0.2 | 5.1 |
| 0.07 + SL* | 0 | 0 |

*SL: 2 mM saccharo 1,4-lactone

The results given in the above table show that a successful positive selection of genetically transformed shoots using ZOGN was achieved. The induction of transgenic shoots was inhibited when the β-glucuronidase specific inhibitor saccharo 1,4-lactone was added to the substrate, which shows that the growth of transgenic shoots and thus the success of the positive selection was dependent upon the β-glucuronidase catalyzed conversion of ZOGN to zeatin.

EXAMPLE 10

SELECTION OF GENETICALLY TRANSFORMED SHOOTS USING ZEATIN-O-β-GLUCURONIC ACID AT VARIOUS TEMPERATURES

The temperature dependency of the positive selection system using cytokinin glucuronides was investigated using zeatin-o-β-glucuronic acid (ZOGN) as the positive selection agent at 25° C., 30° C. and 35° C.

Transgenic tobacco shoots were prepared using essentially the same procedure as described below in Example 13. Co-cultivation was carried out for 3 days, the inoculum density corresponding to an OD of 1.5 at 660 nm. The substrate used after co-cultivation was MSO containing 10 mg/l 1-(2-hydroxyethylamino)-6-benzylamino-9-methylpurine (9-met), 350 mg/l carbenicillin, 350 mg/l cefotaxime and 0.1 mg/l indole acetic acid (IAA) and ZOGN sodium salt as indicated. 9-met (obtained from Apex Organics Ltd., UK) was added to inhibit glycosylation of zeatin and zeatin derivatives. 18 leaf discs were used for each treatment.

Seven weeks after co-cultivation the shoots were transferred to an MSO substrate containing 300 mg/l kanamycin sulfate, 350 mg/l cefotaxime, 350 mg/l carbenicillin, 0.1 mg/l IAA and 10 mg/l 6-(m-hydroxybenzylamino)-purine (OH-BA) and placed at a temperature of 25° C. OH-BA can be prepared as described by Kaminek et al. (*Plant Growth Reg.* 6, pp 113–120, 1987).

After six weeks on the kanamycin-containing substrate the number of green shoots was registered. Resistance to kanamycin indicates that the shoot is transgenic, because together with the β-glucuronidase gene and NPT gene providing kanamycin resistance was co-transferred. No non-transformed shoots (negative controls) survived on this substrate, while all of the transformed shoots (positive controls) containing an active NPT gene survived.

The percentage of kanamycin resistant shoots among the total number of regenerated shoots was calculated as the number of green shoots surviving on the kanamycin-containing substrate divided by the number of shoots transferred to the kanamycin-containing substrate. The results are shown in the table below:

TABLE 11

Positive selection of genetically transformed shoots using ZOGN sodium salt at different temperatures

| T ° C. | ZOGN mg/l | Kanamycin-res. Shoots per leaf disc | % Kanamycin-res. Shoots among total shoots |
|---|---|---|---|
| 25 | 1 | 0.3 | 4.3 |
| 30 | 1 | 1.3 | 14.8 |
| 35 | 1 | 0.2 | 26.7 |
| 25 | 15 | 0 | 0 |
| 30 | 15 | 2.4 | 26.2 |
| 35 | 15 | 0.2 | 182 |

The bioassay described in this example was performed on a linked co-transferred gene. This means that the β-glucuronidase gene is used for selection, while the resistance resulting from the introduced co-transferred NPT gene (kanamycin resistance gene) is assayed.

The results above show that, in addition to the β-glucuronidase gene, a co-transferred gene is also expressed when selection is performed using the β-glucuronidase gene. In addition, it can be seen that selection at elevated temperatures (i.e. about 30–35° C.) improves the selection of shoots per leaf disc and also the fraction of transgenic shoots among the total number of regenerated shoots.

By performing the X-gluc assay at different temperatures it has been observed in connection with the present invention that the intrinsic β-glucuronidase activity occurring in plants is inhibited at high temperatures, while the introduced β-glucuronidase activity is not affected. It was thus found that the intrinsic β-glucuronidase activity gradually decreased with increasing temperatures up to about 60° C., at which temperature there was essentially no intrinsic β-glucuronidase acitivty (as determined by the X-gluc assay). This may explain the improvement of the selection procedure at elevated temperatures.

EXAMPLE 11

POSITIVE SELECTION COMPARED TO AND COMBINED WITH NEGATIVE SELECTION

It has been shown that the positive selection system described herein is very efficient and advantageous compared to traditional kanamycin-based negative selection. However, good results are also obtained when the positive selection system is employed together with traditional negative selection.

The table below thus shows the results, in terms of the number of GUS-positive tobacco shoots per leaf disc and the percentage of GUS-positive shoots among the total number of shoots, for positive selection using BA3GN sodium salt, traditional negative selection using kanamycin and BA, as well as positive selection and negative selection in combination. In addition, the experiment included selection using BA3GN sodium salt together with saccharo 1,4-lactone (SL) (a strong specific inhibitor of the introduced β-glucuronidase).

The methods used were essentially as described below in Example 13, but Gamborg B5 substrate was used instead of MSO substrate.

positive selection was used (7.4%) than when negative selection was used (4.3%).

Advantageous results were also obtained using a combination of positive and negative selection, i.e. substituting a cytokinin in the traditional kanamycin-based negative selection system with a cytokinin glucuronide (BA3GN sodium salt). Thus, when 15 mg/l BA3GN sodium salt was combined with 300 mg/l kanamycin sulfate, the percentage of GUS-positive shoots was 11 times that obtained using BA and kanamycin, and when 15 mg/l BA3GN sodium salt was combined with 33 mg/l kanamycin sulfate, the number of GUS-positive shoots per leaf disc was 40 times that obtained using BA and kanamycin.

When 15 mg/l BA3GN sodium salt was combined with 10 mM of the GUS inhibitor SL, both the number of GUS-positive shoots per leaf disc and the percentage of GUS-positive shoots was drastically reduced compared to when 15 mg/l BA3GN sodium salt was used alone. This shows that the introduced GUS gene is responsible for the advantageous results obtained using the positive selection system, since the addition of SL to the growth medium severely inhibits the β-glucuronidase catalyzed conversion of inactive cytokinin glucurronide (BA3GN sodium salt) to active cytokinin in cells grown on this substrate, thereby leading to the observed reduction in the number of shoots induced. The positive selection system thus functions as intended, i.e. using an introduced β-glucuronidase to cleave a cytokinin glucuronide in genetically transformed cells, thereby releasing free cytokinin in these cells and leading to shoot formation.

TABLE 12

Positive selection combined with negative selection

| Selection substrate | Conc** | Kanamycin Conc. ** | GUS+ shoots Per leaf disc | | GUS+ shoots among total shoots | |
|---|---|---|---|---|---|---|
| | | | No. | Compared to BA+ Kanamycin | % | Compared to BA+ Kanamycin |
| BA | 1 | 300 | 0.01 | 1x | 4.3 | 1x |
| BA3GN* | 15 | 300 | 0.1 | 10x | 47.1 | 11x |
| BA3GN* | 15 | 100 | 0.2 | 20x | 3.2 | 0.7x |
| BA3GN* | 15 | 33 | 0.4 | 40x | 4.7 | 1.1x |
| BA3GN* | 15 | 0 | 0.3 | 30x | 7.4 | 1.7x |
| BA3GN* + SL (10 mM) | 15 | 0 | 0.2 | 2x | 0.9 | 0.2x |

*sodium salt
**Concentrations in mg/l

The experiment with BA together with kanamycin, which is the traditional negative selection system, was repeated as two independent experiments with 54 leaf discs per experiment. A single GUS-positive shoot was detected among a total of 23 selected shoots. The results for BA3GN sodium salt were obtained using 324 leaf discs. The experiment with SL (saccharo 1,4-lactone) was performed once with a total of 162 leaf discs.

The above table shows that positive selection using 15 mg/l BA3GN sodium salt (without kanamycin) gave 30 times as many GUS-positive shoots per leaf disc as the traditional negative selection sytems using 1 mg/l BA and 300 mg/l kanamycin sulfate. Furthermore, a greater percentage of the total number of shoots were GUS-positive when

EXAMPLE 12

MODIFICATION OF THE POSITIVE SELECTION SYSTEM TO IMPROVE THE SELECTIVE EFFECT OF THE CYTOKININ GLUCURONIDES

It has already been shown (see Table 3, Example 3) that the naturally occurring β-glucuronidase in plants is inactive at relatively high pH values, i.e. at pH values of about 6 or more, while the introduced β-glucuronidase is active up to the pH 8. By adding to the growth medium a compound which can raise the internal pH of the cells, e.g. ammonium nitrate, the selective shoot formation from the GUS-positive cells may be further improved, since it thereby becomes possible to block any background β-glucuronidase activity resulting from naturally occurring β-glucuronidase in the non-transformed cells.

The table below shows the number of shoots obtained from GUS-positive and GUS-negative tobacco leaf discs using various concentrations of BA3GN sodium salt and ammonium nitrate. The methods used were the same as those described in Example 3, with the exception that Gamborg B5 substrate was used instead of MSO substrate.

by β-glucuronidase results in a pH increase, thereby inhibiting the hydrolysis of cytokinin glucuronides in the non-transformed cells without inhibiting the effect of free cytokinin.

This principle was illustrated in an experiment on the effect of various concentrations of o-coumaryl-β-D-glucopyronuronic (CouGN) acid on shoot formation from GUS negative tobacco leaf discs induced by BA3GN sodium salt or BA. When o-coumaryl-β-D-glucopyronuronic acid is cleaved by the action of β-glucuronidase, o-coumaric acid is released. As mentioned

TABLE 13

Effect of ammonium nitrate on selective shoot formation from BA3GN sodium salt treated leaf discs (pH = 7)

Shoot formation (number of shoots and selectiviiy factor*) in GUS+ and GUS– leaf discs

| Ammonium nitrate Conc. (mM) | 7.5 mg/l BA3GN** | | | 15 mg/l BA3GN** | | | 30 mg/l BA3GN** | | |
|---|---|---|---|---|---|---|---|---|---|
| | GUS+ | GUS– | Sel.* factor | GUS+ | GUS– | sel.* factor | GUS+ | GUS– | sel.* factor |
| 25 | 4 | 0 | >4x | 33 | 2 | 17x | 73 | 36 | 2x |
| 35 | 6 | 1 | 6x | 50 | 7 | 7x | 73 | 36 | 2x |
| 45 | 0 | 0 | — | 20 | 6 | 3x | 57 | 27 | 2x |
| 55 | 14 | 0 | >14x | 34 | 0 | >34x | 37 | 11 | 3x |
| 65 | 2 | 0 | >2x | 8 | 2 | 4x | 25 | 45 | 1x |
| Average | 26 | 1 | 26x | 145 | 17 | 9x | 265 | 158 | 2x |

*The selectivity factor is the number of GUS positive shoots divided by the number of GUS–negative shoots, and thus gives an indication of the selectivity of a given treatment
**sodium salt It may be seen that the use of both BA3GN sodium salt and ammonium nitrate in appropriate concentrations leads to selective shoot formation in the GUS-positive leaf discs. For example, a combination of 15 mg/l BA3GN sodium salt and 55 mM ammonium nitrate gave 34 shoots from the GUS positive leaf discs, while no shoots were formed on corresponding GUS-negative leaf discs subjected to the same treatment.

Another possibility for improving the selectivity of the positive selection system using cytokinin glucuronides is to add to the growth medium a substrate which after cleavage above (see Example 11), o-coumaric acid is spontaneously converted to coumarin. This involves the elimination of an acid group (see below) and thereby an increase of pH to a level at which the activity of the native plant β-glucuronidase is presumed to be reduced.

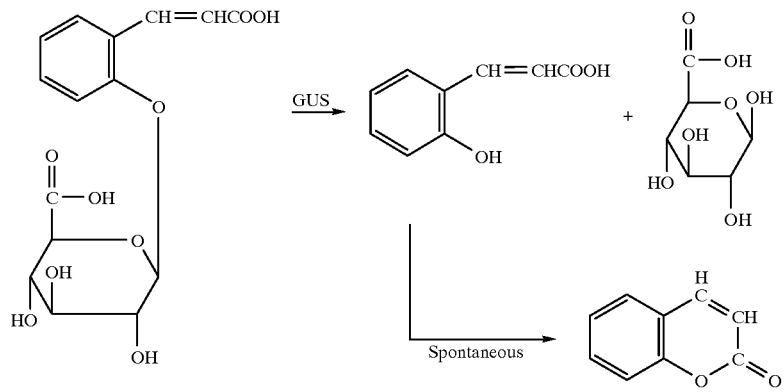

The experiment was performed using a BA concentration of 0.5 mg/l and a BA3GN sodium salt concentration of 10.0 mg/l. There were 12 discs per treatment, and the number of shoots was registered after 19 days. The results are shown below.

TABLE 14

Effect of o-coumaryl-β-D-glucopyranuronic acid (CouGN) on shoot formation induced by BA or BA3GN sodium salt

| Conc. (NM) | Number of regenerated shoots | | | | Relative % |
|---|---|---|---|---|---|
| CouGN | BA | relative % | BA3GN* | relative % | BA/BA3GN* |
| 0 | 71 | 100 | 77 | 100 | 1.0 |
| 0.0625 | 66 | 93 | 78 | 101 | 0.9 |
| 0.125 | 71 | 100 | 63 | 82 | 1.2 |
| 0.25 | 56 | 79 | 79 | 103 | 0.8 |
| 0.5 | 71 | 100 | 56 | 73 | 1.4 |
| 1.0 | 70 | 99 | 4 | 5 | 19.8 |
| 2.0 | 65 | 92 | 6 | 8 | 11.5 |
| 3.0 | 37 | 49 | 0 | 0 | >49 |
| 4.0 | 36 | 47 | 0 | 0 | >47 |
| 5.0 | 16 | 21 | 0 | 0 | >21 |
| 6.0 | 12 | 16 | 0 | 0 | >16 |
| 7.0 | 13 | 17 | 0 | 0 | >17 |

*sodium salt

The above table shows that the presence of o-coumaryl-β-D-glucopyronuronic acid in the growth medium inhibits shoot regeneration induced by BA3GN sodium salt but not by BA. Best results were obtained in this experiment using an o-coumaryl-β-D-glucopyronuronic acid concentration of about 3–4 mM. Several mechanisms could be incolved in the reduction of shoot formation induced by BA3GN, including the following: 1) an increased pH due to the release of o-coumaryl acid, as explained above, 2) substrate competition between CouGN and BA3GN, leading to a lower frequency of hydrolysis of BA3GN, and 3) a reduced transport of BA3GN into the cells. While the exact mechanisms involved in the observed reduction of shoot formation in the presence of CouGN were not determined, it is believed that an increased pH is likely to have been at least partially responsible. In any event, this experiment indicates that the selectivity of the positive selection system may be improved by using the introduced β-glucuronidase gene to establish a self-regulating mechanism which can significantly reduce the effect of any background enzyme.

EXAMPLE 13

PREPARATION OF GENETICALLY TRANSFORMED PLANTS

The following gives a general method which may be used for the preparation of genetically transformed plants.

Plant material

Leaves (*Nicotiana tabacum* 'Wisconsin 38') are obtained from plants grown in vitro or in vivo. In the latter case, the leaves are sterilized prior to transformation. Sterilization may be performed by placing the leaves for 20 min. in a solution of 5% calcium hypochlorite containing 0.1 ml Tween 80 per 1 followed by washing 5 times in sterile water. In vitro plants are grown in containers on ½ MSO. (½ MSO is the same substrate as MSO in a 50% concentration except for agar, sugar and vitamins.)

The leaves are placed one at a time in a 14 cm Petri dish. They are then punched or cut into pieces of about 1 cm² without a major vein, the edges of the pieces consisting of tissue which has been cut. Any cut tissue which has been bleached by hypochlorite sterilization is removed.

Cultivation of bacteria

One day before transformation a culture of bacteria is started by adding 2–3 ml of bacteria to 200 ml of LB medium in an Erlenmeyer flask. The bacteria is grown at 28° C. with agitation (300 rpm).

Transformation

The bacteria culture is diluted 50× or to OD 0.1 (at 660 nm) with ½ MSO immediately before transformation. Approximately 10 ml of the diluted bacteria suspension is poured into a 9 cm Petri dish, and the leaf pieces are dipped in this suspension for about 15 min. The leaf pieces are then removed and excess bacteria suspension is removed using sterile filter paper.

Co-cultivation

The day before transformation a piece of sterile filter paper is placed on co-cultivation dishes (typically containing MSO substrate) and the leaf pieces which have been dipped in the bacteria suspension are placed upside down on the filter paper. The leaf pieces are incubated in a growth chamber with a cycle of 12 hours of light and 12 hours of darkness for 2 days.

Selection/regeneration

The leaf pieces are transferred to Petri dishes containing cytokinin glucuronides as indicated and either 350 mg/l carbenicillin+350 mg/l cefotooxime or 800 mg/l carbenicillin alone, in certain cases in combination with kanamycin sulfate. The leaf pieces are subcultivated after 3 weeks to the same medium, but without cytokinin glucuronides.

Assay

Regenerated shoots are transferred to containers with ½ MSO. After about 2 weeks the X-gluc assay is performed on the green shoots. The shoots are sub-cultivated as necessary.

Planting out

Genetically transformed shoots which have formed roots (and which are GUS-positive) are planted out in a growth chamber. The shoots are planted in a suitable growth medium, e.g. sphagnum. They are then covered with plastic bags and are grown for about 1 week, after which the two corners of the plastic bags are cut off. After another week the plastic bags are removed.

EXAMPLE 14

INDUCTION OF SHOOT FORMATION FROM PLANT TISSUE WITH AND WITHOUT AN INTRODUCED β-GLUCURONIDASE GENE USING STEROLS AND A DI-β-D-GLUCURONIDE

Tests similar to those described in Examples 5 and 6 were performed on GUS-positive and GUS-negative tobacco leaf discs using substrates containing 100 mg/l β-sitosterol, 100 mg/l cholesterol, 10 mg/l campesterol, 1,88 mg/l BA3GN sodium salt and various concentrations of the di-β-D-glucuronide glycyrrihizic acid in the form of a ciammonium salt. In addition, half of the substrates contained 0.1 mM tridemorph. The number of shoots was registered after 17 days.

The results are shown in the following table.

TABLE 15

| | Regenerated shoots per leaf disc | | | |
|---|---|---|---|---|
| Glycyrrhizic acid* | Without tridemorph | | With tridemorph (0.1 mM) | |
| Conc. (NM) | GUS+ | GUS− | GUS+ | GUS− |
| 0.00125 | 1.6 | 0 | 0.4 | 0 |
| 0.0125 | 1.1 | 0 | 2.3 | 0 |
| 0.125 | 1.3 | 0.1 | 7.7 | 0.41 |
| 1.25 | 0 | 0 | 0 | 0 |
| 6.25 | 0 | 0 | 0 | 0 |

*diammonium salt.

It may be seen that the combination of sterols and the diammonium salt of glycyrrhizic acid leads to selective shoot formation in leaf discs containing an introduced β-glucuronidase gene. (As mentioned above (see Example 5) tridemorph inhibits the synthesis of sterols and thus has a inhibiting effect on shoot regeneration when the plant tissue is not supplied with sterols.) While the selective shoot induction effect is seen using substrates both without and with tridemorph, the greatest number of shoots is obtained in the substrates containing tridemorph, and in particular with a glycyrrhizic acid diammonium salt concentration of 0.125 mM.

EXAMPLE 15

SELECTIVE INHIBTION OF BA3GN INDUCED SHOOT FORMATION FROM WILD TYPE (GUS-) TOBACCO LEAF DISCS

Experiments were performed as described in Example 3 using the tobacco variety 'Burley' instead of 'Wisconsin 38'. Methyl-β-D-glucuronide (MG), which is hydrolyzed to methanol and glucuronic acid by GUS, was added to the substrate in various concentrations, along with either 1 mg/l BA or 15 mg/l BA3GN sodium salt. Methanol has been shown to inhibit the native GUS enzyme without affecting the introduced E. coli enzyme very much (Kosugi et al., 1990, Plant Sci., 133–120) while glucuronic acid liberated from methyl-β-D-glucuronide is a product inhibitor of GUS enzymes. By adding MG instead of the two compounds independently, the hydrolysis products are produced locally and concentrated in the compartment where the enzyme is localized. The results obtained are shown in Table 16 below.

TABLE 16

| Compound | Conc. Mg/l | Shoots per leaf disc BA | BA3GN | Ratio BA/BA3GN |
|---|---|---|---|---|
| Methyl-β-glucuronide | 0 | 1.00 | 0.50 | 2.0 |
| | 1000 | 1.91 | 1.00 | 1.9 |
| | 3300 | 2.25 | 0 | — |
| Glucurnic acid | 0 | 1.00 | 0.50 | 2.0 |
| | 1000 | 0.33 | 0.08 | 4.1 |
| | 3300 | 0.83 | 0 | — |
| | 10,000 | 0.42 | 0 | |

BA 1 mg/l
BA3GN 15 mg/l

The above results show that the addition of either MG or glucuronic acid leads to a reduction of the number of shoots obtained on the BA3GN substrate compared to the number of shoots obtained on the BA substrate. By treating tissue with MG before expression of the introduced GUS enyzme, it may therefore be possible to selectively eliminate or reduce the activity or the effect of the native GUS enzyme during the selection process. Differences between the introduced and the native Gus enzymes with regard to inhibition due to substrate competition, sensitivity to substrate inhibtion, amount of enzyme (activity), and sensitivity to product inhibition may also account for the effects of MG and other compounds having a similar effect on wild type tissues treated with glucuronides.

It is also possible that MG functions by competing with the uptake of other glucuronides such as BA3GN. If this is the case, MG could be used to reduce or eliminate uptake of other glucuronides in wild type cells. Introduction of a gene encoding a Gus enzyme that is secreted or a gene encoding a glucuronide permease might be used to select transgenic cells if uptake is inhibited by e.g. addition of MG to the substrate. In the case of glucumoide permease, only transgenic cells would take up the glucuronide (e.g. BA3GN) and due to the general occurrence of the native enzyme in plants (see e.g. Example 3), the compound would be activated inside the cells expressing the permease or another protein which facilitates the uptake of glucuronides).

It is also interesting that glucuronic acid itself is able to selectively inhibit the effect of BA3GN, presumably by blocking the effect of BA released through cleavage of BA3GN by GUS.

EXAMPLE 16

USE OF POSITIVE SELECTION AND A COMBINATION OF POSITIVE AND NEGATIVE SELECTION TO IMPROVE THE EFFICIENCY OF SELECTION OF TRANSGENIC CELLS, TISSUES OR SHOOTS FROM RECALCITRANT SPECIES

Sugar been is a very recalcitrant species with regard to producing transgenic plants. Many untransformed shoots are "selected" under conditions which give rise to transgenic shoots in ordinary transformation systems. The same was found to be the case when positive selection experiments (without addition of kanamycin) were performed using 5–15 mg/l BA3GN sodium salt under the conditions described in the following.

In Example 11 (see Table 12), the combination of positive and negative selection was found to reduce the number of "selected" non-transformed shoots. Therefore, the combination of positive and negative selection was tested on sugar beet, and this was found to give advantageous results.

Transformation was carried out using cotyledon explants as described below.

Seeds were germinated for 4 days in darkness on a substrate containing 0.7 g/l of agarose and 2 g/l of sucrose. The seedlings were then transferred to a Nunc container containing ½×MSO substrate and cultured for 3 days in the light. The cotyledons were removed from the seedlings, and the cotyledon explants were then brushed on the petiole with a small brush containing an Agrobacterium suspension, the Agrobacterium containing 35S-NPTII and 35S-GUS (OD 660=0.1). The cotelydons were then co-cultivated for 4 days on a substrate containing ¹⁄₁₀ MSO substrate and 200 μM acetosyringone. The transformed explants were transferred to an MSO substrate supplemented with 0.25 mg/l of BA or 15 mg/l of BA3GN sodium salt (instead of BAP), 0.025 mg/l of naphthyl acetic acid, 400 mg/l of kanamycin, 800 mg/l of carbenicillin and 25 mg/ml of vancomycin, and the explants were incubated for 21 days on this substrate. The regenerated shoots were then transferred to containers containing the same substrate. After 52 days on this substrate all the shoots were transferred to MSO substrate supplemented with 800 mg/l carbenicillin, 25 mg/l vancomycin and 0.1 mg/l BA. After 14 days GUS assays as described in Example 3 were performed on the selected plant material.

The results are shown in the table below.

TABLE 17

Transformation of sugar beet
Combination of positive and negative selection

| | No. of explants | GUS+ shoots | GUS+ shoots (%) |
|---|---|---|---|
| Negative selection | 100 | 0 | 0% |
| Positive and negative selection | 177 | 4 | 2.3% |

Negative selections: 400 mg/l kanamycin sulphate + 1 mg/l BAP
Positive and negative selection: 400 mg/l kanamycin sulphate + 15 mg/l BA3GN It can be seen that with the combination of positive and negative selection, transgenic shoots are produced under conditions in whichi no transgenic shoots are produced using the traditional negative selection system. This shows that the use of the positive selection system is very advantageous compared to the use of pure negative selection systems in sugar beet.

This in turn indicates that the use of positive selection (alone in combination with negative selection) may make it possible to produce transgenic plants in other recalcitrant species in which only low transformation/selection frequenceis are obtained or in which no transgenic plants are able to be selected at all using negative selection systems

EXAMPLE 17

POSITIVE SELECTION SYSTEMS BASED ON THE USE OF INACTIVE N-SOURCES MADE AVAILABLE BY THE INTRODUCTION OF METABOLISING GENES

Experiments were performed as described in Example 3, but the normal nitrogen content of the MSO substrate was reduced to zero. Instead, the nitrogen compounds indicated in Table 18 were added. The substrate contained 1 mg/l BA. Substrates containing ammonium nitrate were used as positive controls.

These experiments were performed to investigate whether opines are inactive or whether they can be used by plant cells as nitrogen sources in substrates not containing any other nitrogen source. Because genes encoding enzymes which metabolise opines are well known, the major prerequisite for using opines in a positive selection system is the identification of opines that cannot be used as a nitrogen source for plant tissues and cells are not containing introduced genes which enable the plant cells to utilize the opines in question. The results are given below.

TABLE 18

The effect of opines on shoot formation from tobacco leaf discs in substrates without nitrogen (number of shoots per 9 leaf discs)

| Compound | Concentration (mM) | | | | |
| --- | --- | --- | --- | --- | --- |
| | 0 | 10 | 20 | 40 | 80 |
| Octopine | 13 | 11 | 15 | 15 | 7 |
| Mannopine | 13 | >50 | >50 | >50 | >50 |
| Nopaline | 13 | 18 | 19 | 11 | 8 |
| Ammonium nitrate | 13 | >50 | >50 | >50 | >50 |

In tested substrates containing no nitrogen, a few shoots were regenerated. This may have been possible because nitrogen can be mobilized from the tissue in the explant. To avoid any shoot formation in the treatments without any nitrogen, the explants can be starved for nitrogen by growing the parent cultures on nitrogen-free substrates before use or by pre-treating the explants on a nitrogen free substrate, e.g. without shoot inducing hormones.

It was surprisingly found that octopine and nopaline cannot support shoot formation, while mannopine can function as a good nitrogen source and support shoot formation from the leaf disc.

It is likely that the reason why nopaline and octopine cannot function as nitrogen sources is that these compounds are not taken up, metabolized or hydrolyzed into usable compounds. It is well known that organisms containing genes involved in the transport and metabolism of opines, e.g. Agrobacterium, are able to use opines as a nitrogen source, while Agrobacterium or other bacteria strains not containing genes encoding opine metabolism are not able to grow on substrates containing only opines as a nitrogen source.

Based on these results, positive selection systems may be established by introducing one or more opine metabolism or transport genes into transgenic plant cells using selection substrates not containing or with a reduced level of nitrogen sources other than e.g. nopaline or octopine. The identification or isolation of genes or genetic material conferring to the recipient the capacity to utilize octopine and nopaline has been described in the literature: see e.g. C. Beaulieu et al., 1976, *J. Gen. Microbiol.* 38:843–49; P. M. Klapwijk et al., 1974 *J. Gen. Microbiol.* 96:155–163; C. L. Schardl and C. I. Kao, 1983, *Mol. Gen. Genet.* 191:10–16 or H. Wabiko et al., 1990, *J. Gen. Microbiol.* 136:97–103. Upon isolation of genetic material encoding opine metabolism, eukaryotic organisms may be transformed according to standard procedures described in the literature with appropriate sequences necessary for the functioning of the genes for opin metabolism.

Based on the above results, it is likely that other opines and corresponding catabolizing genes can be used in a similar manner, and it further appears likely that other inactive N-sources identified by similar means and their corresponding genes can similarly be used, e.g. amides in combination with amidases, peptides in combination with specific peptidases, etc.

EXAMPLE 18

PRODUCTION OF TRANSGENIC CALLUS FROM RECALCITRANT SPECIES USING POSITIVE SELECTION IN COMBINATION WITH NEGATIVE SELECTION

Experiments were performed as described in Example 11, although with certain modifications. The plant species used were the very recalcitrant breeding lines "V486" of winter oil seed rape and "S487" of summer oilseed rape. Seeds were sterilized and germinated as described in Example 16. Hypocotyls were used as explants and were inoculated and co-cultured as described in Example 11. After co-cultivation the explants were transferred to MSO substrate containing 0.1 mg/l naphthylacetic acid, 0.01 mg/l gibberellic acid (GA3), 500 mg/l carbenicillin, 50 mg/l kanamycin sulphate and 6.0 g/l agarose. The substrate contained in addition either 1 mg/l BA or 3.75, 7.5 or 15.0 mg/l BA3GN sodium salt. The pH was adjusted to 5.8. The Agrobacterium used contained in its T-DNA a GUS gene and a neomycinphosphotransferase II gene driven by 35S promoters. GUS assays were performed after 8 weeks and callus showing an intense blue staining in most of the callus cells was registered as being GUS.

TABLE 19

Production of transgenic callus from oilseed rape using positive selection in combination with negative selection

| | BA3GN (mg/l) | | | BA (mg/l) |
| --- | --- | --- | --- | --- |
| | 3.75 | 7.5 | 15.00 | 1 |
| Oilseed rape, winter type "V486" | | | | |
| Explants with callus | 19.0% | 23.0% | 30.6% | 0% |
| GUS+ callus per explant | 1.4% | 1.4% | 2.3% | 0% |
| GUS+ callus per callus | 7.1% | 5.9% | 7.5% | 0% |
| Oilseed rape, winter type V486" | | | | |
| Explants with callus | 5.2% | 9.2% | 6.3% | 0% |
| GUS+ callus per explant | 1.7% | 2.3% | 0.9% | 0% |
| GUS+ callus per callus | 33.3% | 25.0% | 14.2% | 0% |

These experiments show that with these very recalcitrant types of oilseed rape, only positive selection in combination with negative selection allowed selection of transgenic callus, while no GUS positive callus was obtained using traditional negative selection (substrates with BA instead of BA3GN sodium salt).

This shows that the introduction of the positive selection systems is very advantageous compared to the pure negative selection systems, also in callus systems. It also shows that the use of positive selection (alone or in combination with negative selection) may make it possible to produce transgenic plants in other recalcitrant species in which only low transformation/selection frequencies are obtained or in which no transgenic plants at all are selected using negative selection systems.

After transgenic callus has been selected, it can be regenerated into transgenic shoots, e.g. on a substrate containing a cytokinin in combination with a low concentration of auxins. No selection is needed during this process.

EXAMPLE 19

CONSTRUCTION OF THE BINARY PLASMID P (BKL4-MANNOSE) CONTAINING THE *E. COLI* PHOSPHOMANNOSE ISOMERASE CODING SEQUENCES

The *E. coli* phosphomannose isomerase (EC 5,3,2,8) gene originates from plasmid pGS63 (Miles, H. et al. Gene 32 pp 41–48 (1984)) (FIG. 1), a construction derived from pBR322, in which the region between the unique PstI and HindIII sites has been replaced by a section of the *E. coli* chromosome bearing the structural gene (man A) for phosphomannose isomerase and a fragment of the adjacent gene for furmarase (furm A). pGS63 has therefore lost a portion of the β-lactamase gene and is to be selected on tetracycline.

Figure 2:
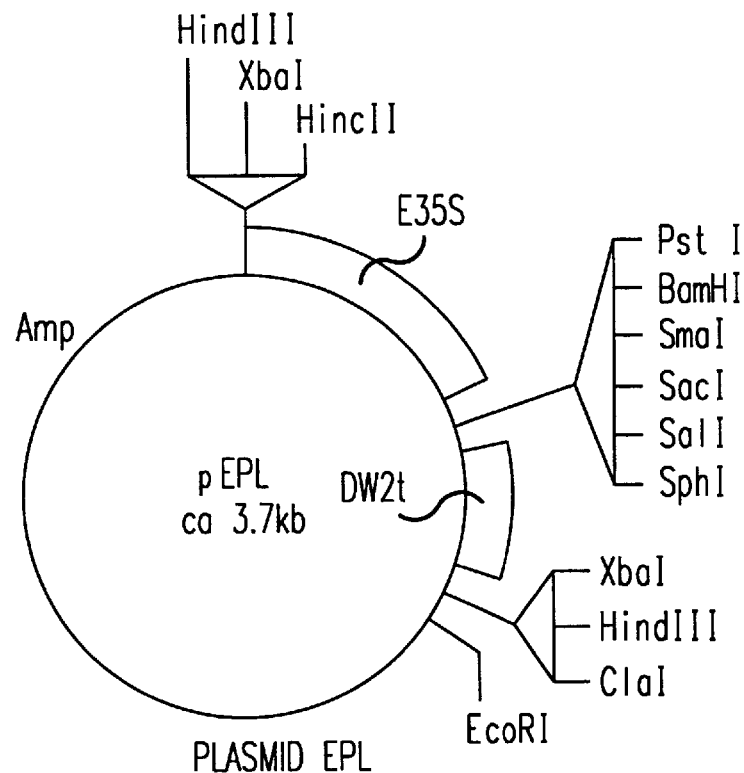
FIG. 2 shows plasmid EPL (Pietrzak, M. et al. Nucleic Acids Res. 14 pp 5857–5868 (1986))
Figure 3:
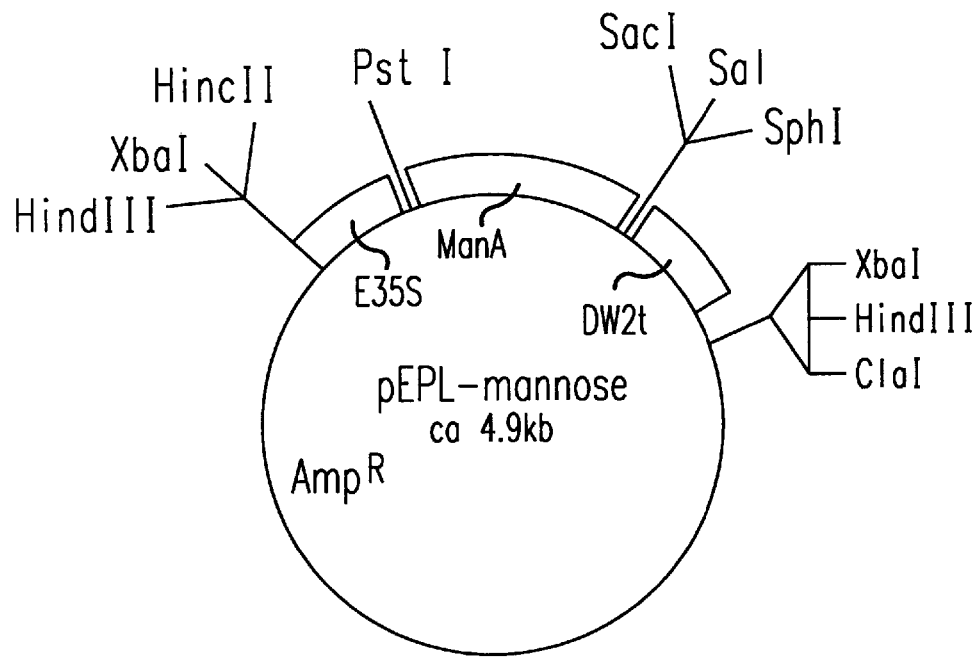
FIG. 3 shows plasmid pEPL-mannose which is approximately 4.9 kb.
Figure 4:
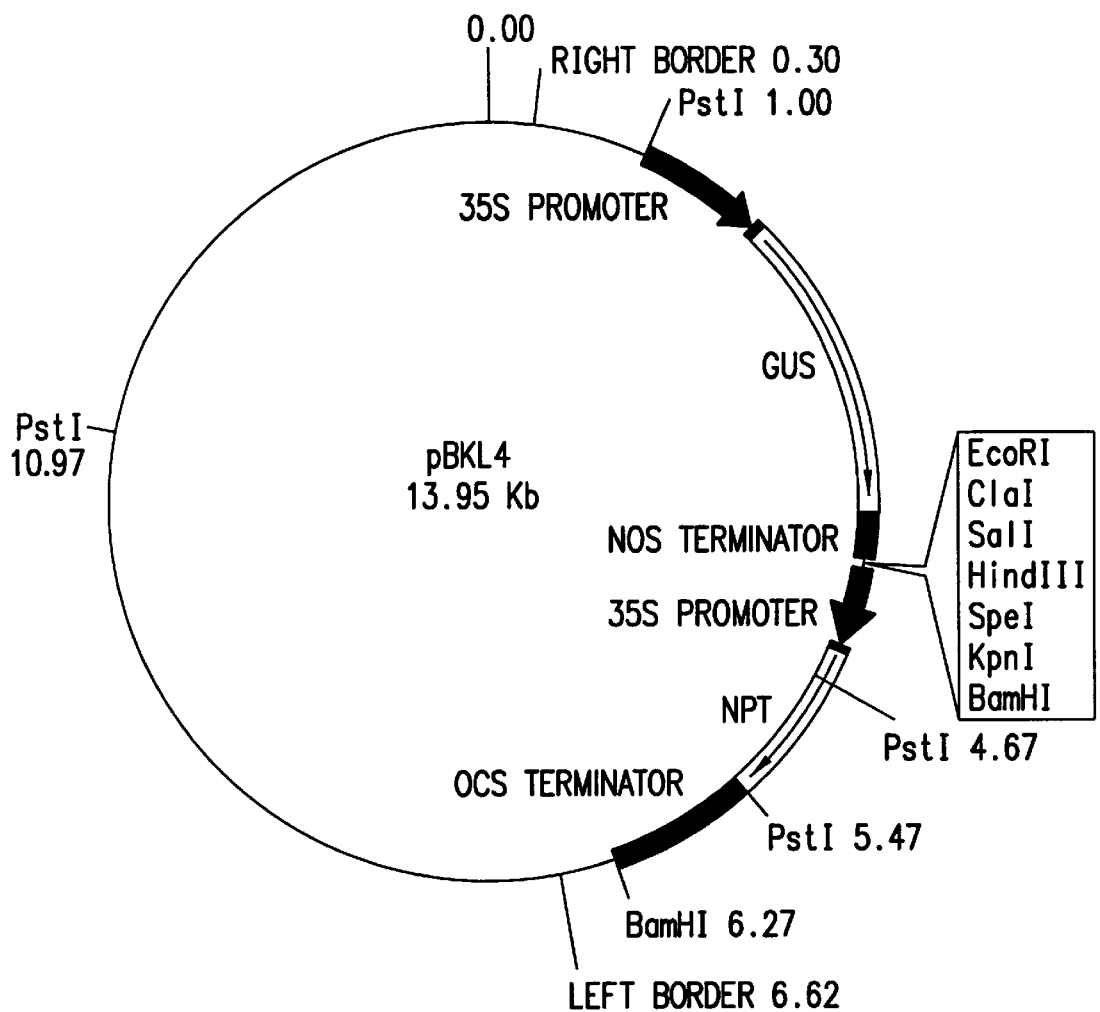
FIG. 4 shows the binary plasmid PBKL4 (Nielsen, K. K. et al. Mol. Plant Microbe Interact. 6 pp 495–506(1993))
Figure 5:
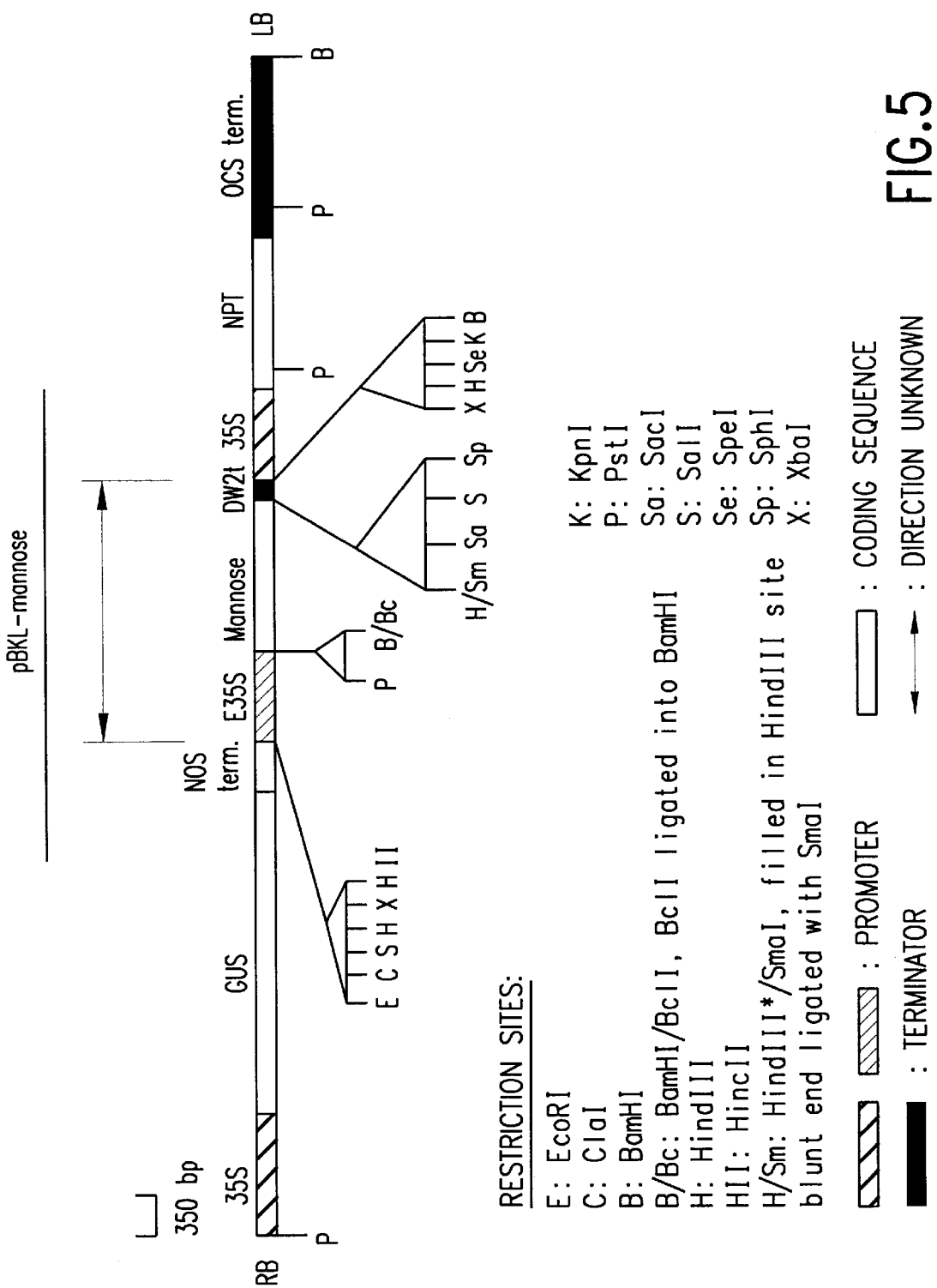
FIG. 5 shows plasmid pBKL4 containing the man A gene inserted between the GUS gene and the NPTII gene.

The PstI/BarmHI fragment (2466 bp) containing the entire PstI/HindIII chromosomal fragment and a 357 bp section of pBR322 was ligated into the multiple cloning site of pUC18 to form pDO18 (see FIG. 1).

pDO18 is digested with HindIII and the resultant recessed 3' termini are filled using Klenow polymerase. The open DO18 plasmid with the filled HindIII* site (HindIII*) (see FIG. 1) is digested with BclI and the 1218 bp BclI-HindIII* fragment containing the coding region of phosphomannose isomerase is cloned into the plasmid pEnhanced-Peter-Linker (pEPL), which was first digested with SamI and then with BamHI. The resultant plasmid is called p(EPL-mannose).

pEPL is constructed from pCaMVCN (Fromm et al. Proc. Natl. Acad. Sci. U.S.A. 82, p 5824 (1985); Fromm et al. Nature 319, p 791 (1986)) in which the CAT gene is removed by a PstI digestion. A small linker (linker: PstI-BamHI-BalI-PstI) is inserted into this plasmid PstI site, giving the plasmid called pLise (pL). pL is digested with HincII and BglIII and the resultant fragment containing the 35S promoter and the NOS terminator is cloned into another pL plasmid digested with EcoRV and BglIII. Both EcoRV and HincII are blunt ended sites. The resulting construct is called pEnhanced-Lise (pEL). pEL differs essentially from pCaMVCN in that it contains a variant 35S promoter with a tandem duplication of the 250 bP of the upstream sequence of the promoter. The variant 35S promoter has a transcriptional activity approximately ten times higher than the natural 35S promoter (Kay et al. Science 236, pp 1299–1302 (1987)). pEL is digested with PstI and BglIII, thereby removing the NOS terminator, and a CaMV terminator (DW2t) is inserted instead. Finally, a linker (PstI-BamHI-SmaI-SacI-SaII-SphI) is inserted into the PstI site situated between the enhanced 3c5S promoter and the CaMV terminator. This plasmid is called pEPL (see FIG. 2).

p(EPL-mannose) is digested with HindIII in order to isolate the fragment containing the entire enhanced 35S promoter, the coding region of *E. coli* phosphomannose isomerase and the CaMV terminator. The isolated fragment is cloned into the HindIII site of the binary vector pBKL4 (FIG. 5). The resulting plasmid is termed p(BKL-mannose) FIG. 3. The HindIII site in pBKI4 is situated between a kanamycin resistance gene and the β-glucuronidase (GUS) gene (see FIG. 4). The mannose chimeric gene, the kanamycin resistant gene (NPTII) and the GUS gene each having a promoter and terminator. FIG. 5 shows the p(BKL-mannose) construction containing the chimeric phosphomannose isomerase gene inserted between the GUS and the NPTII gene of plasmid pBLK4.

The construct p(BKL-mannose) is isolated from *E. coli* and transformed into the *Agrobacterium tumefaciens* strain LBA4404 which contains the disarmed helper plasmid pAL4404 (Hockema, et al. Nature 303, pp 179–180 (1983); Ooms et al. Plasmid 7, pp 15–29 (1982)) by the freeze thaw methods (Holsters et al. Mol. Gen. Genet 163, pp 181–187 (1978)).

The sequence of the structural gene (man A) encoding phosphomannose isomerase has been published by Miles and Guest (Gene 32, pp 41–48 (1984)).

Axenic stock cultures

Shoot cultures of *Solanum tuberosum* 'Saturna' 'Bintjc' or 'Dianella' are maintained as described by Linsmaier and Skoog (Physiol. Plant 18, pp 100–127 (1965)), on an LS substrate (see below) supplemented with 2 μM silver thiosulfate, the temperature being 25° C. and the cultures being subjected to cycles having 16 h light/8 h dark. The stock cultures are sub-cultured after 20–40 days. Leaves were removed from the shoots and cut into nodal segments (approximately 0.8 cm) each containing one node.

Inoculation of potato tissues

Co-cultivation plates contain LS substrate (sucrose 30 g/l), agar (8 g/l). 2,4-dichlorophenoxyacetic acid (2.0 mg/l) and trans-zeatin (0.5 mg/l).

Shoots from approximately 40 day old shoot cultures (height approximately 5–6 cm) are cut into internodal segments (approximately 0.8 cm). The segments are placed into liquid LS-substrate (LS-medium) containing *Agrobacterium tumefaciens* transformed so that it contains a binary vector comprising genes which it is intended should be incorporated into the potato cells. Such genes include, for example, those encoding β-glucuronidase (GUS), the NPT II gene providing resistance to the antibiotic kanamycin and/or genes encoding proteins involved in mannose metabolism, for example mannose 6 phosphate isomerase, mannose epimerases, phosphomannomutases etc. (see below).

The Agrobacterium are cultured over-night in YMB-substrate (dipotassiumhydrogenphosphate (trihydrate) (0.66 g/l); magnesium sulphate (heptahydrate) (0.20 g/l); sodium chloride (0.10 g/l); mannitol (10.0 g/l); and yeast extract (0.40 g/l) containing appropriate antibiotics (corresponding to the resistance gene of the Agrobacterium strain) to an optical density at 660 nm (OD-660) of approximately 0.8. The suspension is then centrifuged and the cells resuspended in the LS-medium so that the OD-660 thereof is 0.5.

The above mentioned internodal segments are then incubated in the suspension of the resuspended Agrobacterium for about 30 minutes, and then the excess of bacteria is removed from the by blotting them onto sterile filter paper.

Co-cultivation of the shoot segments and Agrobacterium

The shoot segments are co-cultured with bacteria for 72 hours on filter paper on LS-substrate (as defined above) in petri dishes covered with white paper tissues. This substrate is referred to hereafter as "co-cultivation substrate". The substrate and segments are covered with sterile filter papers, and the petri dishes are placed at 25° C. and subjected to cycles of 16 h light/8 h dark.

Washing procedure

After 48 hours of co-cultivation, the shoot segments are transferred to LS-medium supplemented with 800 mg/l carbenicillin. The thus transferred segments are then gently shaken to dislodge or destroy adherent Agrobacterium.

Selection of transformed tissue

The thus washed segments are then transferred to LS-substrate (as above) except that the trans-zeatin concentration was 1 mg/l, and the substrate is supplemented with gibberellic acid (0.1 mg/l) and carbenicilin (800 mg/l) and optionally kanamycin sulfate (50 mg/l ) and/or mannose (0–20 g/l) and/or sucrose (0–20 g/l). This substrate is referred to hereafter as "selection/regeneration substrate".

The segments are subcultured onto fresh substrate at two week intervals or as described below. Within 2 to 4 weeks, shoots develop from the segments and the formation of new shoots continues for about 3–4 weeks.

Rooting of regenerated shoots

The regenerated shoots are transferred to rooting substrate composed of LS-substrate supplemented with carbenicilin (500 mg/l).

Transfer or regenerated shoots to soil

The newly rooted regenerated shoots (plants) (height approximately 2–3 cm) are transplanted from rooting substrate to soil and placed in a growth chamber at 21° C. having a 16 hours light/8 hour dark cycle and 200–400 $\mu$E/sqm/sec. When the plants are sufficiently well established they are transferred to a greenhouse, where they are grown until tubers develop and the upper part of the plants exhibit senescence.

Verification of the genetic identity of the transformants

The transgenic genotypes of the regenerated shoot are verified.

(a) by performing NPTII assay as described by Radke et al. (Theor. Appl. Genet. 75, pp 685–694 (1988)); or
(b) by performing a GUS assay on the enzyme expressed by the co-introduced β-glucuronidase gene according to Hodal et al. (Plant. Sci. 87, pp 115–122 (1992)); or
(c) by assaying for the expression of the mRNA of the introduced gene encoding an enzyme, for example phosphomannose isomerase, involved in mannose metabolism, or by measuring the activity of the enzyme.

EXAMPLE 20

Regenerated plants are produced as described above, except that the shoot segments are not co-cultured with bacteria and the washing procedure consequential thereon is omitted. The number of regenerated shoots is determined up to the 40th day from the start of experiment. Table 20 shows the inhibition by mannose of the regeneration of shoots from potato stem segments which had not been transformed with Agrobacterium. It can be seen from Table 20 that mannose effectively inhibits regeneration of such shoots, and that sucrose promotes such regeneration. In general, mannose cannot be used as a carbohydrate source in most plant species. When mannose is added to plants it is metabolized and mannose 6-phosphate accumulates. Mannose 6-phosphate can be converted to fructose 6-phosphate by mannose 6-phosphate isomerase, the amount converted being dependent upon the activity of the isomerase. Such fructose 6-phosphate may be utilized by plants, but in principal high levels of mannose (whether or not an alternative carbohydrate source is available) are toxic to plants.

Thus, as can be seen from Table 20, shoot formation is totally inhibited when the mannose concentration is 5–10 g/l, irrespective of the availability of sucrose, even when that is present in high concentrations.

TABLE 20

| Concn (g/l) sucrose | Concn (g/l) mannose | Regenerated shoots/explant (%) |
| --- | --- | --- |
| 0 | 0 | 0 |
| 0 | 5 | 0 |
| 0 | 10 | 0 |
| 0 | 20 | 0 |
| 10 | 0 | 50 |
| 10 | 5 | 3 |
| 10 | 10 | 0 |
| 10 | 20 | 0 |
| 20 | 0 | 53 |
| 20 | 5 | 0 |
| 20 | 10 | 0 |
| 20 | 20 | 0 |

Inhibition by mannose of the regeneration of shoots from non-transformed potato stem segments.

EXAMPLE 22

Regenerated plants are produced as described above. The Agrobacterium with which the shoot segments are co-incubated are transformed with construct p(BKL-mannose) which is obtained as described above, so that the bacteria harbor a vector comprising the genes encoding GUS and mannose 6 phosphate isomerase.

Transgenic (GUS+) shoots are selected on the basis of their ability to metabolize mannose in the presence of an agent (methyl-3-0-glucose) which reduces the toxicity to the shoots of the mannose. Shoots which are GUS+ are selected on the basis of their ability to grow in the presence of mannose at a concentration of about 5 g/l.

Control experiments are also performed in which the Agrobacterium which are used to transform the shoot segments harbor a vector similar to p(BKL-mannose) except that it lacks the gene encoding mannose 6-phosphate isomerase. No GUS+ transformants are obtained when the regenerated transformed shoots are grown in the presence of mannose at 5 g/l and sucrose at 20 g/l.

EXAMPLE 23

A further experiment is performed in which the Agrobacterium which are used to transform the shoot segments harbor a vector similar to p(BKL-mannose) except that it lacks the gene encoding mannose 6-phosphate isomerase. Such a vector comprises the gene encoding NPT ll which is capable of rendering cells transformed therewith resistant to kanamycin. Accordingly, GUS+ transformants are selected on the basis of their resistance to kanamycin present at a concentration of 50 mg/l . In this latter selection, a lower proportion than in Example 22 of the selected cells are GUS+.

EXAMPLE 24

Example 23 is repeated, except that the Agrobacterium are transformed with p(BKL-mannose) and the GUS+ transformants are selected on the basis of their ability to grow on kanamycin (50 mg/ml). In this case a lower proportion than in Example 23 of the selected shoots are GUS+.

EXAMPLE 25

The standard leaf disc procedure for tobacco as described in Example 13 is performed, except that inoculation with Agrobacterium and the co-cultivation step are omitted. Benzyladenine (1 mg/l) is used as cytokinin and the carbohydrate content is as indicated below. The number of regenerated shoots from each leaf disc are registered after 21 days.

Table 21 shows that D-xylose does not inhibit shoot regeneration when sucrose is present and in addition that D-xylose is not utilized as a carbohydrate source. D-xylulose is a good carbohydrate source during shoot regeneration.

TABLE 21

Test of the ability of D-xylose and D-xylulose to function as carbohydrate sources during shoot regeneration from tobacco leaf discs.

| Xylose g/l | Sucrose g/l | Xylulose g/l | Number of regenerated shoots each leaf disc |
|---|---|---|---|
| 0 | 0 | 0 | 0 |
| 10 | 0 | 0 | 0 |
| 10 | 10 | 0 | 4.3 |
| 0 | 10 | 0 | 2.3 |
| 0 | 0 | 10 | 4.1 |
| 0 | 10 | 10 | 11.7 |

Similar results are observed with potato stem segments after 9 weeks of culturing. D-xylose does not function as a carbohydrate source in potato.

TABLE 22

| Compound | Conc. g/l | # of Shoots per explant | Size % of control | explants alive % of control |
|---|---|---|---|---|
| None | — | 0 | 21 | 12 |
| Sucrose | 10 | 2.8 | 100 | 100 |
| D-xylose | 10 | 0 | 13 | 0 |
| D-xylose | 5 | 0 | 17 | 0 |
| D-xylulose | 5 | 2.2 | 74 | 58 |

Further results indicate that D-xylose is an inhibitor of shoot regeneration in potato stem segments when sucrose is present, however, explants stay alive (green). These results support the fact that in potato xylose/xylose isomerase will function as a positive selection system.

EXAMPLE 26

A xylose isomerase gene is used to select for transformed potato plants on D-xylose. Xylose can be converted to xylulose by xylose isomerase and the transformed cells are selected on the bases of their ability to metabolize xylose as a carbohydrate source.

A. Construction of the plasmid pAH-Xyl

The *Streptomyces rubiginosus* D-xylose isomerase (D-ketol isomerase EC 5.3.1.5) gene originated from M13mp19 bacteriophage lysate (pers. Comm. C. A. Batt, Cornell University). The M13 lysate is propagated in *E. coli* and the replicative form is isolated. From the plasmid preparation the xylA fragment is cut out as an EcoRI-BamHI fragment (1180 bp) and ligated into the SalI/BamHI sites of pSG10 with a SalI/EcoRI adaptor (FIG. 8).

Figure 8A:
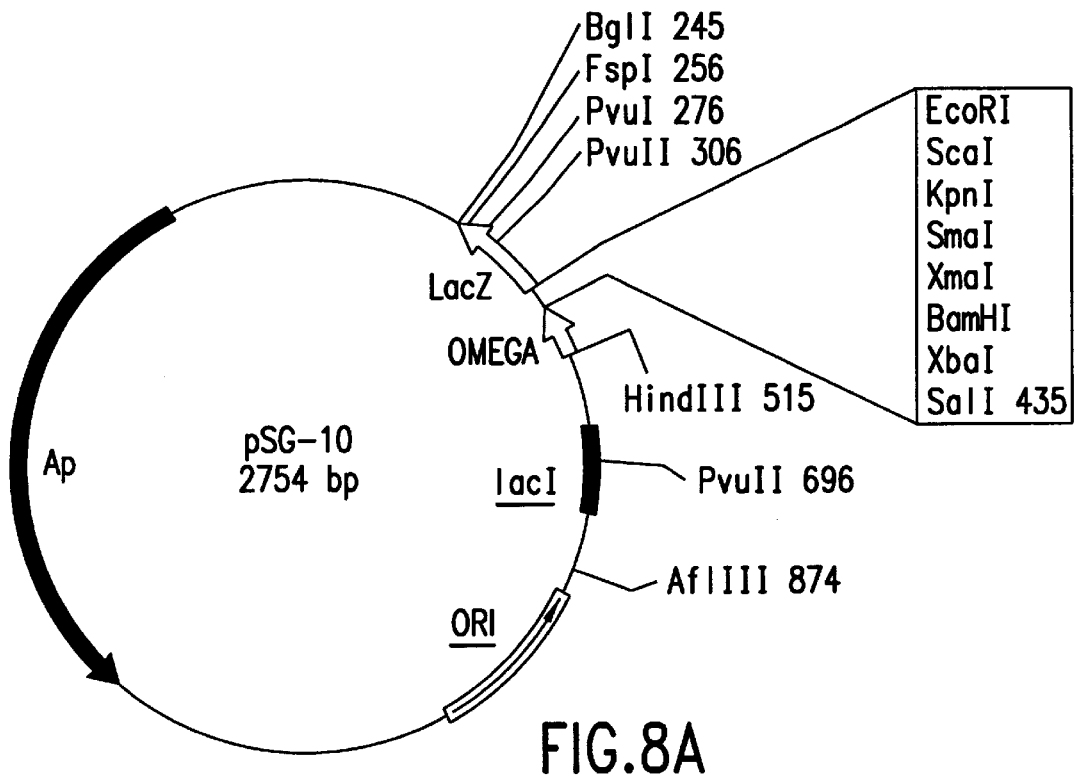
FIG. 8 shows the plasmid pSG10 and pPS48.
Figure 8B:
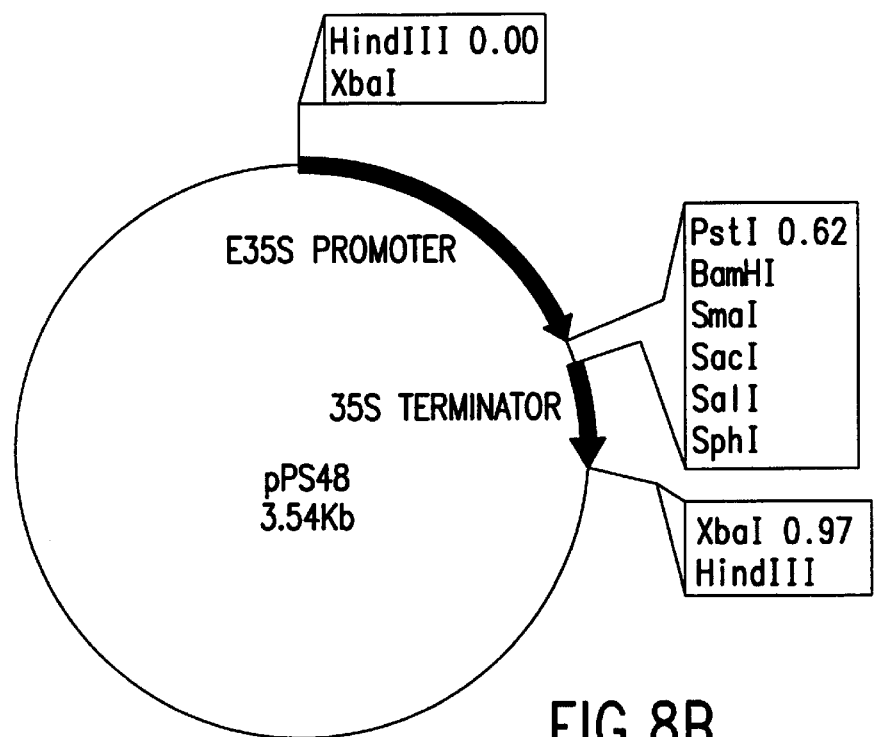
Figure 9:
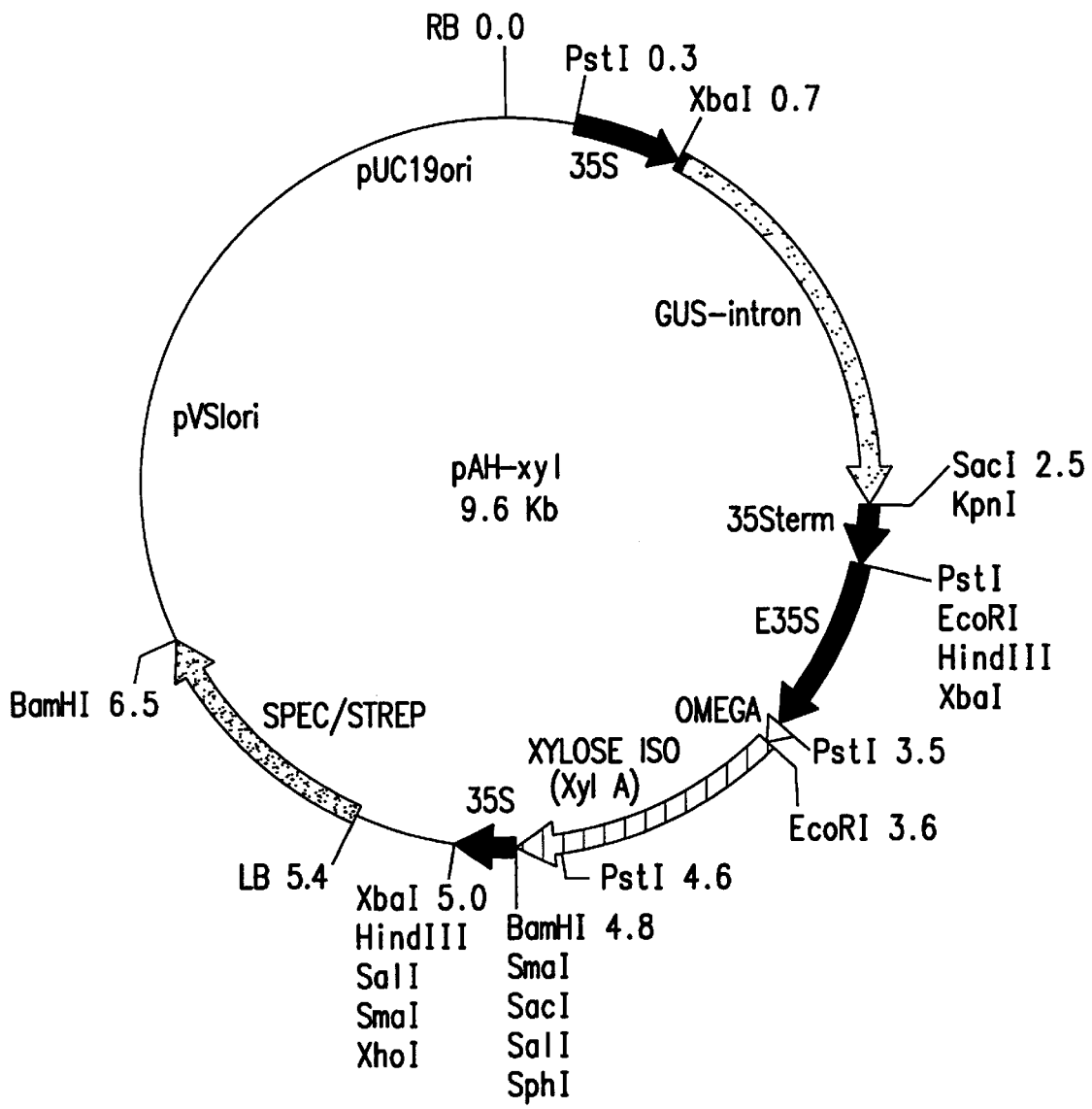
FIG. 9 shows plasmid PAH-Xyl containing a xylose isomerase gene.

The omega fragment together with the xylA gene is cut out of pSG10 with HindIII/BamHI and ligated into the PstI/BamHI sites of pPS48 with the help of a PstI/HindIII adaptor (FIG. 8). The pPS48 is digested with HindIII in order to isolate the fragment containing the entire enhanced 35S promoter, the omega fragment, the coding region of *S. rubiginosus* xylose isomerase and the CaMV terminator. The isolated fragment is cloned into the HindIII site of the vector. The resulting plasmid is termed pAH-Xyl (FIG. 9) which contains the GUS-intron gene in the T-DNA and the spec/strep resistance gene outside the T-DNA. The orientation of the inserted genes are marked on the plasmid map. The constructs are isolated from *E. coli* and transformed into the *Agrobacterium tumefaciens* strain EHA 101.

A further xylose isomerase gene from *Clostridium thermosulfurogene* has been cloned into the same vector as described above and introduced into potato by Agrobacterium mediated transformation. The gene is a thermostable D-xylose isomerase (1330 bp) and originates from plasmid pCMG11-3 (Lee, C. Et al. 1990 J. Biol. Chem. 265:19082–19090). However, the isomerase gene contains a HindIII site and therfore the HindIII site in the vector is changed to a SpeI site which has the same overhang as XbaI. The vector is cut with HindIIII and a HindIIII-SpeI-HindIIII linker is inserted into the plasmid at the HindIII site. The resulting plasmid is opened with SpeI and the XbaI fragment ligated into the SpeI site. The arrangment of the genes on the T-DNA are: (RB -35S-Gusintron-t35S, E35S-omega-xylA-t35S (LB).

B. Transformation experiment

A double transformation experiment is performed wherein the plasmid pAH-Xyl (FIG. 9) is introduced together with a constuct which differs in that it does not contain the GUS gene, but does contain a kanamycin resistance gene instead. Shoots are selected on kanamycin (50 mg/l) and sucrose (30 g/l) to confirm that the GUS gene (the reported gene) is functioning and further that the xylose and Kanamycin constructs are functioning. Results indicate that the frequency of double transformation is 29%.

Shoots are regenerated from potato stem segments treated with various concentrations of sucrose and D-xylose. The number of shoots are counted after 11 weeks of selection. 105 explants are tested per treatment. Results as listed in Table 23 demonstrate that plants transformed with the xylose isomerase gene survive better on media containing D-xylose than plants transformed with the kanamycin resistance gene.

TABLE 23

| Sucrose (g/l) | D-xylose (g/l) | No. Shoots | GUS+ Shoots | GUS+ shoots/no. Shoots (%) | GUS+ Shoots/-explants |
|---|---|---|---|---|---|
| with pAH-Xyl | | | | | |
| 2.5 | 2.5 | 0 | 0 | — | 0 |
| 5.0 | 2.5 | 0 | 0 | — | 0 |
| 10.0 | 2.5 | 84 | 5 | 6 | 0.05 |
| 2.5 | 5.0 | 0 | 0 | — | 0 |
| 5.0 | 5.0 | 0 | 0 | — | 0 |
| 10.0 | 5.0 | 20 | 0 | 0 | 0 |
| 2.5 | 7.5 | 0 | 0 | — | 0 |
| 5.0 | 7.5 | 0 | 0 | — | 0 |
| 10.0 | 7.5 | 7 | 4 | 57.1 | 0.04 |
| with control (Kanamycin resistant gene) | | | | | |
| 2.5 | 2.5 | 0 | 0 | — | 0 |
| 5.0 | 2.5 | 0 | 0 | — | 0 |
| 10.0 | 2.5 | 32 | 0 | 0 | 0 |
| 2.5 | 5.0 | 0 | 0 | — | 0 |
| 5.0 | 5.0 | 0 | 0 | — | 0 |
| 10.0 | 5.0 | 5 | 0 | 0 | 0 |
| 2.5 | 7.5 | 0 | 0 | — | 0 |
| 5.0 | 7.5 | 0 | 0 | — | 0 |
| 10.0 | 7.5 | 2 | 0 | 0 | 0 |

Similar results are obtained with Agrobacterium transformation experiments using potato stem segments and the xylose isomerase gene from *C. thermosulfurogenes*. After 7 weeks of culturing this construct also yields better results than the kanamycin selection system.

EXAMPLE 27

Explants are produced and treated as described above under "selection of transformed tissue", except that the selection/regeneration substrate was not supplemented with kanamycin or cabenicillin, and that plant tissue is not transformed. Thus the only subcultivation step is when the explants are transferred from the co-cultivation substrate to the selection/regeneration substrate which is supplemented with xylose at the concentrations indicated below. The number of regenerated shoots is recorded after 12 weeks.

TABLE 24

The ability of D-xylose to function as a carbohydrate source during shoot regeneration from potato stem segments.

| Xylose g/l | Sucrose g/l | Number of regenerated shoots each stem segment |
|---|---|---|
| 0 | 0 | 0 |
| 5 | 0 | 0 |
| 10 | 0 | 0 |
| 20 | 0 | 0 |
| 0 | 10 | 6 |
| 5 | 10 | 3 |
| 10 | 10 | 0 |
| 20 | 10 | 0 |

Table 24 shows that D-xylose (compared to D-mannose) is a weak inhibitor of shoot regeneration when sucrose is present and in addition D-xylose does not function as a carbohydrate source in plants which are non-transgenic in respect of a xylose metabolizing enzyme or protein. Moreover, D-xylulose (5 g/l) added to substrates in the absence of sucrose enabled the regeneration of 2.2 shoots per explant after 9 weeks.

EXAMPLE 28

Example 25 is repeated except that the selection/regeneration substrate is supplemented with methyl 3-0-glucose (MOG) at the concentrations indicated in Table 25. The percentage of live explants is registered after 8 weeks.

Table 25 shows that co-treatment with MOG inhibits the toxic effects of mannose on sensitive plant tissues. Because mannose is toxic in concentrations which are optimal for compounds which function as carbohydrate sources, the addition of MOG makes it possible to supplement the substrate with optimal carbohydrate concentrations in the form of mannose. This makes it possible to utilize mannose as a positive selection agent, in the absence of other carbohydrate sources.

TABLE 25

Inhibition of the toxicity of mannose by co-treatment with methyl-3-O-glucose (MOG).

| Mannose (g/l) | 0 | 5 | 10 | 0 | 5 | 10 |
|---|---|---|---|---|---|---|
| Sucrose (g/l) | 0 | 0 | 0 | 10 | 10 | 10 |
| MOG (g/l) | | | | | | |
| 0 | 71 | 4 | 0 | 100 | 1 | 4 |
| 5 | 13 | 54 | 0 | 100 | 100 | 5 |
| 10 | 47 | 82 | 9 | 100 | 100 | 41 |
| 20 | 50 | 98 | 88 | 100 | 100 | 100 |

EXAMPLE 29

Example 28 is repeated, except that the regeneration/selection substrate contains mannose (15 g/l), methyl-3-0-glucose in the concentration indicated in Table 26, and does not contain sucrose. The transformed plant material is transgenic for the mannose 6-phosphate isomerase gene. After 21 days the selected shoots are harvested. All harvested shoots are assayed for the expression the co-introduced β-glucuronidase gene and the total number (from 2 harvests) of transgenic β-glucuronidase expressing (GUS+) shoots per explants is calculated as is the fraction of the β-glucuronidase expressing (GUS+) shoots among the total number of shoots selected (Table 26).

Table 26 shows that when mannose is added together with methyl-3-0-glucose, selection of transgenic shoots is possible even at high concentrations of mannose, in the absence of other carbohydrate sources.

TABLE 26

The effect of methyl-3-O-glucose on the selection of transgenic shoots on mannose containing substrates without sucrose.

| Mannose (g/l) | 15 | 15 | 15 | 15 | 15 |
|---|---|---|---|---|---|
| MOG (g/l) | 0 | 2.5 | 5.0 | 10 | 15 |
| GUS+ shoots/explant | 0 | 0.2 | 1.0 | 0.5 | 0.6 |
| GUS+ shoots/sel. shoots (%) | 0 | 57 | 81 | 89 | 53 |

EXAMPLE 30

Example 29 is repeated except that MOG is substituted by phloridzin. Table 27 shows that when mannose is added together with phloridzin selection of 100% transgenic shoots is possible at high concentrations of mannose in the absence of other carbohydrate sources. This is an example of how cross feeding and the production of escapers can be minimized by the addition of a carbohydrate transport inhibitor.

TABLE 27

| | 0.5 g/l Phloridzin | | | |
|---|---|---|---|---|
| | GUS+ Shoots/Sel. Shoots | | GUS+ Shoots/Expl. | |
| g/l Mannose | + Sucrose | + Sucrose | + Sucrose | + Sucrose |
| 5.0 | 94.0% | 100.0% | 1.2 | 0.08 |
| 7.5 | 88.0% | 78.5% | 0.5 | 0.5 |
| 10.0 | 100.0% | 95% | 0.5 | 0.5 |
| 12.5 | 100% | — | 0.03 | 0.0 |
| 15.0 | 100% | — | 0.03 | 0.0 |

EXAMPLE 31

Table 28 indicates that compounds other than mannose may be used as selection agents in transgenic plant tissue which comprises, inter alia, the mannose 6-phosphate isomerase gene from E. coli.

TABLE 28

Number of regenerated shoots per explant selected by compounds in addition to mannose.

| | Number of regenerated shoots per explant | |
|---|---|---|
| | Genotype | |
| Compound | Wild type | M-6-P-isomerase |
| D-mannose | 0 | 1.1 |
| D-mannosamine | 0 | 0.8 |
| D-mannose-6-phosphate | 0 | 0.7 |

EXAMPLE 32

Sugarbeet is transformed by the so-called cot-pet method as described in PCT Patent Application No. PCT DK92/

00108 wherein cotyledons including the petiole are used as explants. Seedlings are derived from seeds germinated and grown for 4–7 weeks at 12° C. in a 16 h day/8 h night regime. Cotyledons are excised 2–3 mm below the node, tawn apart and cultured either in the dark or in light and in the presence or absence of xylose. Table 29 shows that xylose is utilized as a carbohydrate source by sugarbeet in the presence of light but not in the dark indicating that xylose based positive selection of sugarbeet which are transgenic inter alia for the xylose isomerase gene should be carried out in the dark.

TABLE 29

Examination of the effect of D-xylose in sugarbeets in combination with sucrose with and without light.

| D-xylose (g/l) | Sucrose (g/l) | % expl. with shoots | weight (wet) (g) | Green (%) |
|---|---|---|---|---|
| Results after 3 weeds (light) | | | | |
| 0 | 10 | 98 | 7.41 | 100 |
| 0 | 0 | 13 | 0.64 | 60 |
| 10 | 0 | 90 | 1.53 | 90 |
| 10 | 10 | 97 | 5.47 | 100 |
| Results after 2 weeks in dark and 1 week in light | | | | |
| 0 | 10 | 50 | 1.38 | 97 |
| 0 | 0 | 0 | 0.36 | 47 |
| 10 | 0 | 13 | 0.37 | 77 |
| 10 | 10 | 80 | 0.89 | 97 |

EXAMPLE 33

Explants transgenic, inter alia, for the mannose 6-phosphate isomerase gene are produced, and the selection/regeneration substrate is supplemented with mannose and sucrose as indicated in Table 30. The number of regenerated shoots is registered after 11 weeks. Table 30 shows the number of regenerated shoots on substrates containing methyl-3-0-glucose as a percentage of the number of shoots regenerated on substrates without mannose and methyl-3-0-glucose.

TABLE 30

| | | Methyl-3-O-glucose | | | |
|---|---|---|---|---|---|
| Mannose | Sucrose | Wild type | | Man-6-P-isomerase | |
| g/l | g/l | 2.5 | 5.0 | 2.5 | 5.0 |
| 0 | 0 | 0 | 0 | 0 | 0 |
| 5 | 0 | 0 | 0 | 7 | 0 |
| 10 | 0 | 0 | 0 | 64 | 28 |
| 20 | 0 | 0 | 0 | 107 | 128 |
| 0 | 10 | 53 | 17 | 0 | 0 |
| 5 | 10 | 6 | 41 | 64 | 64 |
| 10 | 10 | 0 | 0 | 86 | 36 |
| 20 | 10 | 0 | 0 | 200 | 86 |

Regeneration of shoots on substrate containing sucrose (10 g/l), no mannose and no methyl 3-O-glucose:
Transgenic tissue: 1.4 shoots/explant
Wild type tissue: 1.7 shoots/explant

EXAMPLE 34

A. Utilization of mannose by maize callus culture

When callus cultures of 4 maize lines are plated in media containing different concentrations of sucrose (10 and 20 g/L) and D-mannose (0, 2.5, 5.0, 10.0, and 20 g/L) and in combinations thereof and evaluated after three weeks, the results indicate that mannose cannot be utilized as the sole carbohydrate source for maize and further that D-mannose is not toxic to maize callus culture.

Figure 6:
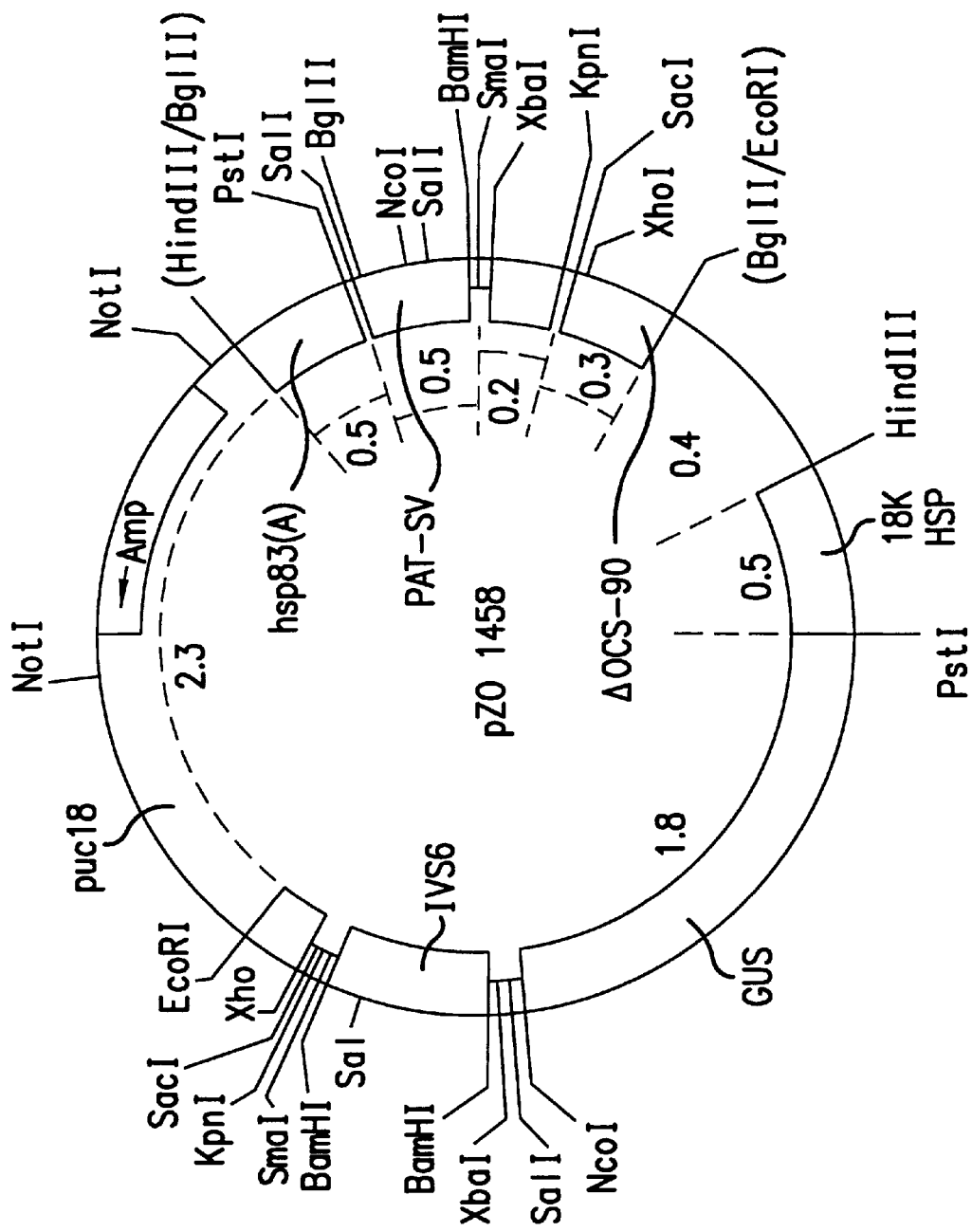
FIG. 6 shows plasmid pZO1458 containing GUS and PAT genes. The plasmid is used with pNKS205 in co-transformation of maize cells.
Figure 7:
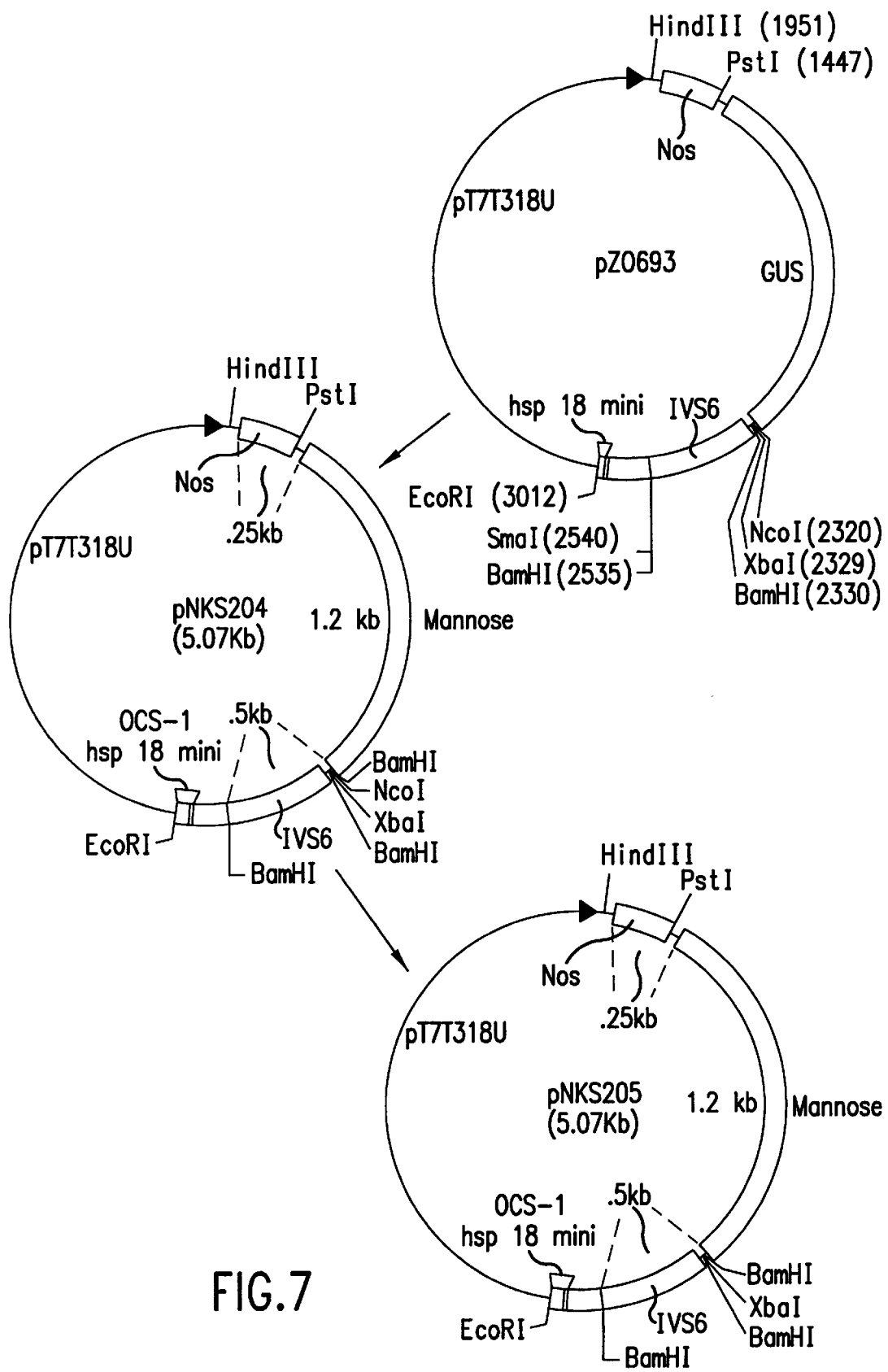
FIG. 7 shows plasmid pNKS204 and pNKS205 containing the mannose-6-phosphatase isomerase gene.

B. Utilization of mannose-6-phosphate isomerase gene as a selectable marker 120 immature maize Hightype II embryos (1.0–1.5 mm) are isolated from several maize ears on three consecutive days and plated on filters at a density of 60 embryos per filter. The filters are placed on N61DAP medium containing N6 salts supplemented with 1.0 mg/l 2,4-D, 1.45 g/l L-proline, 100 mg/l casein hydrolysate, 790 mg/l L-asparagine, 30 g/l sucrose, and vitamins (1 mg/l thiamine HC, 1 mg/l nicotinic acid, 0.2 mg/l pyridoxine, 100 mg/l I-inositol and 2 mg/l glycine) and solidified with 2.3 g/l of Gelrite (Schweizerhall, Inc). On day three the embryos are bombarded with 1 micron tungsten particles coated with the two plasmids pZO1458 (FIG. 6) and pNKS205 (FIG. 7). The model PDS-1000/He Particle delivery System (Bio-Rad) is used in the bombardment. Plasmid pZO1458 contains Phosphinothricin acetyl transferase (PAT) and GUS and is derived from a pUC 18 construct. Plasmid pNKS205 contains the mannose isomerase gene and is derived from pZO693 wherein the GUS gene is replaced with the mannose isomerase gene from pEPL-mannose (FIG. 3) and designated pNKS204. More specifically, the mannose isomerase gene is excised from the pEPL mannose construct at the PstI and SalI restriction sites and cloned into the pZO693 vector the NcoI and PstI restriction sites, originally containing the GUS gene. The construct is called pNKS204. The NcoI restriction site is deleted to obtain pNKS205. The plasmids are used at a ratio of 1:3.

After 7 days, the bombarded embryos and filters are transferred to a N6 1DAP medium wherein sucrose is replaced with 10 g/L D-mannose. The filters are kept in the mannose for 3 weeks and then transferred back to N6 1DAP. Recovered callus colonies are analyzed by PCR for GUS and M-6-P isomerase genes within a week. A month later the transgenic calli are also assayed for phosphomannose isomerase activity. Twelve stable transformed cell lines are obtained from 420 embryos. The results are presented in Table 31 below.

TABLE 31

Stable transformation frequency of bombarded immature embryos

| No of embryos | M+G+ | M+G− | M−G+ | M−G− | % transformation |
|---|---|---|---|---|---|
| 420 | 10 | 1 | 1 | 408 | 2.9 |

M = mannose; G = GUS; + = positive; and − = negative.

Additionally, GUS positives are confirmed by histochemical staining and mannose positives are confirmed by phosphomannose isomerase activity assay. Further experiments with immature embryos indicate that pre-culture on N6 1DAP for two days in the dark at 28° C. improves transformation frequency.

C. Regeneration of Transgenic Plants

Three transformed cell lines are transferred to regeneration medium containing MS salts and organics (Life Technologies) supplemented with 30 g/l of sucrose and solidified with 2.3 g/l Gelrite. Fifteen transgenic plants are regenerated and confirmed positive by standard PCR analysis. The fifteen plants are both male and female fertile. Seed has been harvested from the self- or cross pollinated plants. The results of the PCR analysis is reported below in Table 32.

TABLE 32

PCR analysis of transgenic maize plants

| Cell line | M+G+ | M+G− | M−G+ | M−G− | Total |
|---|---|---|---|---|---|
| B15-4A | 5 | 1 | 1 | 0 | 7 |
| B15-40 | 0 | 0 | 3 | 0 | 3 |
| B15-4Q | 5 | 0 | 0 | 0 | 5 |

M = mannose; G = GUS; + = positive; and − = negative.

D. Positive selection in maize protoplast PEG-mediated transformation

Maize protoplasts are prepared from three corn cell lines and mixed with PNK205 containing the M-6-P isomerase construct and pZO1458 containing the GUS and PAT construct as disclosed above in B at a ratio of 1:3 in 20% of polyethylene glycol solution for 30 minutes and then washed with N6 plus 8% sucrose. The transformed protoplasts are cultured on BMS feeder layers for one to four weeks before being treated with 2% mannose for one to two weeks. The stable transformation frequency as determined by the number of PCR positives compared to the total number of protoplasts is 47/17 million and equal to 0.00028%.

It will be appreciated that the present invention is not limited to the above identified Examples. For example, tissue specific expression of a gene encoding an enzyme involved in mannose or xylose metabolism, or the metabolism of a mannose or xylose derivative or a mannose or xylose precursor may be used to control developmental regulation of such tissues upon exposure thereof to the substrate of modulator of the said enzyme. Moreover, mannose or xylose (including derivatives or precursors thereof) may be used as a selective herbicide to selectively advantage crops which have been transformed to include genes encoding proteins involved in the metabolism of such xylose or mannose or their precursors or derivatives.

What is claimed:

1. Genetically transformed plant cells comprising a desired nucleotide sequence and a co-introduced nucleotide sequence wherein expression or transcription of the co-introduced nucleotide sequence in the transformed cells gives said transformed cells a competitive advantage when a population of cells including the transformed and the non-transformed cells is supplied with a compound that only the transformed cells are able to utilize, and the desired nucleotide sequence codes for a gene other than a toxin, antibiotic or herbicide resistance gene.

2. Transformed plants derived from the cells of claim 1.

3. Seeds produced from the transformed plants of claim 2, wherein said seeds are capable of germinating to produce transformed plants.

4. Genetically transformed maize cells comprising a desired nucleotide sequence and a co-introduced nucleotide sequence wherein the co-introduced nucleotide sequence gives the transformed cells a competitive advantage when a population of cells including the transformed cells and nontransformed cells is supplied with a compound, wherein the co-introduced nucleotide sequence codes for a phosphomanno-isomerase or a mannophosphatase and the compound is mannose, a mannose derivative or a mannose precursor.

5. Maize plants derived from the transformed cells of claim 4.

6. Seeds produced from the transformed maize plants of claim 5, wherein said seeds are capable of germinating to produce transformed maize plants.

7. A method of selecting genetically transformed cells from a population of cells comprising the steps of:

a) introducing into the genome of a plant cell a desired nucleotide sequence and a co-introduced nucleotide sequence wherein said desired nucleotide sequence or co-introduced nucleotide sequence codes for a sequence other than a toxin, antibiotic or herbicide resistance gene;

b) obtaining transformed cells;

c) supplying to the population of cells a compound that only transformed cells are able to utilize wherein said transformed cells have a competitive advantage over non-transformed cells due to the expression or transcription of the desired nucleotide sequence or co-introduced nucleotide sequence in the presence of the compound; and d) selecting said transformed cells from the population of cells.

8. The method of claim 7 wherein the desired nucleotide sequence or the co-introduced nucleotide sequence comprises a region which: (a) encodes a protein which is involved in the metabolism of the compound or (b) regulates the activity of a gene encoding the protein or both.

9. The method of claim 8 wherein the protein is selected from the group consisting of xyloisomerases, phosphosugar-isomerases, phosphosugar-mutases, phosphatase, sugar epimerases, sugar-permease and phosphosugar-permease.

10. The method of claim 9 wherein the protein is a phosphomanno-isomerase, a xylose isomerase, a phosphomanno mutase or a mannose epimerase.

11. The method of claim 8 wherein the protein is mannose-6-phosphate isomerase, mannose-1-phosphate isomerase, mannose-6-phosphatase or mannose-1-phosphatase.

12. The method of claim 7 wherein the desired nucleotide sequence or co-introduced nucleotide sequence encodes a protein which is β-glucuronidase.

13. The method of claim 7 wherein the desired nucleotide sequence or co-introduced nucleotide sequence encodes a protein which is a permease.

14. The method of claim 7 wherein expression or transcription of the co-introduced nucleotide sequence or desired nucleotide sequence results in blockage of the metabolism of the compound.

15. The method of claim 7 wherein at least one of the nucleotide sequences comprises DNA which is modified wherein codons which are preferred by the plant organism into which the sequences are introduced are used so that expression of the modified DNA in the organism yields substantially similar protein to that obtained by expression of the unmodified DNA in the organism in which the protein-encoding components of the sequences are endogenous.

16. The method of claim 7 wherein the compound is selected from the group consisting of an inactivated cytokinin, auxin or gibberellin; a carbohydrate; a protein; a vitamin; an opine; a sterol and a saponin.

17. The method according to claim 7 wherein the desired nucleotide sequence and the co-introduced nucleotide sequence are introduced on the same vector.

18. The method according to claim 7 wherein the desired nucleotide sequence and the co-introduced nucleotide sequence are on different vectors.

19. The method according to claim 7 wherein the compound is an opine and the desired nucleotide sequence is an opine metabolism or transport gene wherein the opine metabolism or transport gene allows the opine to function as an amino acid, nitrogen or carbohydrate source in the transformed cells.

20. The method of claim 16 wherein the compound is mannose, galactose, xylose, or a derivative thereof.

21. The method of claim 12 wherein the compound is a β-glucuronidase inhibitor.

22. The method of claim 12 wherein the compound is a cytokinin glucuronide.

23. The method of claim 7 wherein the cells have been transformed by a bacterium which is sensitive to the compound.

24. The method of claim 7 further comprising supplying to the population of cells an agent which reduces the toxicity of the compound to the cells.

25. The method of claim 24 wherein the agent is methyl-3-o-glucose or phloridzin.

26. The method of claim 7 further comprising the step of regenerating a plant from said transformed cells.

27. A method of selecting genetically transformed maize cells from a population of cells comprising the steps of:
   a) introducing into the genome of a maize cell a desired nucleotide sequence and a co-introduced nucleotide;
   b) obtaining transformed cells;
   c) supplying to the population of cells a compound wherein said transformed cells have a competitive advantage over non-transformed cells due to the expression or transcription of the desired nucleotide sequence or co-introduced nucleotide sequence in the presence of the compound; and
   d) selecting said transformed cells from the population of cells wherein said co-introduced nucleotide sequence comprises a sequence encoding a phosphomanno-isomerase or a manno-phosphatase and the compound is mannose, a mannose derivative or a mannose precursor.

28. The method of claim 27 wherein the transformed cells are protoplasts.

29. The method of claim 22 wherein the cytokinin glucuronide is of formula I

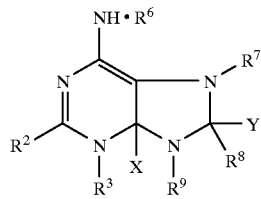

and is selected from the group consisting of:

a compound of formula I wherein $R^2$ is H, $R^3$ is a β-D-glucopyranuronosyl group or a salt thereof at the carboxylic acid function, $R^9$ and X are half-bonds which together form a bond, $R^6$ is benzyl, $R^7$ and Y are half-bonds which together form a bond, and $R^8$ is H;

a compound of formula I wherein $R^2$ is H, $R^3$ is the amide derivative of β-D-glucopyranuronosyl at the carboxylic acid function thereof, $R^9$ and X are half-bonds which together form a bond, $R^6$ is benzyl, $R^7$ and Y are half-bonds which together form a bond, and $R^8$ is H;

a compound of formula I wherein $R^2$ is H, $R^3$ and X are half-BONDS which together form a bond, $R^9$ is a β-D-glucopyranuronosyl group or a salt thereof at the carboxylic acid function, $R^6$ is benzyl, $R^7$ and Y are half-bonds which together form a bond, and $R^8$ is H;

a compound of formula I wherein $R^2$ is H, $R^3$ is a β-D-glucopyranuronosyl group or a salt thereof at the carboxylic acid function, $R^9$ and X are half-bonds which together form a bond, $R^6$ is 2-isopentenyl, $R^7$ and Y are half-bonds which together form a bond, and $R^8$ is H;

a compound of formula I wherein $R^2$ is an —S-β-D-glucopyranuronosyl group or a salt thereof at the carboxylic acid function, $R^9$ is H, $R^3$ and X are half-bonds which together form a bond, $R^6$ is 2-isopentenyl, $R^7$ and Y are half-bonds which together form a bond, and $R^8$ is H;

a compound of formula I wherein $R^2$ is H, $R^9$ is H, $R^3$ and X are half-bonds which together form a bond, $R^6$ is 2-isopentenyl, $R^7$ and Y are half-bonds which together form a bond, and $R^8$ is an —S-β-D-glucopyranuronosyl group or a salt thereof at the carboxylic acid function; and a compound of formula I wherein $R^2$ is H, $R^3$ and X are half-bonds which together form a bond, $R^9$ is H, $R^6$ is a group of the formula

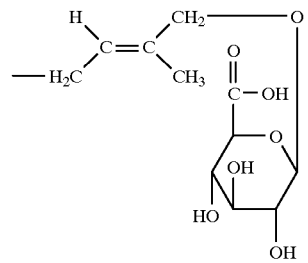

or a salt thereof, $R^7$ and Y are half-bonds which together form a bond, and $R^8$ is H.

30. The method of claim 22 wherein the cytokinin glucuronide is of formula II

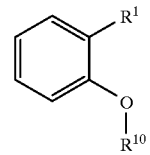

wherein $R^1$ is a cis- —CH═CH—COOH, a salt thereof or an ester derivative thereof at the carboxylic acid function, or the amide derivative of cis- and/or trans- —CH═CH—COOH, and $R^{10}$ is a β-glucupyranuronosyl group or a salt thereof or an ester or amide derivative thereof at the carboxylic acid function.

* * * * *